(12) United States Patent
Chandrakumar et al.

(10) Patent No.: US 6,689,754 B1
(45) Date of Patent: Feb. 10, 2004

(54) HETEROCYCLIC GLYCYL β-ALANINE DERIVATIVES

(75) Inventors: Nizal Samuel Chandrakumar, Vernon Hills, IL (US); Bipinchandra Nanubhai Desai, Vernon Hills, IL (US); Balekudru Devadas, Chesterfield, MO (US); Alan Frank Gasiecki, Vernon Hills, IL (US); Renee Huff, Park Ridge, IL (US); Ish K. Khanna, Vernon Hills, IL (US); James W. Malecha, Libertyville, IL (US); Julie M. Miyashiro, Skokie, IL (US); Shashidhar N. Rao, Mundelein, IL (US); Joseph Gerace Rico, Ballwin, MO (US); Thomas Edward Rogers, Ballwin, MO (US); Peter Gerrard Ruminski, Dardenne Prairie, MO (US); Mark Andrew Russell, Gurnee, IL (US); Yi Yu, Skokie, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/289,140

(22) Filed: Apr. 8, 1999

Related U.S. Application Data

(60) Provisional application No. 60/081,394, filed on Apr. 10, 1998.

(51) Int. Cl.[7] .................................................. C07K 5/06
(52) U.S. Cl. .............................. 514/20; 514/19; 546/304
(58) Field of Search ........................ 514/19, 20; 546/304

(56) References Cited

FOREIGN PATENT DOCUMENTS

| CA | 2211270 | 1/1998 |
|---|---|---|
| WO | WO 91 04247 A | 4/1991 |
| WO | WO 97 08145 A | 3/1997 |
| WO | 0820991 A2 | 1/1998 |
| WO | WO 98 08840 A | 3/1998 |

*Primary Examiner*—Christopher S. F. Low
*Assistant Examiner*—David Lukton
(74) *Attorney, Agent, or Firm*—Cynthia Kovacevic; Rachel A. Polster

(57) ABSTRACT

The present invention relates to a class of compounds represented by the Formula I

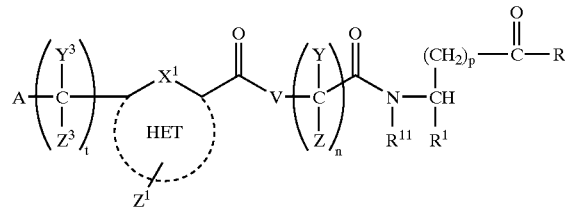

or a pharmaceutically acceptable salts thereof, pharmaceutical compositions containing such compounds and methods of treating conditions mediated by the $\alpha_v\beta_3$ integrin.

15 Claims, No Drawings

HETEROCYCLIC GLYCYL β-ALANINE DERIVATIVES

The present application claims priority under 35 USC §119(e) of U.S. provisional patent application Ser. No. 60/081,394, filed Apr. 10, 1998.

FIELD OF THE INVENTION

The present invention relates to pharmaceutical agents (compounds) which are useful as $\alpha_v\beta_3$ integrin antagonists and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked α and β polypeptide subunits. Currently eleven different a subunits have been identified and six different β subunits have been identified. The various α subunits can combine with various β subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy including macular degeneration, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix, and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

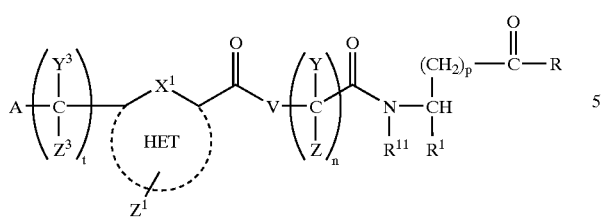

or a pharmaceutically acceptable salt thereof, wherein

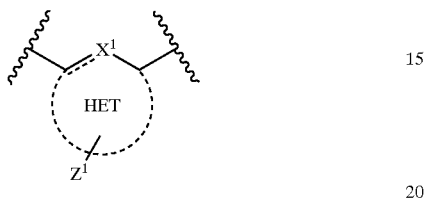

is a 5–8 membered monocyclic heterocyclic ring, optionally unsaturated, containing 1 to 4 heteroatoms, selected from the group consisting of O, N or S, wherein $X^1$ is selected from the group consisting of CH, $CH_2$, N, NH, O and S;

A is

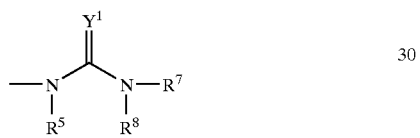

wherein $Y^1$ is selected from the group consisting of $N-R^2$, O, and S;

$R^2$ is selected from the group consisting of H; alkyl; aryl; hydroxy; alkoxy; cyano; nitro; amino; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl; alkyl optionally substituted with one or more substituent selected from lower alkyl, halogen, hydroxyl, haloalkyl, cyano, nitro, carboxyl, amino, alkoxy, aryl, or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl; or $R^2$ taken together with $R^7$ forms a 4–12 membered heterocycle containing one or more heteroatom selected from O, N and S optionally unsaturated; or $R^2$ taken together with $R^7$ forms a 5–9 membered heteroaromatic ring optionally substituted with one or more substituent selected from lower alkyl, phenyl, alkoxy and hydroxy; or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

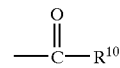

wherein $R^{10}$ is defined above; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or

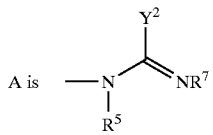

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—$R^9$ and —O—$R^9$ wherein $R^9$ is selected from the group consisting of H; alkyl; aralkyl; aryl; alkenyl; and alkynyl; or $R^9$ taken together with $R^7$ forms a 4–12 membered mononitrogen and monosulfur or monooxygen containing heterocyclic ring optionally substituted with lower alkyl, hydroxy, keto, phenyl, carboxyl or carboxyl ester, and fused phenyl; or $R^9$ taken together with $R^7$ is thiazole; oxazole; benzoxazole; or benzothiazole; and $R^5$ and $R^7$ are as defined above; or $Y^2$ (when $Y^2$ is carbon) taken together with $R^7$ forms a 4–12 membered mononitrogen or dinitrogen containing ring optionally substituted with alkyl, aryl, keto or hydroxy;

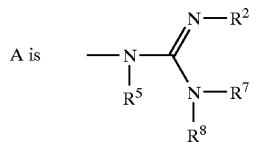

where $R^2$ and $R^7$ taken together form a 5–8 membered dinitrogen containing heterocycle optionally substituted with one or more substituent selected from the group consisting of lower alkyl, hydroxy, alkoxy, keto, phenyl, or carboxyl derivatives; and $R^8$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; and $R^5$ is defined as above or $R^2$ and $R^7$ taken together form a heteroaromatic ring such as imidazole or pyrimidone;

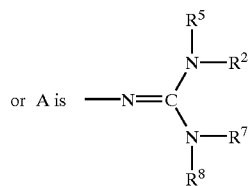

where $R^2$ and $R^7$ taken together form a 5–8 membered dinitrogen containing heterocycle optionally substituted with hydroxy, keto, phenyl, or alkyl; and $R^8$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

$Z^1$ is one or more substituent selected from the group consisting of H; alkyl; hydroxy; alkoxy; aryloxy; halogen; haloalkyl; haloalkoxy; nitro; amino; alkylamino; acylamino; dialkylamino; cyano; alkylthio; alkylsulfonyl; carboxyl derivatives; trihaloacetamide; acetamide; acyl; aryl; fused aryl; cycloalkyl; thio; monocyclic heterocycles; fused monocyclic heterocycles; and A, wherein A is defined above;

V is selected from the group consisting of —N—($R^6$)— wherein $R^6$ is selected from the group consisting of H; lower alkyl; cycloalkyl; aralkyl; aryl; and monocyclic heterocycles; or $R^6$ taken together with Y, forms a 4–12 membered mononitrogen containing ring;

Y, $Y^3$, Z and $Z^3$ are independently selected from the group consisting of hydrogen; alkyl; aryl; and cycloalkyl; or Y and Z taken together form a cycloalkyl; or $Y^3$ and $Z^3$ taken together form a cycloalkyl;

n is an integer 1, 2, or 3;

t is an integer 0, 1, or 2;

p is an integer 0, 1, 2, or 3;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids; polyalkylethers; alkylamido; alkyl N,N-dialkylamido; pivaloyloxymethyl; and in the case of the free acid, all pharmaceutically acceptable salts thereof;

$R^1$ is selected from the group consisting of hydrogen; alkyl; alkenyl; alkynyl; aryl; carboxyl derivatives; haloalkyl; cycloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

alkylcarbonyl, haloalkylcarbonyl, and arylcarbonyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy; amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

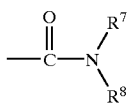

wherein $R^7$ and $R^8$ are as defined above and provided that taken together with the nitrogen, $R^7$ and $R^8$ comprise an amino acid; and $R^{11}$ is selected from the group consisting of H, alkyl, aralkyl, alkenyl, alkynyl, haloalkyl or haloalkynyl or $R^{11}$ taken together with Y forms a 4–12 membered mononitrogen containing ring.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

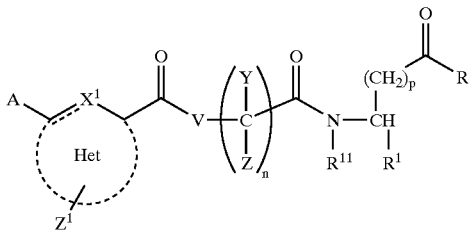

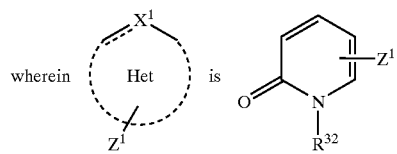

wherein $R^{32}$ is H, alkyl, alkoxyalkyl, aminoalkyl, dialkylamino alkyl, wherein the alkyl group is optionally substituted by one or more substituent selected from the group consisting of hydroxy, alkoxy, amino, alkylamino, dialkylamino, aryl- or alkyl-sulfonyl, carboxyl, and carboxyl derivatives and the other variables are as described in Formula I.

Another preferred embodiment of the present invention is a compound of the Formula III

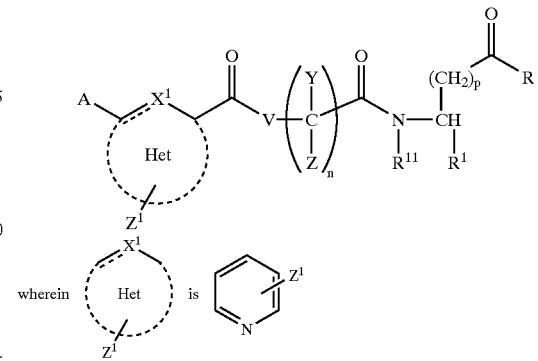

optionally substituted and the other variables are as defined above in Formula I.

Another preferred embodiment of the present invention is a compound of the Formula IV

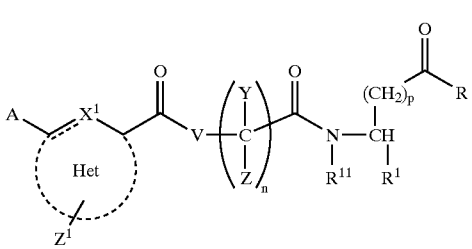

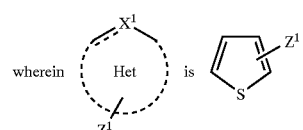

optionally substituted and the other variables are as defined above in Formula I.

Another preferred embodiment of the present invention is a compound of the Formula V

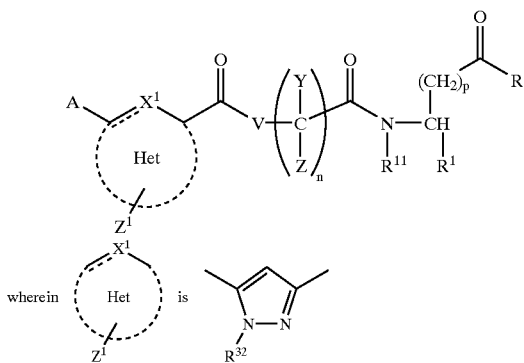

optionally substituted and the other variables are as defined above in Formula I.

Another preferred embodiment of the present invention is a compound of the Formula VI

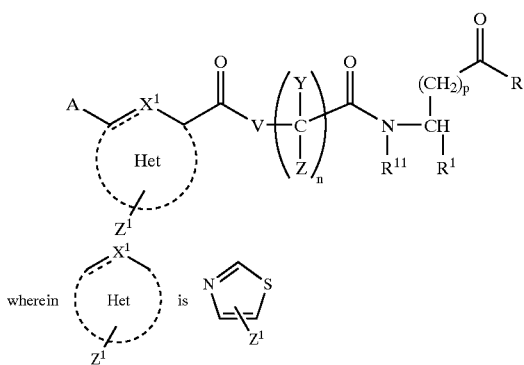

optionally substituted and the other variables are as defined above in Formula I.

The invention further relates to pharmaceutical compositions containing therapeutically effective amounts of the compounds of Formulas I–VI.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration and restenosis by administering a therapeutically effective amount of a compound of the Formula I–VI to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

The terms "hydroxy" and "hydroxyl" as used herein are synonymous and are represented by a radical of the formula

The radical of the formula

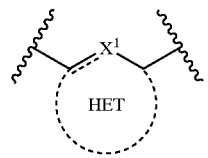

refers to a 5–10 membered monocyclic or bicyclic heterocyclic ring, optionally containing unsaturation, containing 1 to 3 hetero atoms selected from the group consisting of O, N and S; wherein $X^1$ is CH, N, O or S. Representative examples of the radical include pyridones, pyridines, pyrimidines, imidazoles, oxazoles, isoxazoles, thiazoles, pyridazines, thiophenes, furans, pyrazoles and bicyclic heterocyclics such as benzimidazole, imidazopyridine, benzofuran and the like.

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —$OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

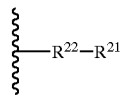

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula —COOR$^{23}$ wherein $R^{23}$ is selected from the group consisting of H, alkyl, aralkyl or aryl as defined above.

As used herein the term "carboxyl derivative" refers to a radical of the formula

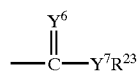

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —NH$_2$.

As used herein the term "alkylsulfonyl" or "alkylsulfone" refers to a radical of the formula

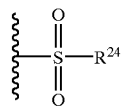

wherein $R^{24}$ is alkyl as defined above.

As used herein the term "alkylthio" refers to a radical of the formula —SR$^{24}$ wherein $R^{24}$ is alkyl as defined above.

As used herein the term "sulfonic acid" refers to a radical of the formula

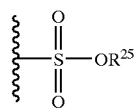

wherein $R^{25}$ is alkyl as defined above.

As used herein the term "sulfonamide" refers to a radical of the formula

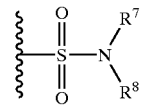

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

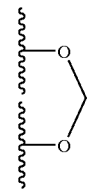

and the term "ethylenedioxy" refers to the radical

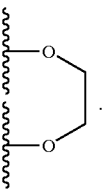

As used herein the term "4–12 membered dinitrogen containing heterocycle refers to a radical of the formula

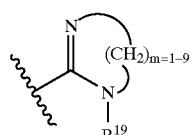

wherein m is 1 or 2 and $R^{19}$ is H, alkyl, aryl, or aralkyl and more preferably refers to 4–9 membered ring and includes rings such as imidazoline.

As used herein the term "5-membered optionally substituted heteroaromatic ring" includes for example a radical of the formula

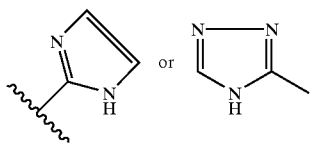

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

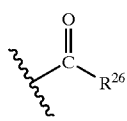

wherein $R^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula

As used herein the term "sulfonyl" refers to a radical of the formula

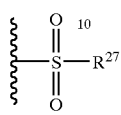

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

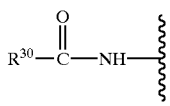

wherein $R^{30}$ is alkyl, aralkyl or aryl as defined above.

As used herein the term "amido" refers to a radical of the formula

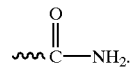

As used herein the term "alkylamino" refers to a radical of the formula —NHR$^{32}$ wherein $R^{32}$ is alkyl as defined above.

As used herein the term "dialkylamino" refers to a radical of the formula —NR$^{33}$R$^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

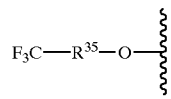

wherein $R^{35}$ is a bond or an alkylene as defined above.

As used herein the term "alkylaminosulfonyl" refers to a radical of the formula

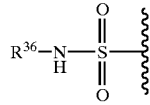

wherein $R^{36}$ is alkyl as defined above.

As used herein the term "alkylsulfonylamino" refers to a radical of the formula

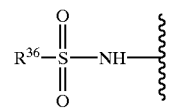

wherein $R^{36}$ is alkyl as defined above.

As used herein the term "trifluoromethylthio" refers to a radical of the formula

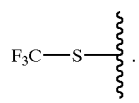

As used herein the term "trifluoromethylsulfonyl" refers to a radical of the formula

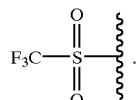

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

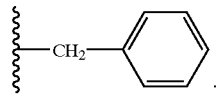

As used herein the term "phenethyl" refers to the radical

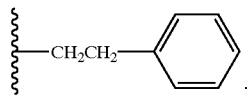

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

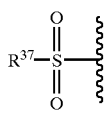

wherein $R^{37}$ is aryl as defined above.

As used herein the terms "alkylsulfoxide" or "arylsulfoxide" refer to radicals of the formula

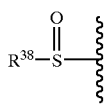

wherein $R^{38}$ is, respectively, alkyl or aryl as defined above.

As used herein the term "phosphonic acid derivative" refers to a radical of the formula

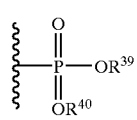

wherein $R^{39}$ and $R^{40}$ are the same or different H, alkyl, aryl or aralkyl.

As used herein the term "phosphinic acid derivatives" refers to a radical of the formula

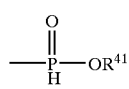

wherein $R^{41}$ is H, alkyl, aryl or aralkyl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

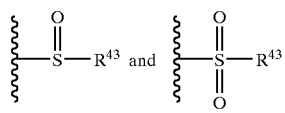

wherein $R^{43}$ is a monocyclic heterocycle radical as defined above.

As used herein the term "alkylcarbonyl" refers to a radical of the formula

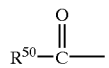

wherein $R^{50}$ is alkyl as defined above.

As used herein the term "arylcarbonyl" refers to a radical of the formula

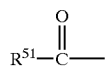

wherein $R^{51}$ is aryl as defined above.

As used herein the term "alkoxycarbonyl" refers to a radical of the formula

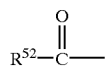

wherein $R^{52}$ is alkoxy as defined above.

As used herein the term "aryloxycarbonyl" refers to a radical of the formula

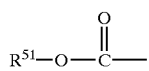

wherein $R^{51}$ is aryl as defined above.

As used herein the term "haloalkylcarbonyl" refers to a radical of the formula

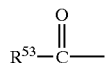

wherein $R^{53}$ is haloalkyl as defined above.

As used herein the term "haloalkoxycarbonyl" refers to a radical of the formula

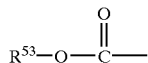

wherein $R^{53}$ is haloalkyl as defined above.

As used herein the term "alkylthiocarbonyl" refers to a radical of the formula

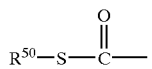

wherein $R^{50}$ is alkyl as defined above.

As used herein the term "arylthiocarbonyl" refers to a radical of the formula

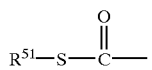

wherein $R^{51}$ is aryl as defined above.

As used herein the term "acyloxymethoxycarbonyl" refers to a radical of the formula

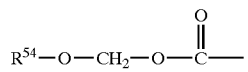

wherein $R^{54}$ is acyl as defined above.

As used herein the term "arylamino" refers to a radical of the formula $R^{51}$—NH— wherein $R^{51}$ is aryl as defined above.

As used herein the term "polyalkylether" refers to commonly used glycols such as triethyleneglycol, tetraethylene glycol, polyethylene glycol and the like.

As used herein the term "alkylamido" refers to a radical of the formula

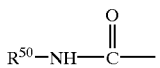

wherein $R^{50}$ is alkyl as defined above.

As used herein the term "N,N-dialkylamido" refers to a radical of the formula

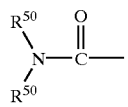

wherein $R^{50}$ is the same or different alkyl group as defined above.

As used herein the term "pivaloyloxymethyl" refers to a radical of the formula

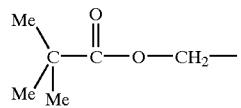

As used herein the term "acyloxy" refers to a radical of the formula $R^{55}$—O— wherein $R^{55}$ is acyl as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
Ar=argon
BH$_3$-THF=borane-tetrahydrofuran complex
Bn=benzyl
BOC=<u>tert</u>-butoxycarbonyl
ButLi=butyl lithium
Cat.=catalytic amount
CDMT=2-chloro-4,6-dimethoxytriazine
CH$_2$Cl$_2$=dichloromethane
CH$_3$CN=acetonitrile
CH$_3$I=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DAST=diethylaminosulfur trifluoride
DCC=1,3-dicyclohexylcarbodiimide
DCM=dichloromethane
DIBAL=diisobutylaluminum hydride
DIEA=diisopropylethylamine
DI water=deionized water
DMA=<u>N</u>,<u>N</u>-dimethylacetamide
DMAC=<u>N</u>,<u>N</u>-dimethylacetamide
DMAP=4-(<u>N</u>,<u>N</u>-dimethylamino)pyridine
DMF=<u>N</u>,<u>N</u>-dimethylformamide
DSC=disuccinyl carbonate
EDCI=1-(3-dimethylaminopropyl)-3-ethylcarbodiimide hydrochloride
Et=ethyl
Et$_2$O=diethyl ether
Et$_3$N=triethylamine
EtOAc=ethyl acetate
EtOH=ethanol
FAB MS=fast atom bombardment mass spectroscopy
g=gram(s)
GIHA=meta-guanidinohippuric acid
GIHA HCl=meta-guanidinohippuric acid hydrochloride
Gly=glycine
HMPA=hexamethylphosphoramide HOBT=1-hydroxybenzotriazole hydrate
HPLC=high performance liquid chromatography
IBCF=isobutylchloroformate
i-Pr=iso propyl
i-Prop=iso propyl
$K_2CO_3$=potassium carbonate
$KMnO_4$=potassium permanganate
KOH=potassium hydroxide
KSCN=potassium thiocyanate
L=Liter
LiOH=lithium hydroxide
MCPBA=m-chloroperoxybenzoic acid or m-chloroperbenzoic acid
Me=methyl
MeI=methyl iodide
MeOH=methanol
MEMCl=methoxyethoxy methyl chloride
MesCl=methanesulfonylchloride
mg=milligram
$MgSO_4$=magnesium sulfate
ml=milliliter
mL=milliliter
MS=mass spectroscopy
MTBE=methyl t-butyl ether
$N_2$=nitrogen
$NaCNBH_3$=sodium cyanoborohydride
NaH-sodium hydride
$NaHCO_3$=sodium bicarbonate
NaOH=sodium hydroxide
NaOMe=sodium methoxide
$Na_2PO_4$=sodium phosphate
$Na_2SO_4$=sodium sulfate
$NEt_3$=triethylamine
$NH_4HCO_3$=ammonium bicarbonate
$NH_4^+HCO_2^-$=ammonium formate
$NH_4OH$=ammonium hydroxide
NMM=N-methylmorpholine
NMP=1-methyl-2-pyrrolidinone
NMR=nuclear magnetic resonance
Pd/C=palladium on carbon
Ph=phenyl
Pt/C=platinum on carbon
RPHPLC=reverse phase high performance liquid chromatography
RT=room temperature
t-BOC=tert-butoxycarbonyl
TFA=trifluoroacetic acid
THF=tetrahydrofuran
TLC-thin layer chromatography
TMEDA=tetramethylethylenediamine
TMS=trimethylsilyl
Δ=heating the reaction mixture The compounds as shown in Formulas I–VI can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J. Pharm. Sci* 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–VI, wherein one or more compounds of the Formulas I–VI is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptors. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg per kilogram of body weight per day are useful in the treatment of the above-indicated conditions.

The active ingredient administered by injection is formulated as a composition wherein, for example, saline, dextrose or water may be used as a suitable carrier. A suitable daily dose would typically be about 0.01 to 10 mg/kg body weight injected per day in multiple doses depending on the factors listed above.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes 1–15. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention.

Unless otherwise indicated all starting materials and equipment employed were commercially available.

SCHEME 1

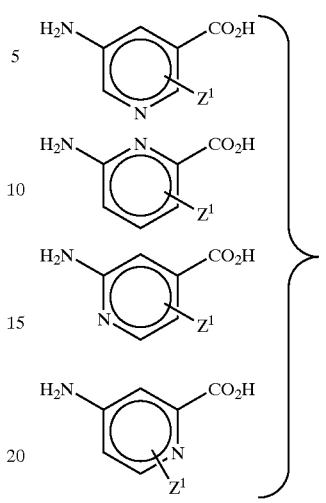

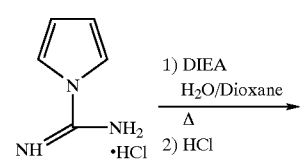

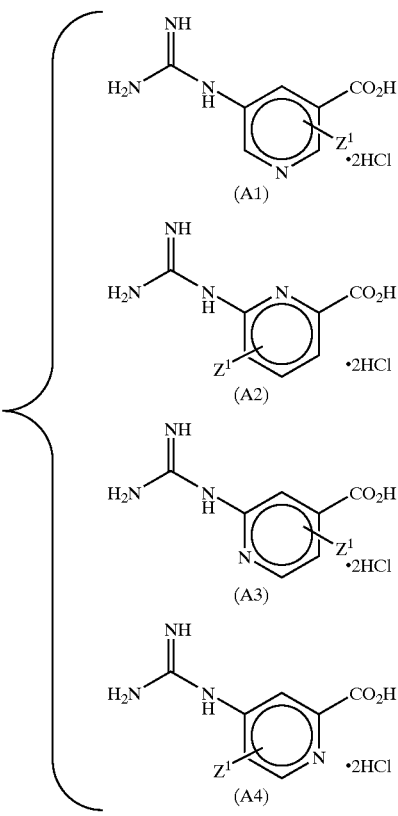

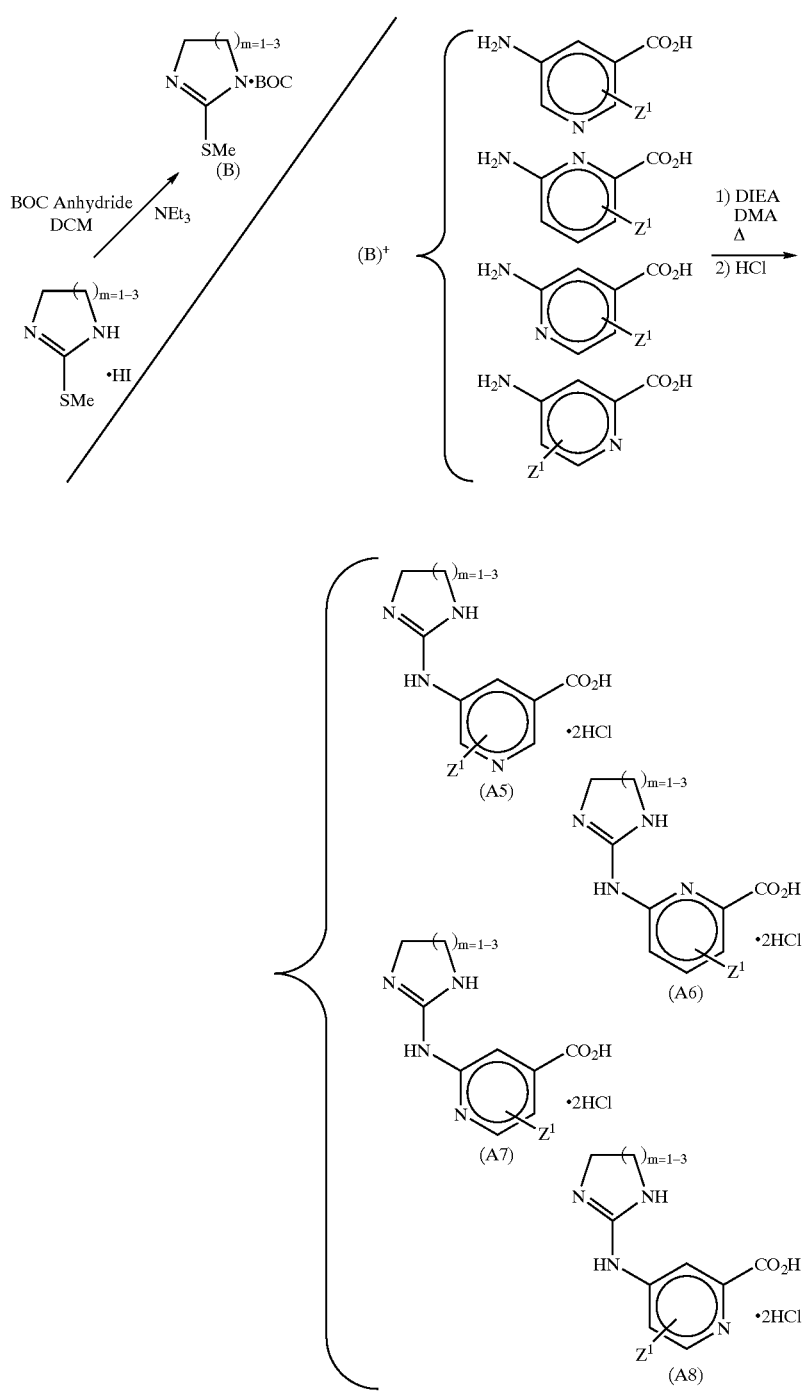
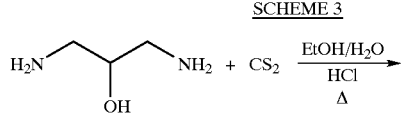
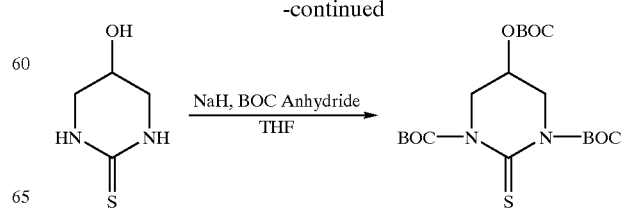

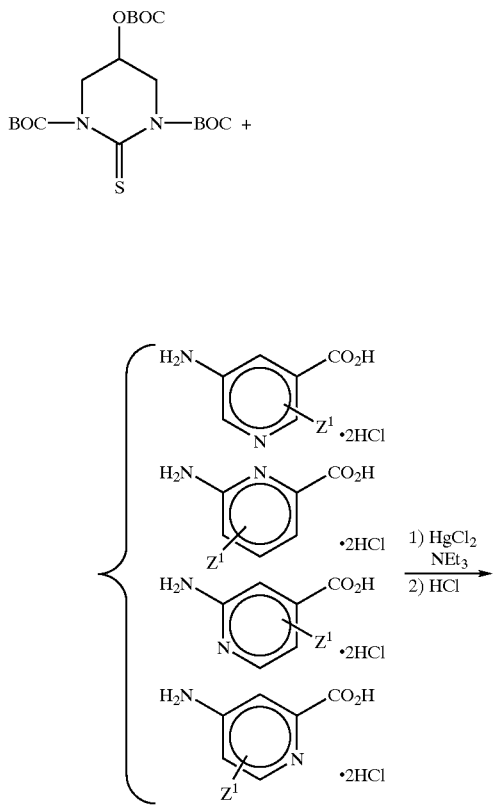

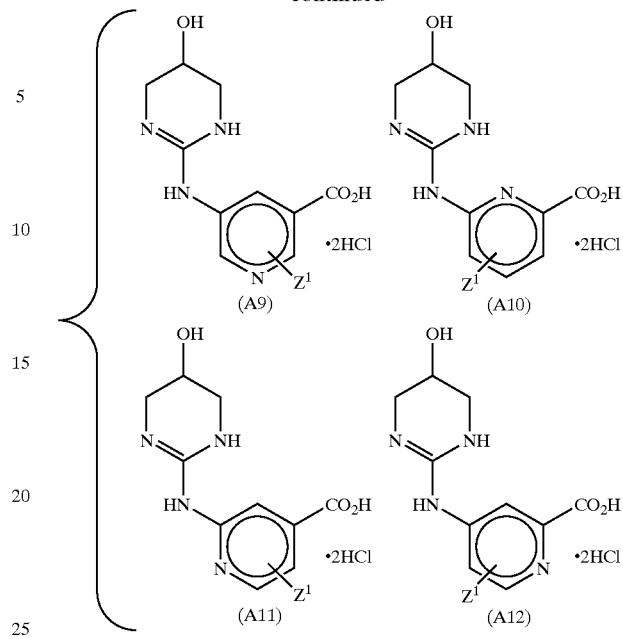

Schemes 1–3 are illustrative of methodology useful for preparing the guanidinopyridine/cycloguanidino pyridine carboxylic acid portions of the present invention which are used for coupling to the gly-β-amino acid portion. This can be accomplished using other appropriate guanidating reagents known to those skilled in the art. The methodologies of Schemes 1–3 can be modified using conventional techniques and methods to prepare alternate compounds useful for coupling to the gly-β-amino acid portion.

SCHEME 4

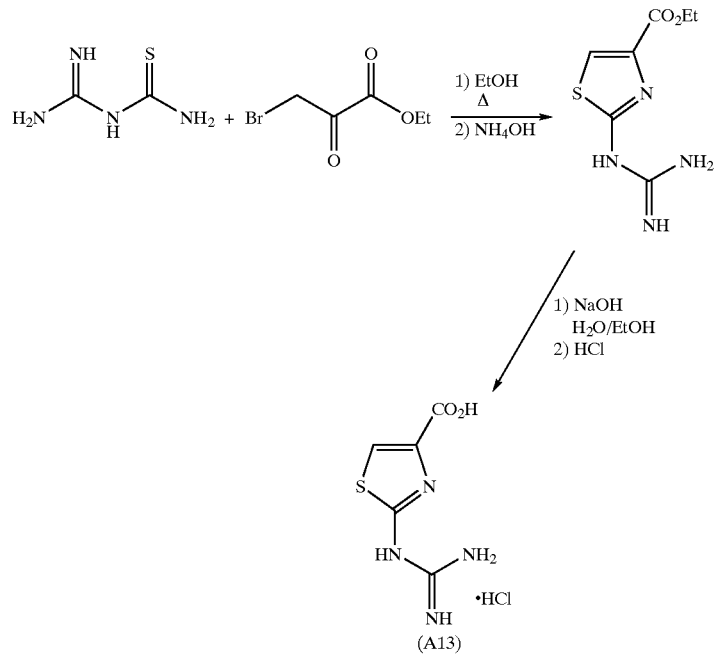

Scheme 4 is illustrative of methodology used for preparing the guanidinothiazole carboxylic acid portion of the present invention which is used for coupling to the gly-β-amino acid portion. The methodology of Scheme 4 can be modified using conventional techniques known to those skilled in the art to prepare this and alternate compounds useful for coupling to the gly-β-amino acid portion.

and subjecting the reaction mixture to conventional work-up conditions. 3-iodo-5-bromosalicylaldehyde can be prepared by reacting 5-bromosalicylaldehyde in acetonitrile with potassium iodide and chloramine T. Conventional work-up gives a material that when treated with hexanes gives the desired 3-iodo-5-chlorosalicylaldehyde.

Coumarins are readily prepared from salicylaldehydes using a modified Perkin reaction (e.g., *Vogel's Textbook of*

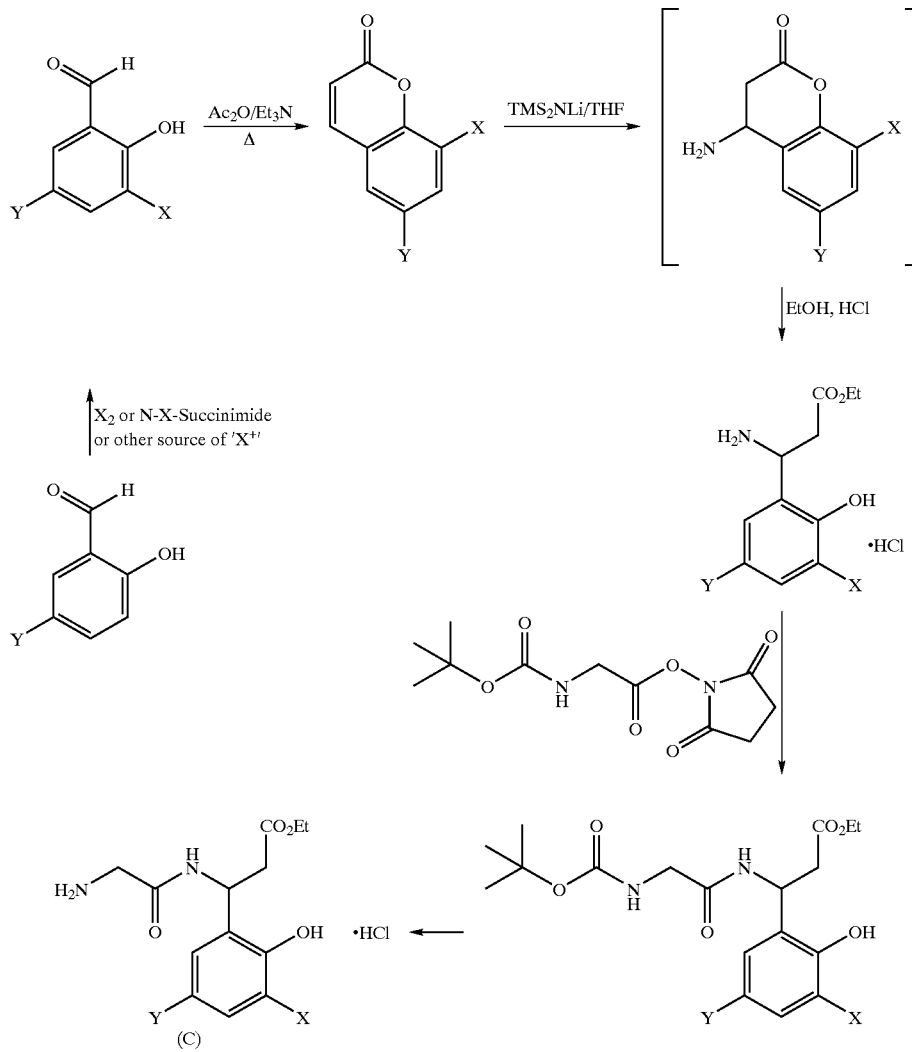

SCHEME 5

Scheme 5 illustrates methodology useful for preparing the ethyl N-gly-amino-3-(3,5-dihalo-2-hydroxy)phenyl propionate portion of the compounds of the present invention. Briefly, 3,5-halo substituted salicylaldehydes (halo substituted -2-hydroxybenzaldehydes) were prepared by direct halogenation. For example, 5-bromosalicylaldehyde is slurried in acetic acid and an equivalent or more of chlorine is added to produce 3-chloro-5-bromo-2-hydroxybenzaldehyde.

Some product precipitates and is recovered by filtration. The remainder is recovered by diluting the filtrate with water and isolating the precipitate. Combining the solids and drying gives 3-chloro-5-bromo-2-hydroxybenzaldehyde. 3-iodo-5-chlorosalicylaldehyde was prepared by reacting 5-chlorosalicylaldehyde with N-iodosuccinimide in DMF

*Practical Organic Chemistry,* 5$^{th}$ Ed., 1989, p.1040). The halo-substituted coumarins were converted to 3-aminohydrocoumarins (see J. G. Rico, *Tett. Let.,* 1994, 35, 6599–6602) which were readily opened in acidic alcohol to give 3-amino-3-(3,5-halo-2-hydroxy)phenyl propanoic acid esters.

3-amino-3-(3,5-halo-2-hydroxy)phenyl propanoic acid esters were converted to N-gly-3-amino-3(3,5-halo-2hydroxy)phenyl propanoic acid esters by reaction of Boc-N-gly-N-hydroxysuccinimide to give Boc-N-gly-3-amino-3-(3,5-halo-2-hydroxy)phenyl propanoic acid esters that were converted to HX salts of N-gly-3-amino-3-(3,5-halo-2-hydroxy)phenyl propanoic acid esters (wherein X is Cl, Br or I).

SCHEME 6

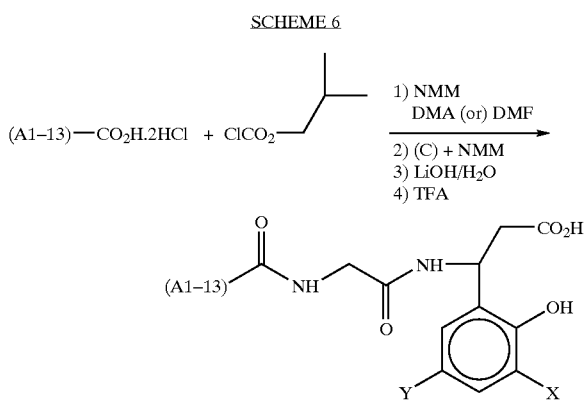

Scheme 6 illustrates methodology useful for coupling the heterocyclic acid portion (A1-A13) to the gly-β-amino portion (C) of the present invention.

Synthesis of A1-A13 is illustrated in Schemes 1–4 and synthesis of (C) is illustrated in Scheme 5 (where X and Y were halogen, same or different).

Such methodology can be modified using conventional methods known to those with ordinary skill in the art.

SCHEME 7

Step A

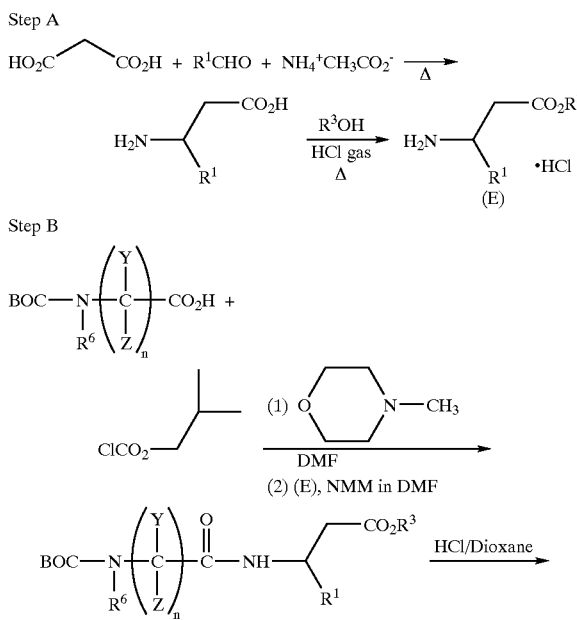

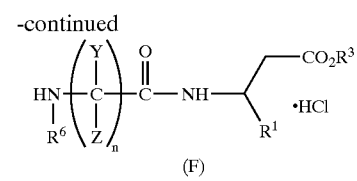

Scheme 7 illustrates methodology for preparing the gly-β-amino acid portion of the molecule (F) in a general manner.

Aldehydes (R'CHO) used in this methodology are either commercially available or can be prepared from commercially available reagents using methodologies for the preparation of aldehydes which are commonly known to those with ordinary skill in the art.

All other reagents are commercially available or can be readily synthesized by one skilled in the art.

Such methodologies and conditions can be further modified using conventional techniques to produce similar desired intermediates.

SCHEME 8

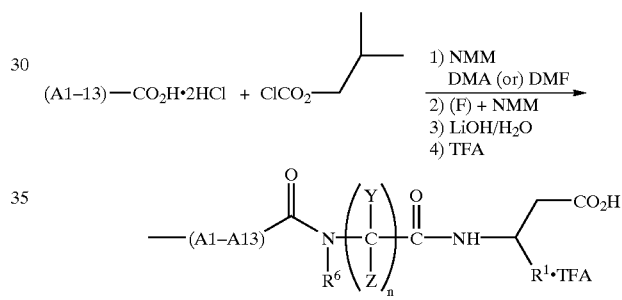

Scheme 8 illustrates methodology useful for coupling the heterocyclic acid portion (A1-13) to a gly-β-amino acid portion (F) to prepare compounds of the present invention.

The synthesis of A1-13 is illustrated in Schemes 1–4 and the synthesis of (F) is illustrated in Scheme 7.

Such methodology can be modified using conventional methods known to those with ordinary skill in the art.

Schemes 9–12 illustrate general methodology for preparing compounds of the present invention.

SCHEME 9

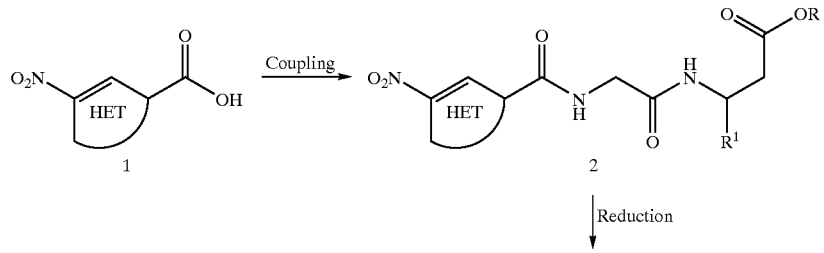

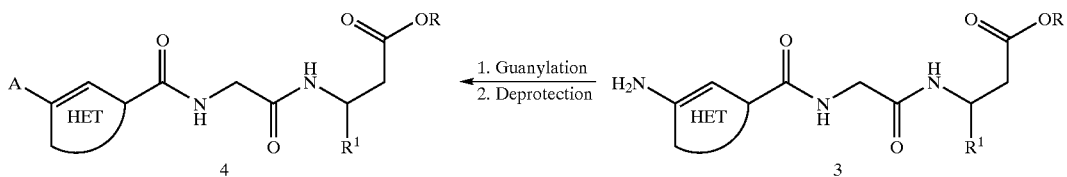

Scheme 9 illustrates the general methodology for the synthesis of the heterocycle derived gly-β-amino acid coupled target compounds. The reaction of the heterocyclic carboxylic acid with gly-β-amino acid under peptide coupling conditions gives the intermediate (2). Reduction of the nitro group using catalytic hydrogenation (e.g. Pt/C, $H_2$) gives the amino intermediate (3). This transformation may also be carried out chemically using $SnCl_2$. The amino group can be elaborated to guanidino or other functional groups of Formula I using the methodologies discussed above.

SCHEME 10

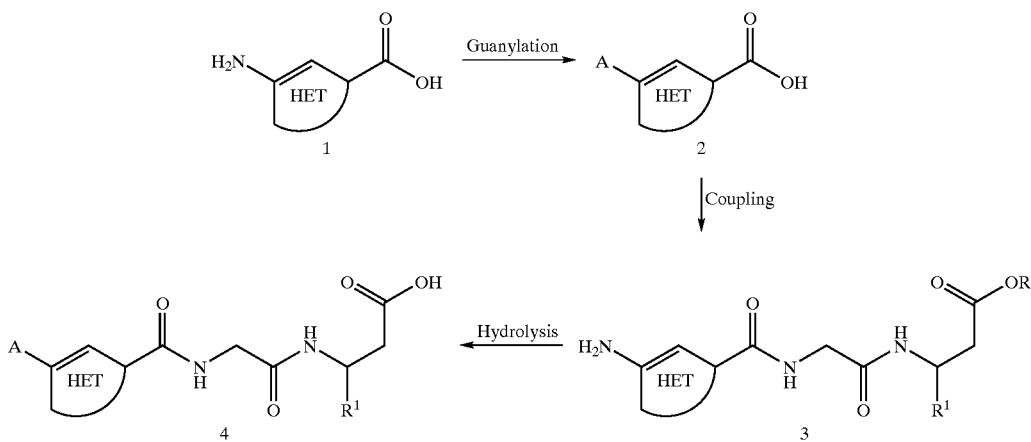

Alternatively, the target compounds may be synthesized by building the left hand portion of the molecule prior to coupling with the gly-β-amino acid (Scheme 10). The amino functionality of the heterocycle amine (1) is functionalized to the guanidine or other groups (A, Formula I) and then coupled to the gly-β-amino acid under standard coupling conditions.

SCHEME 11

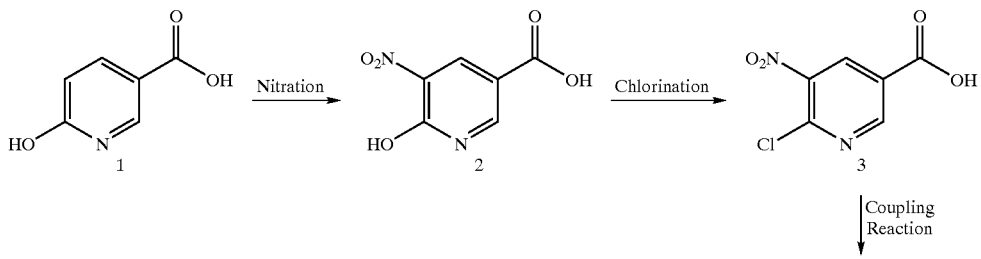

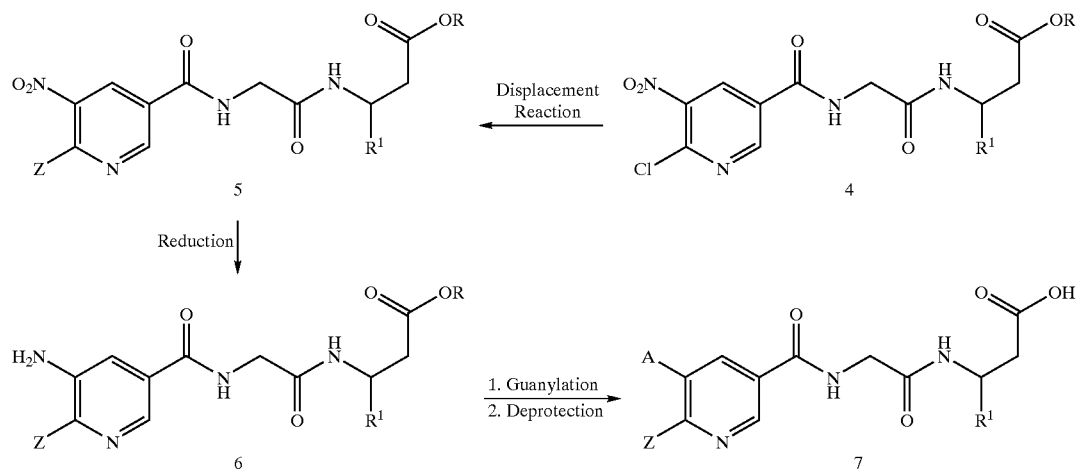

Scheme 11 shows a general synthesis of substituted pyridines and pyridone derived target compounds. Nitration of 6-hydroxynicotinic acid followed by chlorination gives 6-chloro-5-nitronicotinic acid. Coupling of the intermediate 3 with the gly-β-amino acid gives the product 4. The chloro group in versatile intermediate 4 can be readily displaced by a variety of nucleophiles to give 5. Reduction of the nitro group on 4 or 5 and further elaboration of the amino group as discussed in Scheme 9 gives the target compounds.

SCHEME 12

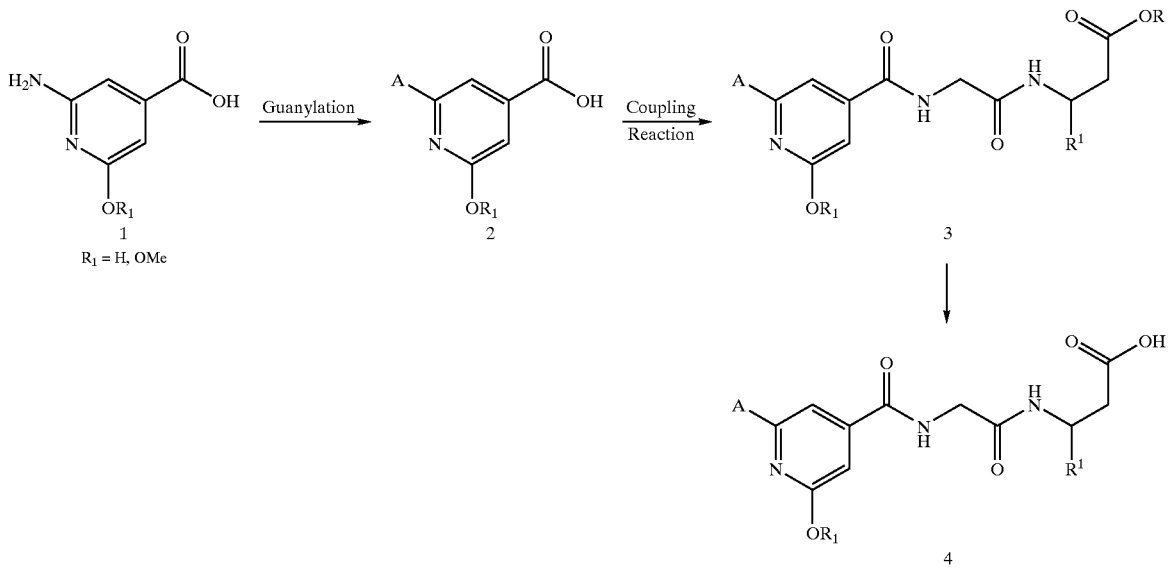

Scheme 12 shows the synthesis of substituted pyridine and pyridone derived target compounds starting with 2-amino-6-hydroxypridine-4-carboxylic acid. The starting material 1 used in the scheme may be prepared by reacting commercially available 2-chloro-6-methoxy-pyridine-4-carboxylic acid with ammonium hydroxide under high pressure conditions. Elaboration of the amino group followed by coupling to the gly-β-amino acid as discussed in Scheme 10 gives the target compounds.

SCHEME 13

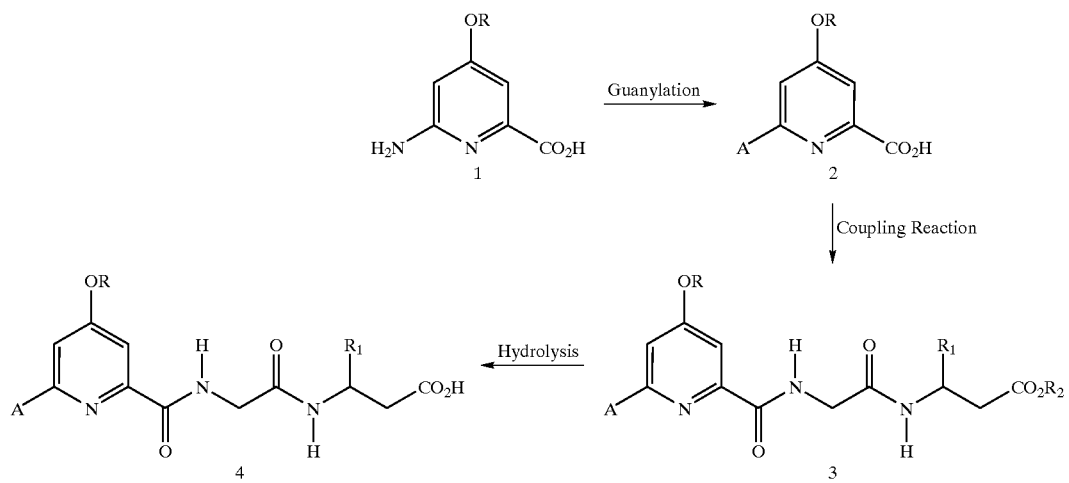

Scheme 13 shows the synthesis of isomeric pyridines and pyridones starting with 6-amino-4-methoxy-picolinic acid. The starting material 1 used in the Scheme 13 may be prepared as described in the literature (J. Am. Chem. Soc., 78, 4130, 1956). Functionalization of the amino group in 1 followed by coupling reaction and hydrolysis (as in Scheme 10) gives the target compounds.

The isomeric pyridine and pyridone derived compounds may be prepared using the methodology shown in Scheme 14. The key intermediate 4 may be prepared by starting with 6-chloro-picolinic acid. Oxidation followed by nitration gives the 4-nitropyridine derivative (3). Deoxygenation of the N-oxide, reduction of the nitro group and nucleophilic displacement of chloro group gives the intermediate 4. The

SCHEME 14

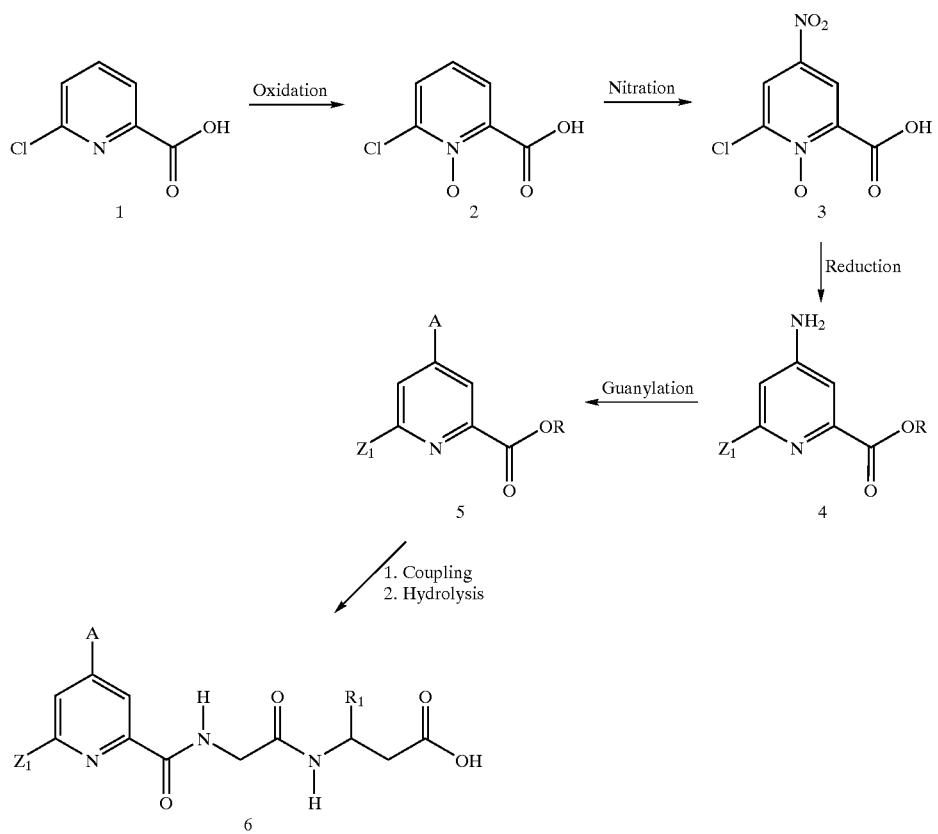

methodology discussed in Scheme 10 may be applied to achieve the synthesis of target compounds.

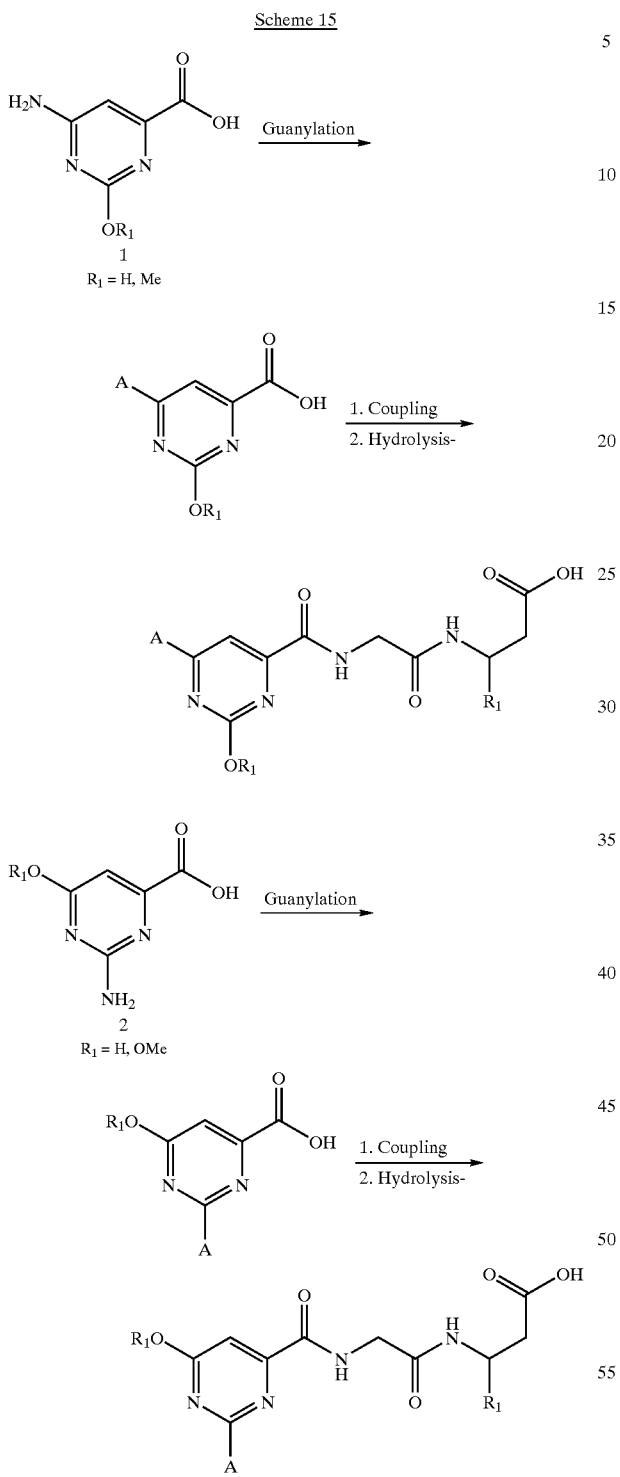

The methodology shown in Scheme 10 can also be used for the synthesis of pyrimidine derived target compounds (Scheme 15). The isomeric pyrimidine derivatives 1 and 2 may be synthesized by following the literature preparations (J. Org. Chem., 26, 2755, 1961).

EXAMPLE A

Preparation of

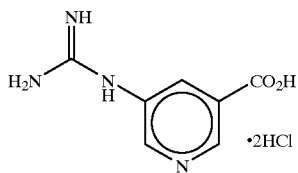

5-aminonicotinic acid (4.0 g, 0.021 mole) (Helv. Chim. Acta, 47, 363 (1964); JACS, 70, 2381 [1948]), 1 H-pyrazole-1-carboxamidine hydrochloride (4.6 g, 0.031 mole), diisopropylethylamine (8.0 g, 0.062 mole), dioxane (14 mL) and $H_2O$ (7 mL) were heated at reflux for 2 days. The reaction was cooled to room temperature, the precipitate was filtered, washed with $H_2O$/dioxane (50:50) and dried. The precipitate was slurried in $H_2O$ and made acidic with 2N HCl. The solvent was removed under vacuum to yield the above compound as a white solid (750 mg).

MS and $^1$H-NMR were consistent with the desired structure.

EXAMPLE B

Preparation of

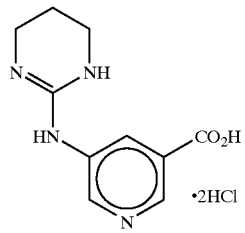

Step 1

To 3,4,5,6-tetrahydro-2-pyrimidine thiol (10 g, 0.086 mole) (Aldrich) in absolute ethanol (75 ml) is added MeI (12.2 g, 0.086 mole). The reaction was stirred at reflux for 2.5 hours. The solvent was removed under vacuum and the product dried to yield 2-methyl thio-3,4,5,6-tetrahydro-2-pyrimidine hydroiodide as a white solid (22 g).

MS and $^1$H-NMR were consistent with the desired structure.

Step 2

To the product from Step 1 above (5.3 g, 0.021 mole) and triethylamine (2.07 g, 0.021 mole) in $CH_2Cl_2$ (25 mL) was added BOC anhydride (4.5 g, 0.021 mole) at ice bath temperature. The reaction was then stirred at room temperature for 2 days. The $CH_2Cl_2$ was washed with $H_2O$ (3×), dried over $MgSO_4$, and removed under vacuum to yield N-Boc-2-methylthio-3,4,5,6-tetrahydro-2-pyrimidine (4.14 g).

MS and $^1$H-NMR were consistent with the desired structure.

Step 3

The product from Step 2 above (3.08 g, 0.0134 mole), 5-aminonicotinic acid (1.8 g, 0.0134 mole) in DMA (12 mL) was heated at 80–85° C. for 2 weeks. The reaction mixture was diluted with $CH_3CN$, the precipitate was filtered, washed with $CH_3CN$ and dried. The precipitate was slurried in $H_2O$ and the pH was lowered to 1–2 with concentrated HCl. The solution was frozen and lyopholized to yield the desired product as a light brown solid (1.2 g). MS and ¹H-NMR were consistent with the desired structure.

EXAMPLE C

Preparation of

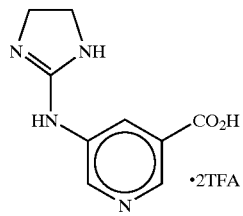

Step 1

To 2-methylthio-2-imidazoline hydroiodide (20 g, 0.082 mole) (Aldrich), and triethylamine (8.28 g, 0.082 mole) in CH$_2$Cl$_2$ (100 mL) was added BOC anhydride (17.9 g, 0.082 mole) at ice bath temperature. The reaction was stirred overnight at room temperature. The CH$_2$Cl$_2$ was washed with H$_2$O (2×), dried over MgSO$_4$ and removed under vacuum to yield N-BOC-2-methylthio-2-imidazoline as a viscous oil turned waxy white solid (15.93 g).

MS and ¹H-NMR were consistent with the desired structure.

Step 2

The product from Step 1 above (15.93 g, 0.0737 mole), 5-aminonicotinic acid (9.6 g, 0.07 mole), and triethylamine (7.1 g, 0.07 mole) in DMA (60 mL) was heated at 100° C. for 2 days, then at 130° C. for 1 day, and at 150° C. for 2 additional days. After cooling and diluting the reaction mixture with CH$_3$CN, the precipitate,was filtered, washed with ether and dried (zwitterion yield is 10.16 g). This was slurried in H$_2$O and made acidic with TFA (pH 1–2). The solution was frozen and lyophilized to yield the desired product as a light yellow solid (20.15 g).

MS and ¹H-NMR were consistent with the desired structure.

EXAMPLE D

Preparation of

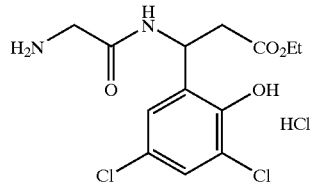

Step 1

Preparation of

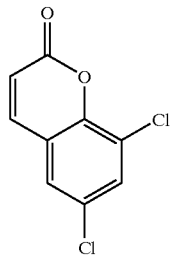

To a 2 L round bottom flask fitted with a mechanical stirrer and condenser was placed 3,5-dichlorosalicylaldehyde (200.0 g, 1.05 mol, 1 equivalent), acetic anhydride (356 g, 3.49 mol) and triethylamine (95.0 g, 0.94 mol, 0.90 equivalent). The reaction solution was heated at reflux overnight. The dark brown reaction mixture was cooled to 50° C. and water (1 L) added with stirring. After one hour the mixture was filtered and the filtrate combined with EtOH (1 L). This mixture was heated to 45° C. for one hour, cooled to room temperature, filtered and the solid (fraction A) washed with EtOH (0.5 L). The combined EtOH solutions were concentrated by rotary evaporation to produce an oil (fraction B). The solid from fraction A was dissolved in methylene chloride (1.5 L) and the resulting solution passed through a pad of silica gel (1300 mL volume). The resulting dark brown solution was concentrated to an oil that was triturated with hexanes (1.3 L) to give a solid that was isolated by filtration and washed (hexanes) to give substantially pure 6,8-dichlorocoumarin (163 g). An additional 31 g of product was obtained by treating the oil (fraction B) in a similar fashion; the oil was dissolved in methylene chloride (0.5 L) passed through a silica pad (0.5 L volume) and triturated with hexanes. The total isolated yield is 194 g or 86% of the brown solid.

MS and ¹H-NMR were consistent with the desired product.

Step 2

Preparation of

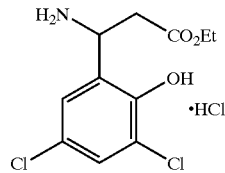

To a 3-neck 2 L round bottom flask fitted with a mechanical stirrer was placed 6,8-dichlorocoumarin (160 g, 0.74 mol) prepared in Step 1 and dry THF (375 mL, Aldrich Sure Seal). The resulting mixture was cooled to −40° C. (dry ice-acetone bath) and lithium bis(trimethylsilyl)amide (0.80 mol, 800 mL of 1M in THF) added while maintaining the temperature below −40° C. Upon completion of the addition the cooling bath was removed. After 0.5 hour the mixture was warmed to −5° C. The reaction was quenched by addition of a solution of HCl (0.5 L of 4M in dioxane) in EtOH (1.25 L). The temperature was maintained below 0° C. overnight. The reaction mixture was concentrated to about one-half its original volume and partitioned between EtOAc (3 L) and water (2 L). The organic layer was washed with aqueous HCl (3×1 L, 0.5 N HCl). The pH of the combined water layers was adjusted to about 7 by addition of 10% aqueous NaOH and extracted with methylene chloride (3×2

L). The combined organic layers were dried (MgSO$_4$), filtered, and HCl (210 mL of 4M in dioxane) added with stirring. Upon completion of precipitation the solid was removed by filtration. The filtrate was concentrated to a small volume and methyl t-butyl ether added. The solid obtained was combined with the initially formed solid and the combined product was washed with methyl t-butyl ether, isolated by filtration and dried (vacuum oven over a weekend) to obtain the desired product (172 g, 74% yield).

MS and $^1$H-NMR were consistent with the desired product.

Step 3

Preparation of

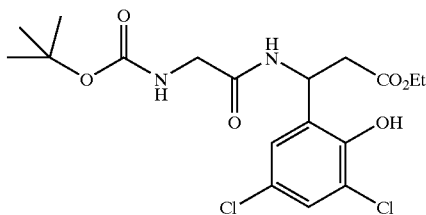

To a flame-dried round bottom flask (0.5 L) equipped with magnetic stir bar was added N-t-Boc-glycine N-hydroxysuccinimide ester (Sigma, 15.0 g, 0.055 mol), dry DMF (Aldrich Sure Seal, 200 mL) and the product from Step 2 (21.67 g, 0.055 mol) under an inert atmosphere (Ar). The reaction mixture was cooled to approximately 0° C. (salt-ice bath) and N-methyl morpholine (5.58 g, 0.056 mole) and a catalytic amount of DMAP added. The reaction was allowed to proceed overnight. The reaction mixture was concentrated to a slush, and partitioned between EtOAc (0.4 L) and aqueous base (2×0.2 L, aqueous saturated NaHCO$_3$). The organic layer was washed consecutively with aqueous citric acid (2×0.2 L, 10% w/v), with aqueous sodium bicarbonate (2×0.2 L), brine and dried (Na$_2$SO$_4$). Volatiles were removed under vacuum at 55° C. to give an oil (22.5 g, 92% yield) that solidified on standing.

MS and $^1$H-NMR were consistent with the desired product.

Step 4

Preparation of

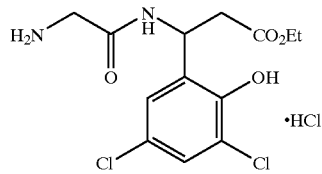

The product obtained in Step 3 was deprotected to give the amine hydrochloride salt using the following procedure. To the product obtained in Step 3 (14.0 g, 0.032 mole) in a flame-dried round bottom flask (0.1 L) with stir bar was added dry dioxane (40 mL). To this solution was added HCl (4.0 N in dioxane, 2 equivalents, 6.32 mL) at 0° C. The reaction was allowed to proceed until gas evolution ceased and the reaction was complete. Volatiles were removed under vacuum and the residue triturated with diethyl ether (50 mL). Solids were collected by filtration, washed with ether and dried to give the desired product (12.5 g).

MS and $^1$H-NMR were consistent with the desired product.

EXAMPLE E

Preparation of

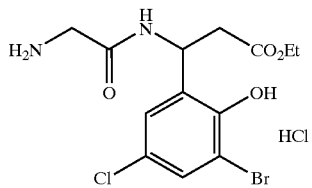

Step 1

Preparation of

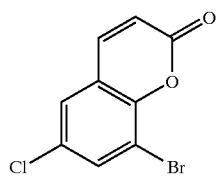

To a suspension of 3-bromo-5-chlorosalicylaldehyde (175 g, 743.2 mmol) in acetic anhydride (280.5 mL, 3 mol) was added triethylamine (103.6 mL, 743.2 mmol). The reaction solution was heated at reflux for 4.5 hours. The solution was cooled and concentrated in vacuo. The brown residue was added to absolute ethanol (730 mL). The mixture was stored at 0° C. for 14 hours. The brown solid was collected by filtration and washed with cold ethanol. The solid was dried in vacuo to give the desired product (123 g, 64% yield). $^1$H-NMR was consistent with the proposed structure.

Step 2

Preparation of

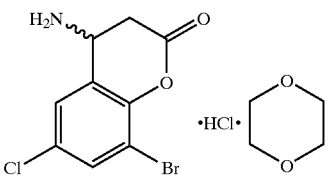

To a suspension of the coumarin produced in Step 1 (40.0 g, 154.1 mmol) in THF (400 mL) at −76° C. was added dropwise with stirring lithium bis(trimethylsilyl)amide (154.1 mL of a 1M solution in THF). The addition was completed in 10 minutes. The reaction mixture was then stirred for 5 minutes, warmed to −20° C. and stirred for 15 minutes. To this solution was added acetic acid (9.25 g, 154.1 mmol) in THF (28 mL) over 5 minutes. The mixture was warmed to room temperature and volatiles were removed in vacuo. The residue was dissolved in ether (850 mL), washed with saturated aqueous NaHCO$_3$ (2×100 mL), brine (2×40 mL) and dried (MgSO$_4$). The ether solution was concentrated to about 160 mL, and cooled to 0° C. To this suspension was added HCl (4 M in dioxane, 56.3 mL, 225 mmol) and the mixture was stirred at 0° C. for 30 minutes. The suspension was filtered and the filter cake exhaustively washed with ether. The solid was dried in vacuo to give the desired product as the HCl salt, dioxane solvate (45 g). $^1$H-NMR was consistent with the proposed structure.

Step 3
Preparation of

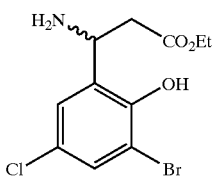

To a suspension of the lactone produced in Step 2 (142.2 g, 354.5 mmol) in absolute ethanol (533 mL) was added HCl (4M in dioxane, 157.8 mL, 631.1 mmol) over 10 minutes. The reaction mixture was stirred at room temperature for 2.5 hours. Volatiles were removed in vacuo. The residue was dissolved in ethyl acetate (450 mL) and the solution kept at 0° C. for 15 hours. The tan precipitate was collected by filtration and washed with cold ethyl acetate. The solid was dried in vacuo to give the desired product as the hydrochloride salt (100.4 g, 79% yield). $^1$H-NMR was consistent with the proposed structure.

Step 4
Preparation of

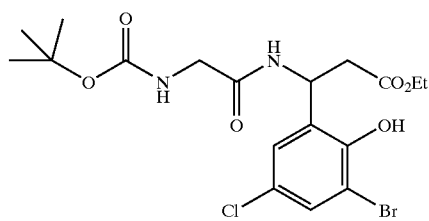

To a flame-dried round bottom flask (0.1 L) equipped with magentic stir bar was added N-t-Boc-glycine N-hydroxysuccinimide ester (Sigma, 2.72 g, 0.010 mol), dry THF (Aldrich Sure Seal, 50 mL) and the product of Step 3 (3.10 g, 0.01 mole, vacuum desiccated overnight over $P_2O_5$) under an inert atmosphere (Ar). The reaction mixture was cooled to approximately 0° C. (salt-ice bath) and triethylamine (1.01 g, 0.010 mole) was added. The reaction was allowed to proceed overnight. The reaction mixture was concentrated to a semi-solid and worked up in a fashion similar to Example A, Step 3. Volatiles were removed from the organic layer under vacuum at 55° C. to give an oil (4.0 g, 83% yield) that solidified on standing.

MS and $^1$H-NMR were consistent with the desired product.

Step 5
Preparation of

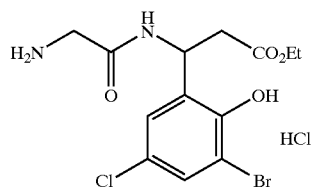

The product obtained in Step 4 was deprotected to give the hydrochloride salt using the following procedure. To the product obtained in Step 4 (4.0 g, 0.0084 mole) in a flame-dried round bottom flask (0.1 L) with stir bar was added dry dioxane (20 mL). To this was added HCl (4N in dioxane, 20 mL) and the reaction allowed to proceed until gas evolution ceased and the reaction was complete (about 1 hour). Volatiles were removed under vacuum and the residue triturated with diethyl ether (50 mL). Solids were collected by filtration, washed with ether and dried to give a light brown solid (2.7 g, 78% yield).

MS and $^1$H-NMR were consistent with the desired product.

EXAMPLE F

Preparation of

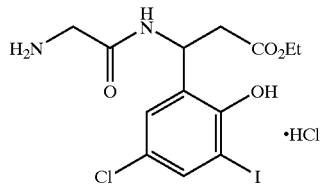

Step 1
Preparation of 3-iodo-5-chlorosalicylaldehyde

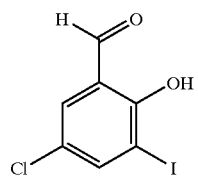

N-Iodosuccinimide (144.0 g, 0.641 mole) was added to a solution of 5-chlorosalicylaldehyde (100 g, 0.638 mole) in dimethylformamide (400 mL). The reaction mixture was stirred for 2 days at room temperature. Additional N-iodosuccinimide (20.0 g) was added and the stirring was continued for additional 2 days. The reaction mixture was diluted with ethyl acetate (1 L), washed with hydrochloric acid (300 mL, 0.1 N), water (300 mL), sodium thiosulfate (5%, 300 mL), brine (300 mL), dried ($MgSO_4$) and was concentrated to dryness to afford the desired aldehyde as a pale yellow solid (162 g, 90% yield).

$^1$H-NMR and MS were consistent with the desired product.

Step 2
Preparation of 6-chloro-8-iodocoumarin

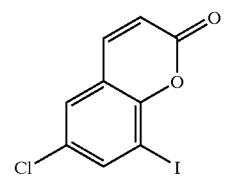

A mixture of 3-iodo-5-chlorosalicylaldehyde (100 g, 0.354 mole), acetic anhydride (300 mL) and triethylamine (54 mL) was heated at reflux for 18 hours. Upon cooling, the desired coumarin precipitated as a dark brown crystalline material. The precipitate was filtered, washed with hexane/ethyl acetate (4:1, 200 mL), and air dried. [Yield: 60 g (55% yield)]. Additional quantities of the desired product (10 g, 9% yield) can be obtained from the filtrate, upon storage.

$^1$H-NMR and MS indicated this to be the desired product.

Step 3

Preparation of (R,S)-4-amino-3,4-dihydro-6-chloro-8-iodocoumarin hydrochloride

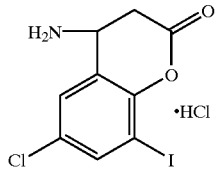

Lithium hexamethyldisilazane (21.62 mL, 1M, 21.62 mmol) was added to a solution of 6-chloro-8-iodocoumarin (6.63 g, 21.62 mmol) in tetrahydrofuran (100 mL) at −78° C. The reaction mixture was stirred at this temperature for 30 minutes, then at 0° C. for 1 hour. Acetic acid (1.3 g, 21.62 mmol) was added to the reaction mixture. The reaction mixture was poured into an ethyl acetate (300 mL) and saturated sodium carbonate (200 mL) solution. The organic layer was separated, washed with brine (200 mL) followed by dioxane/HCl (4N, 30 mL) at 0° C. The reaction mixture was stirred for 1 hour at room temperature, filtered, and was dried in vacuo to afford the desired product as a powder (4.6 g, 59% yield). (rphplc: Rf 6.8 minutes; Gradient 10% acetonitrile–90% acetonitrile over 15 minutes then to 100% acetonitrile over the next 6 minutes. Both water and acetonitrile contain 0.1% TFA. Vydac C18 protein peptide column, 2 mL/min flow rate, monitored at 254 nm).

$^1$H-NMR and MS were consistent with the desired product.

Step 4

Preparation of (R,S)-ethyl 3-amino-3-(5-chloro-2-hydroxy-3-iodo)phenyl propionate hydrochloride

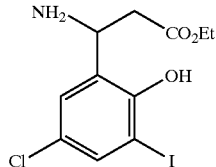

Hydrogen chloride gas was bubbled into a solution of 4-amino-3,4-dihydro-6-chloro-8-iodocoumarin hydrochloride (22.0 g, 61.09 mmol) in ethanol (250 mL) keeping the reaction mixture at 0–10° C. until saturation. After 6 hours at reflux, most of the solvent was removed by distillation. The cooled residue was added to anhydrous ether and was stirred for 2 hours. The initial gum turned in to a crystalline material. The crystalline product was filtered and was dried to afford the desired product as an off-white crystalline powder (20 g, 81% yield). (Rf. 7.52 min, conditions as Step 3).

$^1$H-NMR and MS were consistent with the desired product.

Step 5

Preparation of (R,S)-ethyl 3-(N-BOC-gly)amino-3-(5-chloro-2-hydroxy-3-iodo)phenyl propionate A mixture of BOC-gly (2.16 g, 12.31 mmol), HOBT (1.67 g, 12.31), EDCl (2.36 g, 12.31 mmol) and DMF (50 mL) was stirred at 0° C. for 1 hour. Ethyl 3-amino-3-(5-chloro-2-hydroxy-3-iodo)propionate hydrochloride (5.0 g, 12.31 mmol) was added to the reaction mixture followed by triethylamine (3.5 mL). The reaction mixture was stirred for 18 hours at room temperature. DMF was removed in vacuo and the residue was partitioned between ethyl acetate (300 mL) and sodium bicarbonate (200 mL). The organic layer was washed with hydrochloric acid (1N, 100 mL), brine (200 mL), dried (MgSO$_4$) and was concentrated to afford the desired product as a solid (6 g, 93% yield).

$^1$H-NMR and MS were consistent with the desired product.

Step 6

Preparation of (R,S)-ethyl 3-(N-gly)-amino-3-(5-chloro-2-hydroxy-3-iodo)phenyl propionate hydrochloride Dioxane/HCl (4N, 20 mL) was added to ethyl 3-(N-BOC-gly)-amino-3-(5-chloro-2-hydroxy-3-iodo)propionate (6.0 g, 11.30 mmol) at 0° C. and was stirred at room temperature for 3 hours. The reaction mixture was concentrated, and concentrated once more after addition of toluene (100 mL). The residue obtained was suspended in ether, was filtered and dried to afford the desired product as a crystalline powder (5.0 g, 95% yield). (rphplc: Rf 8.3 min. conditions as Step 3).

$^1$H-NMR and MS were consistent with the desired product.

EXAMPLE G

Preparation of

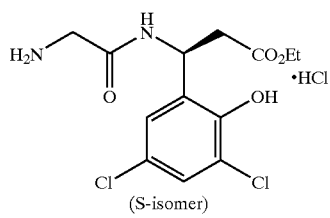

(S-isomer)

Step 1

Preparation of Reformatski Reagent

BrZnCH$_2$CO$_2$-t-Bu

A 4-L flask fitted with a condenser, temperature probe and mechanical stirrer was charged with Zn metal (180.0 g, 2.76 mol, 30–100 mesh) and THF (1.25 L). While stirring 1,2-dibromoethane (4.74 mL, 0.06 mol) was added via syringe [alternatively, TMS Cl (0.1 eq.) at room temperature for one hour may be substituted]. After inert gas purge (3N$_2$/vacuum cycles) the suspension of zinc in THF was heated to reflux (65° C.) and maintained at this temperature for 1 hour. The mixture was cooled to 50° C. before charging tert-butyl bromoacetate (488 g, 369 mL, 2.5 mol) via 50 mL syringe and syringe pump (delivery set to 4.1 mL/min) over 1.5 hours. Reaction temperature of 50°+/−50° C. was maintained throughout the addition. The reaction mixture was allowed to stir at 50° C. for one hour after the addition was complete. Subsequently, the mixture was allowed to cool to 25° C. and the precipitated product allowed to settle. The THF mother liquor is decanted into a 2-L round bottom flask using a coarse fritted filter stick and partial vacuum transfer (20 mm Hg). This removed about 65% of the THF from the mixture. 1-Methyl-2-pyrrolidinone (NMP, 800 mL) was added and agitation resumed for 5 minutes. The reaction mixture can be filtered to remove any remaining zinc. Analysis indicated a titer of desired Reformatski reagent of 1.57 M with a molar yield of 94%. Alternatively, the solid reagent can be isolated by filtration from the original reaction mixture. The cake was washed with THF until a white solid was obtained and dried under N$_2$ to obtain the desired product as a mono THF solvate that may be stored at −20° C. (desicated) for extended periods. Typical recoveries are 85–90%.

Step 2

A. Preparation of

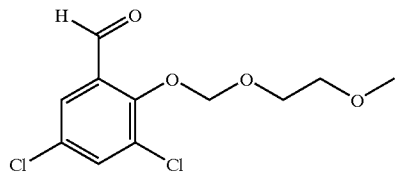

Potassium carbonate (powder, oven dried at 100° C. under vacuum, 8.82 g, 60 mmoles) was added to a solution of 3,5-dichlorosalicylaldehyde (11.46 g, 60 moles) in DMF (40 mL) at room temperature to give a bright yellow slurry. MEMCl (neat, 7.64 g, 61 mmoles) was then added while maintaining the bath temperature at 20° C. The mixture was stirred at 22° C. for 6 hours and MEMCl (0.3 g, 2.4 mmoles) was added. The mixture was stirred for another 0.5 hour and the reaction mixture poured into cold water (200 mL) to precipitate the product. The slurry was filtered on a pressure filter and the cake was washed with water (2×50 mL) and dried under N$_2$/vacuum to afford the product as an off white solid (14.94 g, 89% yield). $^1$H-NMR (CDCl$_3$, TMS) 3.37 (s, 3H), 3.54 to 3.56 (m, 2H), 3.91 to 3.93 (m, 2H), 5.30 (s, 2H), 7.63 (d, 1H), 7.73 (d, 1H), 10.30 (s, 1H); $^{13}$C NMR (CDCl$_3$, TMS) δ (ppm):59.03, 70.11, 99.57, 126.60, 129.57, 130.81, 132.07, 135.36, 154.66, 188.30. DSC: 48.24° C. (endo 90.51 J/g).

Microanalytical: calculated for $C_{11}H_{12}Cl_2O_4$: C, 47.33%; H, 4.33%; Cl, 25.40% Found: C, 47.15%; H, 4.26%; Cl, 25.16%.

B. Preparation of

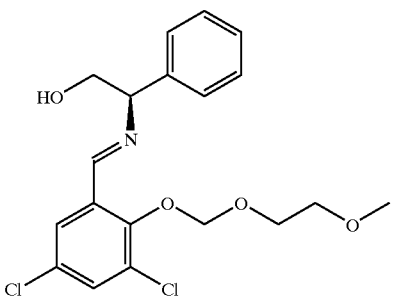

The product from Step 2A (35.0 g, 0.125 mol) was charged in a 1-L 3-neck round bottom flask fitted with a mechanical stirrer and an addition funnel followed by addition of THF (200 mL). The solution was stirred at 22° C. and (S)-phenylglycinol (17.20 g, 0.125 mol) was added at once. After 30 minutes at 22° C., MgSO$_4$ (20 g) was added. The mixture was stirred for 1 hour at 22° C., and filtered on a coarse fritted filter. The filtrate was concentrated under reduced pressure. No further purification was performed and the crude imine was used directly in the coupling reaction, Step 2, C.

C. Preparation of

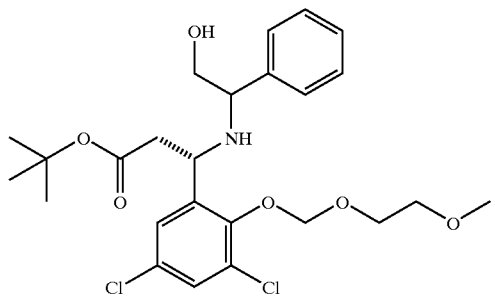

A 1-L 3-neck round bottom flask fitted with a mechanical stirrer and an addition funnel was charged with solid reagent from Step 1 (91.3 g, 0.275 mol) and NMP (200 mL) under nitrogen. The solution was then cooled to −10° C. and stirred at 350 rpm. A solution of imine (prepared in Step B) in NMP was prepared under nitrogen and then added over 20 minutes to the above reaction mixture while the temperature was maintained at −5° C. (jacket temperature −10° C.). The mixture was stirred for an additional 1.5 hours at −8° C. and one hour at −5° C. after the addition was complete. After cooling to −10° C. a mixture of concentrated HCl/saturated solution of NH$_4$Cl (100 mL), water (100 mL) and brine (100 mL) was added to the solution. MTBE (200 ml) was added and the mixture was stirred for 15 minutes at 23° C. at 200 rpm. Stirring was stopped and the layers separated. The aqueous layer was extracted with MTBE (100 ml). The two organic layers were combined, washed successively with a saturated solution of NH$_4$Cl (100 ml), water (100 ml), and brine (100 ml). The solution was dried with MgSO$_4$ (30 g), filtered and concentrated to afford an orange oil (66.3 g) (solidifies in standing) containing the desired product as a single diastereoisomer as determined by proton and carbon nmr. A sample was purified for analysis by recrystallization from heptane to afford the product as an off-white solid. Proton and carbon nmr and IR spectra were consistent with the desired product. $[\alpha]^D_{25}$=+8.70° (c=1.057, MeOH).

Microanalytical: calculated for $C_{25}H_{33}Cl_2NO_6$: C, 58.77%; H, 6.47%; N, 2.72%; Cl, 13.78%. Found: C, 58.22%; H, 6.54%; N, 2.70%; Cl, 13.66%.

Step 3
Preparation of

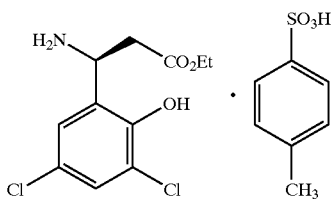

A.

A solution of crude ester prepared in Step 2 [17.40 g, 0.033 mole (theory)], and EtOH (250 mL) was charged to a 1-L 3-neck jacketed reactor. The solution was cooled to 0° C. and Pb(OAc)$_4$ (14.63 g, 0.033 mole) was added at once. After 2 hours a 15% solution of NaOH (30 mL) was added and ethanol was removed under reduced pressure. Another portion of 15% NaOH (100 mL) was added and the mixture extracted with MTBE (2×100 mL), washed with H$_2$O (2×100 mL) and brine (50 mL), dried with Na$_2$SO$_4$, filtered on celite and concentrated under reduced pressure to afford an orange oil (12.46 g) which was homogeneous as determined by tlc. The oil was used without further purification.

B.

The oil from A, was diluted with EtOH (30 mL) and paratoluene sulfonic acid (1.3 eq., 0.043 mole, 8.18 g) was added. The solution was heated to reflux for 8 hours, cooled to ambient temperature and concentrated under reduced pressure. The residue was treated with THF (20 mL) and heated to reflux to form a solution. The solution was cooled to room temperature and the compound crystallized. Heptane (30 mL) and THF (10 mL) were added to form a fluid slurry which was filtered. The cake was washed with THF/heptane (40 mL, 1/1) and vacuum dried for two hours in a pressure filter under nitrogen to afford a white solid (7.40 g).

Proton and carbon NMR and IR spectra were consistent with the desired product as substantially a single enantiomer.

Microanalytical: calculated for C$_{18}$H$_{21}$Cl$_2$NO$_6$S, 0.25 C$_4$H$_8$O: C, 48.73%; H, 4.95%; N, 2.99%; Cl, 15.14%. Found: C, 48.91%; H, 4.95%; N, 2.90%; Cl, 14.95%.

Step 4
Preparation of

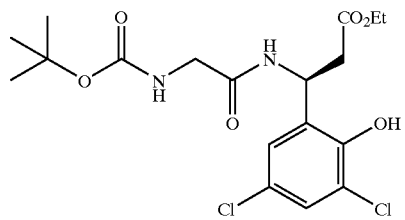

To a 500 mL round bottom flask equipped with a magnetic stir bar and nitrogen bubbler were charged the product from Step 3 (21.7 g, 0.065 mole), N-t-Boc-glycine N-hydroxysuccinimide ester (17.7 g, 0.065 mole) and DMF (200 mL). The reaction mixture was stirred under nitrogen at room temperature for 3.25 hours and a pale orange solution formed. The reaction mixture was poured into ice-cold ethyl acetate (1.2 L). The organic solution was washed with 1 M HCl (250 mL) and then with brine (500 Ml), dried (MgSO$_4$) and concentrated under vacuum to near dryness to obtain an oil that was subsequently dried at 50° C. to obtain the product as a colorless oil (28.12 g, 99% yield). Seed crystals were prepared from ethyl acetate/ hexanes. The product (about 28 g) was dissolved in ethyl acetate (35 mL) and hexanes (125 mL). The solution was seeded with the seed crystals and precipitate formed. The solids were filtered and dried overnight under vacuum at 55° C. to yield a colorless solid (27.0 g, 95% yield). $^1$H-NMR was consistent with the desired product.

Step 5
Preparation of

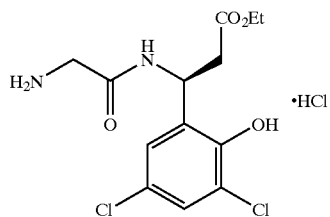

The Boc-protected glycine amide prepared in Step 4 (27.0 g, 0.062 mole) was dried overnight over P$_2$O$_5$ and NaOH pellets. The solid was dissolved in dioxane (40 mL) and the solution cooled to 0° C. An equivalent volume of 4N HCl/dioxane (0.062 mole) was added and the reaction was run for 2 hours. At this point the conversion was 80% as determined by rphplc. The reaction mixture was allowed to warm to room temperature over 4 hours. The reaction mixture was concentrated at 40° C. to a foam which was triturated with ether (200 mL). The white solid that formed was filtered and dried over P2O$_5$ to yield the desired glycine beta-amino acid ethyl ester compound as the HCl salt (20.4%, 88.5% isolated yield. $^1$H-NMR and MS were consistent with the structure.

EXAMPLE H

Preparation of

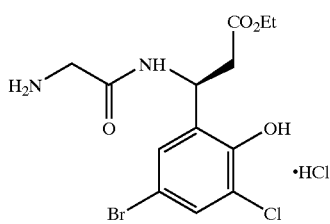

Step 1
Preparation of

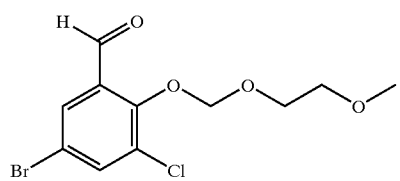

Potassium carbonate (powder, oven dried at 100° C. under vacuum, 22.1 g, 0.16 moles) was added to a solution of 3-chloro-5-bromosalicylaldehyde (35 g, 0.15 moles) in DMF (175 ml) at room temperature to give a bright yellow slurry. MEMCl (neat, 25.0 g, 0.2 moles) was then added while maintaining the bath temperature at 20° C. The mixture was then stirred at 22° C. for 6 hours and was poured into Dl water (1200 mL) to precipitate the product. The slurry was filtered on a pressure filter, the cake washed with Dl water (2×400 mL) and dried under N$_2$/vacuum to afford the product as an off-white solid (46 g, 95% yield). ¹H-NMR (CDCl₃, TMS) 3.35 (s, 3H), 3.54 to 3.56 (m, 2H), 3.91 to 3.93 (m, 2H), 5.30 (s, 2H), 7.77 (d, 1H), 7.85 (d, 1H), 10.30 (s, 1H); ¹³C NMR (CDCl₃, TMS) (ppm):59.05, 70.11, 71.49, 99.50, 117.93, 129.69, 129.78, 132.37, 138.14, 155.12, 188.22. DSC: 48.24° C. (endo 90.51 J/g);

Microanalytical: calculated for $C_{11}H_{12}BrClO_4$: C, 40.82%; H, 3.74%; Cl, 10.95%; Br, 24.69%. Found: C, 40.64%; H, 3.48%; Cl, 10.99%; Br, 24.67%.

Step 2
Preparation of

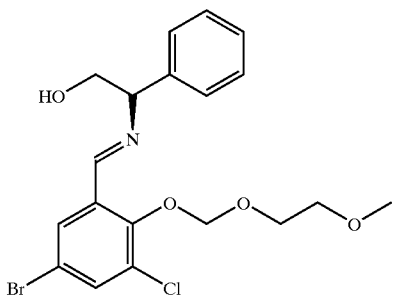

The product obtained in Step 1 (32.35 g, 0.1 mol) was charged in a 500 ml 3N round bottom flask fitted with a mechanical stirrer, followed by the addition of THF (160 ml) and (S)-phenylglycinol (13.71 g, 0.1 mol). After 30 minutes at 22° C., MgSO₄ (20 g) was added. The mixture was stirred for 1 hour at 22° C. and filtered on a coarse fritted filter. The filtrate was concentrated under reduced pressure to afford a pale yellow oil (48.0 g) containing the imine. No further purification was performed and the crude product was used directly in the coupling reaction.

Microanalytical: calculated for $C_{19}H_{21}BrClNO_4$: C, 51.54%; H, 4.78%; N, 3.16%; Br, 18.04%; Cl, 8.00%. Found: C, 51.52%; H, 5.02%; N, 2.82%; Br, 16.31%; Cl, 7.61%.

Step 3
Preparation of

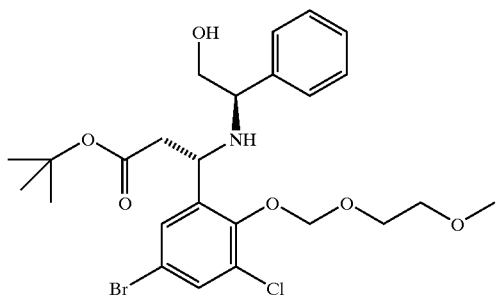

In a 5 L 3N round bottom flask fitted with a mechanical stirrer, reagent from Step 1 of Example G (332 g, 0.8 mol) was taken in NMP (660 mL) under nitrogen. The solution was then cooled to −10° C. A solution of imine produced in Step 2 in NMP (320 ml) was prepared under nitrogen and then added in 30 minutes to the above reaction mixture while the temperature was maintained at −5° C. The mixture was stirred for an additional hour and then cooled to −10° C. A mixture of concentrated HCl/saturated solution of NH₄Cl (30 mL/720 mL) was added over 10 minutes. MTBE (760 ml) was added and the mixture was stirred for 1 hour at 23° C. Stirring was stopped and the layers were separated. The aqueous layer was extracted with MTBE (320 ml). The two organic layers were combined, washed successively with a saturated solution of NH₄Cl (320 ml), Dl water (320 ml) and brine (320 ml). The solution was dried with MgSO₄ (60 g), filtered and concentrated to afford a yellow oil (228 g) containing the desired product as a single diastereoisomer. DSC: 227.54° C. (endo. 61.63 J/g);

Microanalytical: calculated for $C_{25}H_{33}BrClNO_6$: C, 53.72%; H, 5.95%; N, 2.50%; Br, 14.29%; Cl, 6.33%. Found: C, 53.80%; H, 6.45%; N, 2.23%; Br, 12.85%; Cl, 6.12%.

Step 4
Preparation of

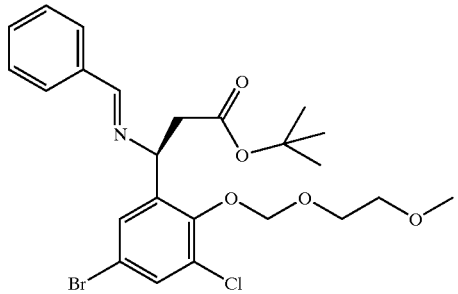

A solution of crude ester from Step 3 (~111 g) in ethanol (1500 mL) was charged under nitrogen atmosphere to a 3 L 3N round bottom flask fitted with a mechanical stirrer. The reaction mixture was cooled to 0° C. and lead tetraacetate (88.67 g, 0.2 mol) was added in one portion. The reaction mixture was stirred for 3 hours at 0° C. and then 15% aqueous NaOH (150 mL) was added to the reaction mixture below 5° C. Ethanol was removed under reduced pressure on rotavap. Another 15% aqueous NaOH (600 mL) was added and the reaction mixture was extracted with ethyl acetate (2×300 mL), MTBE (2×200 mL) and ethyl acetate (2×200 mL). The organic layers were combined and washed with Dl water (2×200 mL) and brine (2×100 mL) and dried over anhydrous MgSO₄ (30 g). The solution was then filtered over celite and concentrated under reduced pressure to give the product as an orange oil (96 g) that was used in the next step without further purification.

DSC: 233.60° C. (endo. 67.85 J/g);

Microanalytical: calculated for $C_{24}H_{21}BrClNO_5$: C, 54.71%; H, 5.54%; N, 2.65%; Br, 15.16%; Cl, 6.72. Found: C, 52.12%; H, 5.40%; N, 2.47%; Br, 14.77%; Cl, 6.48.

Step 5
Preparation of

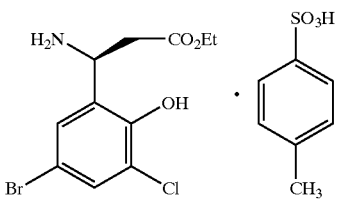

The crude product from Step 4 (~94 g) was taken up in absolute ethanol (180 mL) and para toluenesulfonic acid monohydrate (50.0 g, 0.26 mol) was added. The reaction mixture was then heated to reflux for 8 hours after which the solvent was removed under reduced pressure. Residual solid was taken up in THF (100 mL) and THF was then stripped off under reduced pressure. The residue was dissolved in ethyl acetate (500 mL) and cooled to −5° C. The resulting solid was filtered and washed with heptane (2×50 m) to give a white solid. The solid was air dried to give the product as a white solid (38 g) as a single isomer. $^1$H-NMR (DMSO, TMS) (ppm) 1.12 (t, 3H), 2.29 (s, 3H), 3.0 (m, 2H), 4.05 (q, 2H), 4.88 (t,1H), 7.11 (d, 2H), 7.48 (d, 2H), 7.55 (d, 1H), 7.68 (1H, d), 8.35 (br, s, 3H); $^{13}$C NMR (DMSO, TMS) (ppm): 13.82, 20.75, 37.13, 45.59, 60.59, 110.53, 122.47, 125.44, 127.87, 128.06, 129.51, 131.95, 137.77, 145.33, 150.14, 168.98; DSC: 69.86° C. (end., 406.5 J/g), 165.72° C. (end. 62.27 J/g), 211.24° C. (exo. 20.56 J/g) $[\alpha]^D_{25}$=+4.2° (c=0.960, MeOH); IR (MIR)(cm−1) 2922, 1726, 1621, 1591, 1494, 1471, 1413, 1376, 1324, 1286, 1237, 1207;

Microanalytical: calculated for $C_{18}H_{21}BrClNO_6S$: C, 43.69%; H, 4.27%; N, 2.83%; Br, 16.15%; Cl, 7.16%; S, 6.48%. Found: C, 43.40%; H, 4.24%; N, 2.73%; Br, 16.40%; Cl, 7.20%; S, 6.54%.

Step 6
Preparation of

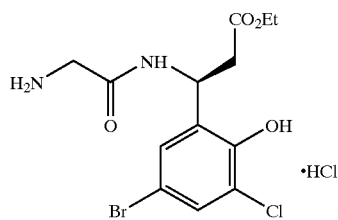

The above compound was prepared according to the procedures outlined in Example G, Step 4 and Step 5 where an equivalent quantity of the intermediate prepared in Step 5 as the free base was substituted for Example G, Step 4.

$^1$H-NMR and MS were consistent with the desired product.

EXAMPLE I
Preparation of

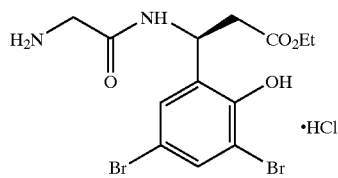

Step 1
Preparation of

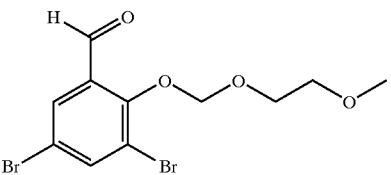

The above compound was prepared according to the methodology of Example G, Step 2A, substituting an equivalent quantity of 2-hydroxy-3,5-dibromobenzaldehyde for 3,5-dichlorosalicylaldehyde.

Yield: 88%; Pale yellow solid: m.p. 46–47° C.; $R_f$=0.6 (EtOAc/Hexane 1:1 v/v); $^1$H-NMR (CDCl$_3$) δ 3.37 (s, 3H), 3.56 (m, 2H), 3.92 (m, 2H), 5.29 (s, 2H), 7.91 (d, 1H, J=2.4 Hz), 7.94 (d, 1H, J=2.4 Hz), 10.27 (s, 1H); FAB-MS m/z 367 (M+) HR-MS calculated for $C_{11}H_{12}Br_2O_4$: 367.9083. Found: 367.9077.

$^1$H-NMR and MS were consistent with the desired compound.

Step 2

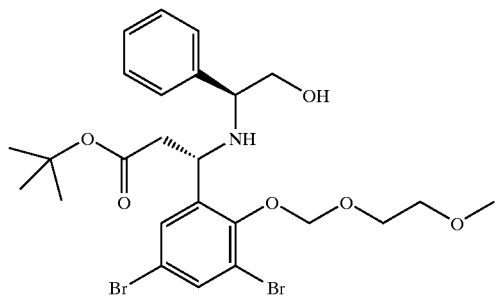

The above compound was prepared using the procedure of Example G, Steps 2B and 2C substituting an equivalent quantity of the compound from Step 1 in the procedure. Yield: 90%; Yellow solid; m.p. 57–59° C.; $R_f$=0.46 (EtOAc/Hexane 1:1 v/v); $^1$H-NMR (CDCl$_3$) δ 1.45 (s, 9H); 2.1 (br, 1H, exchangeable), 2.51 (d, 1H, $J_1$=9.9 Hz, $J_2$=15.3 Hz), 2.66 (d, 1H, $J_1$=4.2 Hz, $J_2$=15.3 Hz), 3.02 (br, 1H, exchangeable), 3.39 (s, 3H), 3.58–3.62 (m, 4H), 3.81 (m, 1H), 3.93 (m, 2H), 4.63 (dd, 1H, J=4.2 Hz), 5.15 (s, 2H), 7.17–7.25 (m, 6H), 7.49 (d, 1H): FAB-MS m/z 602 (M+H) HR-MS calculated for $C_{25}H_{34}NBr_2O_6$: 602.0753. Found: 602.0749.

$^1$H-NMR and MS were consistent with the desired compound.

Step 3
Preparation of

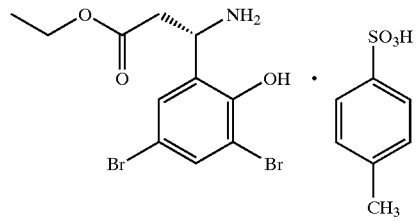

The above compound (p-toluenesulfonate salt) was prepared according to the methodology in Example G, Step 3 substituting an equivalent quantity of the product in Step 2 in Example G, Step 3A. Yield: 62%; white solid; $^1$H-NMR (DMSO-d$_6$) δ 1.09 (t, 3H, J=7.2 Hz), 2.27 (s, 3H), 2.97 (dd, 2H, $J_1$=3.0 Hz, $J_2$=7.2 Hz); 4.02 (q, 2H, J=7.2 Hz), 4.87 (t, 1H, J=7.2 Hz), 7.08 (d, 2H, J=4.8 Hz), 7.45 (m, 3H), 7.57 (d, 1H, J=2.4 Hz), 8.2 (br, 3H); FAB-MS m/z 365 (M+H) HR-MS calculated for $C_{11}H_{14}NBr_2O_3$: 365.9340. Found: 365.9311.

$^1$H-NMR and MS were consistent with the desired product.

Step 4
Preparation of

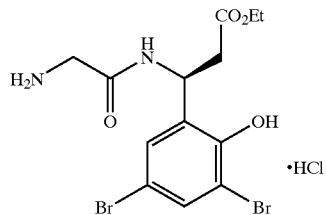

The above compound was prepared using the procedure of Example G, Step 4 and substituting the compound prepared in Step 3 to produce the BOC protected intermediate. The resulting BOC protected intermediate was converted to the desired compound using the procedure of Example G, Step 5.

$^1$H-NMR and MS were consistent with the desired compound.

EXAMPLE J

Preparation of ethyl β-[(2-aminoacetyl)amino]pyridine-3-propanoate, bis hydrochloride salt

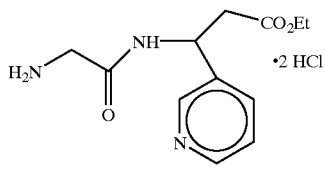

Step 1

To 3-pyridine carboxaldehyde (300 ml) in 2-propanol (3 liters) was added ammonium acetate (297 g) followed by malonic acid (398 g). The reaction mixture was stirred at reflux for 5 hours. The precipitate was filtered while hot and washed with hot isopropanol (2 liters). The resulting white solid was then dried to yield DL-3-amino-3-(3-pyridyl) propionic acid as a white solid (220 g).

NMR and MS were consistent with the desired product.

Step 2

DL-3-amino-3-(3-pyridyl)propionic acid (220 g) from Step 1 was slurried in absolute EtOH (3.6 liters). HCl gas (one lecture bottle -1lb) was bubbled into the reaction while stirring over 40 minutes. The slurry was then heated at reflux for 4 hours (a solution forms after 1 to 1.5 hours). The reaction mixture was cooled to 5° C. in an ice bath. After stirring at 5° C. for 1.5 hours, the resulting white precipitate was filtered and washed thoroughly with ether. After drying under vacuum at 50° C., the desired product, ethyl DL-3-amino-3-(3-pyridyl)propionate dihydrochloride was obtained as a white solid (331.3 g).

NMR and MS were consistent with the desired product.

Step 3

To ethyl DL-3-amino-3-(3-pyridyl)propionate dihydrochloride (220.6 g, 0.83 mole) from Step 2 in anhydrous THF (2 liters) and triethylamine (167.2 g, 1.65 moles), was added N-t-BOC-glycine N-hydroxysuccinimide ester (225 g, 0.826 moles) (Sigma) in several portions at 5–10° C. The reaction mixture was stirred overnight at room temperature. The resulting precipitate was filtered and washed with THF. The solvent from the filtrate was removed under vacuum. The residue was taken up in ethyl acetate (2.3 liters). The ethyl acetate layer was washed with saturated sodium bicarbonate (2×900 ml) and H$_2$O (3×900 ml), dried over MgSO$_4$ and removed under vacuum. The residue was slurried overnight in 10% ethyl acetate/hexane (2.5 liters). The precipitate was filtered, washed with 10% ethyl acetate/hexane (1 liter), then hexane, then dried to yield ethyl β-[[2-[[(1,1-dimethylethoxy)carbonyl]amino]acetyl]-amino]-pyridine-3-propanoate as a white solid (233 g).

NMR and MS were consistent with the desired product.

Step 4

Ethyl β-[[2-[[(1,1-dimethylethoxy)carbonyl]amino] acetyl]amino]-pyridine-3-propanoate (from Step 3) (232 g, 0.66 mole) was dissolved in warm dioxane (1 liter). After cooling to room temperature, 4M HCl in dioxane (1.6 liters) (Aldrich) was slowly added. A white precipitate formed after several minutes and then turned to a thick sticky material.

After 2 hours, the solvent was decanted off. The residue was slurried in ether and the ether decanted off until a white solid resulted. This was dried under vacuum to yield ethyl β-[(2-aminoacetyl)amino]pyridine-3-propanoate, bis hydrochloride salt as a white hygroscopic solid (224.2 g).

NMR and MS were consistent with the desired product.

EXAMPLE K

Preparation of 2-guanidino-4-carboxy thiazole hydrochloride

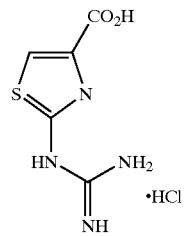

Step 1

To 2-imino-4-thiobiuret (11.1 g, 0.094 mole) (Aldrich) in absolute EtOH (100 mL) and at reflux was added ethyl bromopyruvate (20.0 g, 0.102 mole) (Aldrich) portionwise. The solution was stirred at reflux for 2 hours. Additional ethyl bromopyruvate (2.0 g) was added and the reaction continued at reflux for 2 more hours. The reaction was cooled to 10° C. and concentrated NH$_4$OH was added until pH=10. The resulting precipitate was filtered, washed with ether and dried to yield 2-guanidino-4-carboxyethylthiazole as a yellow solid (15.1 g).

MS and $^1$H-NMR were consistent with the desired structure.

Step 2

To the product of Step 1 (5.0 g, 0.023 mole) slurried in H$_2$O (100 mL) and ethanol (40 mL) was added NaOH (0.93 g, 0.023 mole). The solution was stirred overnight at room temperature. Additional ethanol (20 mL) and NaOH (0.93 g) were added to the reaction mixture and the solution was stirred at room temperature for 1 more hour. The pH was lowered to 7 with 1N HCl and the resultant precipitate was filtered, washed with H$_2$O and ether, then dried to yield the product (4.1 g) as the zwitterion.

The zwitterion was slurried in H$_2$O and acidified with concentrated HCl until solution. The solution was frozen and lyophilized to yield 2-guanidino-4-carboxythiazole hydrochloride as a light yellow solid (4.33 g).

MS and $^1$H-NMR were consistent with the desired structure.

Examples L and M were prepared according to the depicted Schemes, starting from the commercially available 2-amino-6-Methylpyridine and 2-amino-4-methyl-pyridine, respectively.

EXAMPLE L

Preparation of 2-Aminopyridine-6-carboxylic acid

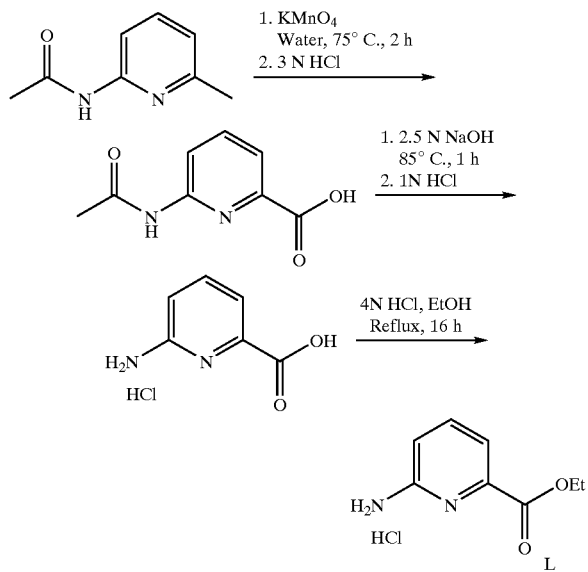

Step A

To a solution of 2-acetylamino-6-methylpyridine (10.0 g) in water (125 mL) at 75° C. was added KMnO$_4$ (21.0 g) in portions and heating was continued for 2 hours. The reaction mixture was cooled, filtered and the residue washed with hot water (2×25 mL). The combined aqueous filtrate and the washings were washed with dichloromethane (3×40 mL), and acidified with cold 3 N HCl. The resulting precipitate was filtered, washed with water to neutral pH, and dried under vacuum to afford 2-acetylaminopyridine-6-carboxylic acid (3.8 g, 48% yield). The dichloromethane extract was concentrated to dryness to give the unreacted 2-acetylamino-6-methylpyridine (3.5 g). $^1$H-NMR (CD$_3$OD) δ 8.32 (m, 1H), 7.94 (t, 1H), 7.87 (m, 1H), 2.2 (s, 3H); FAB MS m/z 181 (M+H).

Step B

A suspension of 2-acetylaminopyridine-6-carboxylic acid (4.1 g) in 2.5 N NaOH (36.5 ml) was heated at 80° C. for 1.5 hours, under nitrogen atmosphere. The resulting solution was cooled and acidified with cold 3N HCl. The precipitate obtained was filtered, washed successively with water and acetonitrile. The resulting white solid was dried under vacuum to afford 2-aminopyridine-6-carboxylic acid (2.4 g, 76% yield). $^1$H-NMR (DMSO-d$_6$) δ 7.57 (t, 1H, J=8.1 Hz), 7.14 (d, 1H, J=7.2 Hz), 6.67 (1H, J=8.1 Hz), 6.51 (br, 2H); FAB MS m/z 139 (M+H).

Step C

A suspension of 2-aminopyridine-6-carboxylic acid (2 g) in EtOH (10.0 mL) and 4N HCl/dioxane (10.0 mL) was heated to reflux for 16 hours under anhydrous conditions. The reaction mixture was then concentrated to dryness and the residue was dried in a desiccator under vacuum to afford 2-amino-6-carbethoxypyridine hydrochloride as a white powder (1.6 g). $^1$H-NMR (DMSO-d$_6$) δ 8.3 (br), 7.94 (m, 1H), 7.37 (d, 1H, J=7.2 Hz), 7.22 (dd, 1H, J=8.7 Hz), 4.37 (q, 2H, J=7.2 Hz), 1.32 (t, 3H, J=7.2 Hz); FAB MS m/z 167 (M+H).

EXAMPLE M

Preparation of 2-Aminopyridine-4-carbethoxypyridine hydrochloride

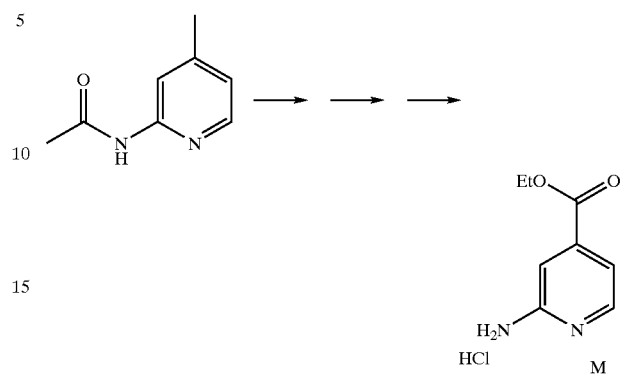

This compound (M) was prepared by a procedure similar to the procedure for preparing 2-aminopyridine-6-carbethoxypyridine hydrochloride of Example L starting from 2-acetylamino-4-methyl-pyridine.

$^1$H-NMR and MS were consistent with the structure.

EXAMPLE 1

Preparation of

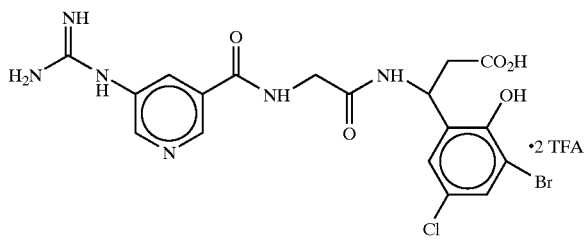

To the product of Example A (0.5 g, 0.002 mole), the product of Example E (0.83 g, 0.002 mole), triethylamine (0.2 g, 0.002 mole), and DMAP (24 mg) in anhydrous DMA (5 mL) was added EDCl (0.38 g, 0.002 mole) at ice bath temperature. The reaction was stirred at room temperature for 2 days. The ester product was isolated by reverse phase preparatory HPLC. To the ester in H$_2$O (3 mL) and CH$_3$CN (3 mL) was added LiOH (0.51 g, 0.012 mole). This was stirred at room temperature for 1 hour. The pH was lowered to 2 with TFA and the product was isolated by reverse phase preparatory HPLC to yield (after lyophilization) the desired product as a white solid (350 mg).

MS and $^1$H-NMR were consistent with the desired structure.

EXAMPLE 2

Preparation of

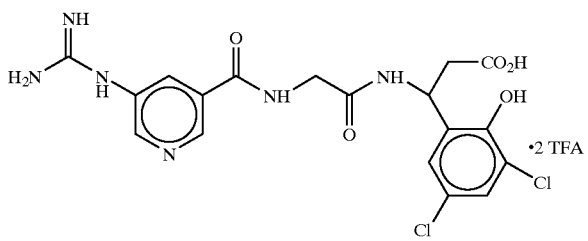

The titled compound was prepared according to the methodology of Example 1, substituting an equivalent amount of the product of Example D for the product of Example E to yield the desired product as a white solid (210 mg).

MS and ¹H-NMR were consistent with the desired structure.

EXAMPLE 3

Preparation of

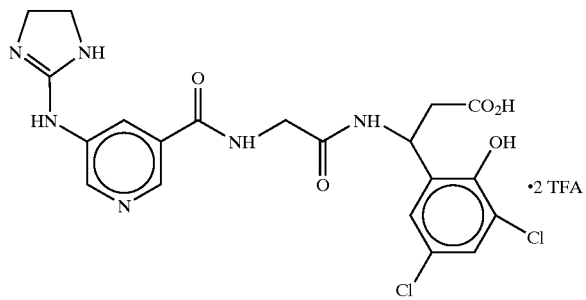

To the product of Example C (19.5 g, 0.045 mole) and N-methylmorpholine (9.1 g, 0.09 mole) in anhydrous DMA (85 mL) in a flame dried flask under $N_2$ was added isobutylchloroformate (6.2 g, 0.045 mole) slowly at ice bath temperature. The solution was stirred at ice bath temperature for 15 minutes. The product of Example D (15 g, 0.04 mole) was then added at ice bath temperature followed by slow addition of N-methylmorpholine (4.1 g, 0.04 mole). The reaction mixture was stirred overnight at room temperature. To ester in $H_2O$ (50 mL)/$CH_3CN$ (30 mL) was added LiOH (16 g, 0.38 mole). This was stirred for 1 hour at room temperature. The pH was lowered to 2 with TFA and the product was isolated by reverse phase preparatory HPLC to yield (after lyopholization) the desired product as a white solid (13.7 g).

MS and ¹H-NMR were consistent with the desired structure.

EXAMPLE 4

Preparation of

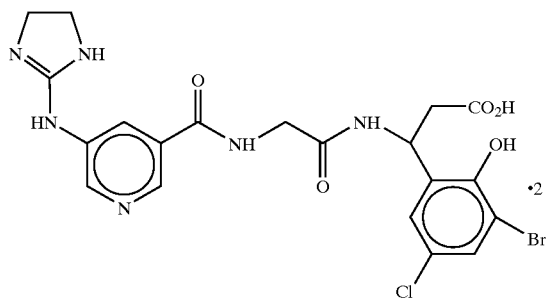

The above compound was prepared according to the methodology of Example 3, substituting an equivalent amount of the product of Example E for the product of Example D.

MS and ¹H-NMR were consistent with the desired structure.

EXAMPLE 5

Preparation of

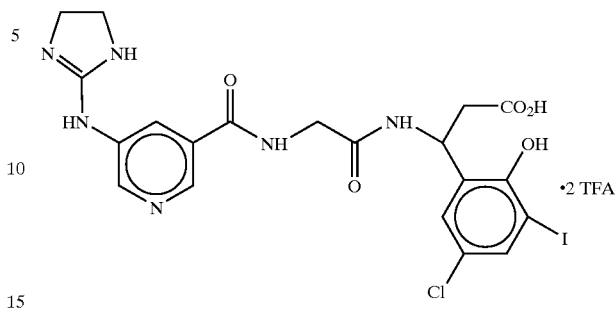

The above compound was prepared according to the methodology of Example 3, substituting an equivalent amount of the product of Example F for the product of Example D.

MS and ¹H-NMR were consistent with the desired structure.

EXAMPLE 6

Preparation of

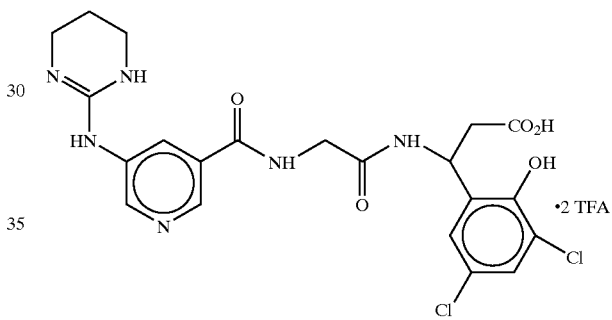

The above compound was prepared according to the methodology of Example 3, substituting an equivalent amount of the product of Example B for the product of Example C.

MS and ¹H-NMR were consistent with the desired structure.

EXAMPLE 7

Preparation of

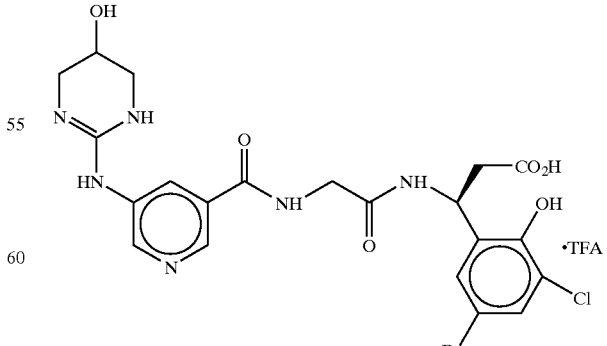

To the product of Step 3 of Example 9 (0.6 g, 0.0019 mole) in anhydrous DMA (4 mL) was added isobutylchloroformate (0.27 g, 0.002 mole) at ice bath temperature followed by N-methylmorpholine (0.4 g, 0.0038 mole). The solution was stirred for 15 minutes at ice bath temperature. The product of Example H (0.71 g, 0.0017 mole) was added at ice bath temperature followed by N-methylmorpholine (0.17 g, 0.0017 mole). The reaction was stirred overnight at room temperature. HPLC analysis indicated product plus significant amount of starting material. EDCl (0.38 g, 0.002 mole) and DMAP (15 mg) were added to the reaction mixture and the reaction was stirred overnight at room temperature. The ester product was isolated by reverse phase preparatory HPLC. To the ester in H$_2$O (10 mL) and CH$_3$CN (5 mL) was added LiOH (700 mg, 0.017 mole). This was stirred at room temperature for 1 hour. The pH was lowered to 2 with TFA and the product was isolated by reverse phase preparatory HPLC to yield (after lyophilization) the desired product as a white solid (270 mg).

MS and $^1$H-NMR were consistent with the desired structure.

EXAMPLE 8

Preparation of

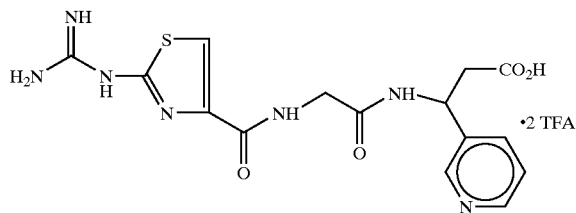

To the product of Example K (0.5 g, 0.0022 mole) and N-methylmorpholine (0.23 g, 0.0022 mole) in anhydrous DMF (8 mL) was added isobutylchloroformate (0.31 g, 0.0022 mole) at ice bath temperature. After stirring for 5 minutes at ice bath temperature, the product of Example J (0.73 g, 0.0022 mole) and N-methylmorpholine (0.45 g, 0.0045 mole) in anhydrous DMF (8 mL) were added at ice bath temperature in one portion. The reaction mixture was stirred overnight at room temperature. The ester was isolated by reverse phase preparatory HPLC (530 mg).

To this ester (400 mg) in H$_2$O (10 mL) was added LiOH (91 mg). This was stirred at room temperature for 1 hour. The pH was lowered to 3 with TFA and the product was isolated by reverse phase preparatory HPLC to yield (after lyophilization) the desired product as a white solid (350 mg).

MS and $^1$H-NMR were consistent with the desired structure.

Guanidations of 2-amino-6-carbethoxypyridine hydrochloride, and 2-amino-4-carbethoxypyridine hydrochloride, were carried out using the tris-BOC reagent as illustrated in the depicted schemes in Examples N and O (Kim. S. K., Qian, L., *Tetrahedron Lett.* 34, 7677, 1993).

EXAMPLE N

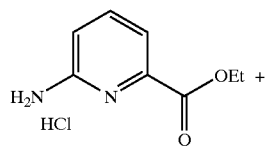

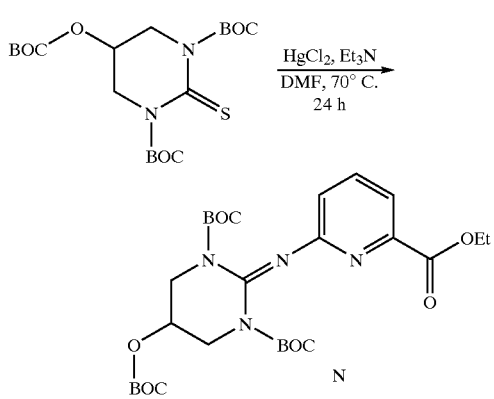

To a solution of 2-amino-6-carbethoxypyridine hydrochloride (0.56 g, 2.8 mmol) and tris-BOC reagent (91.2 g, 2.8 mmol) in degassed DMF (7.0 mL), mercuric chloride (0.76 g, 2.8 mmol), and triethylamine (0.79 g, 7.8 mmol) were added. The resulting mixture was heated at 70° C., under an atmosphere of nitrogen for 24 hours and filtered. DMF was distilled in vacuo, the residue was triturated with ethyl acetate, and filtered. The orange colored filtrate was concentrated and the resulting material was purified by silica gel flash chromatography using ethyl acetate containing 1% triethylamine as the eluent. The appropriate fractions (blue fluorescent) were combined and concentrated to dryness under reduced pressure to give a yellow powder. MS analysis [m/z 565 (M+H)] confirmed the formation of the desired tris-BOC product N.

EXAMPLE O

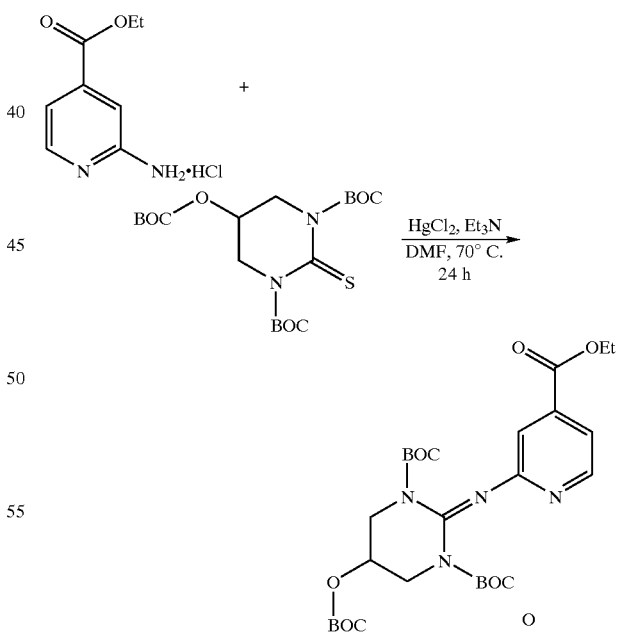

This compound (O) was prepared using a procedure similar to that of Example N. MS analysis [m/z 565 (M+H)] confirmed the formation of the desired tris-BOC product O.

The following compounds P and Q can be prepared following the conditions set forth in Steps 3–5 of Example 9.

EXAMPLE P
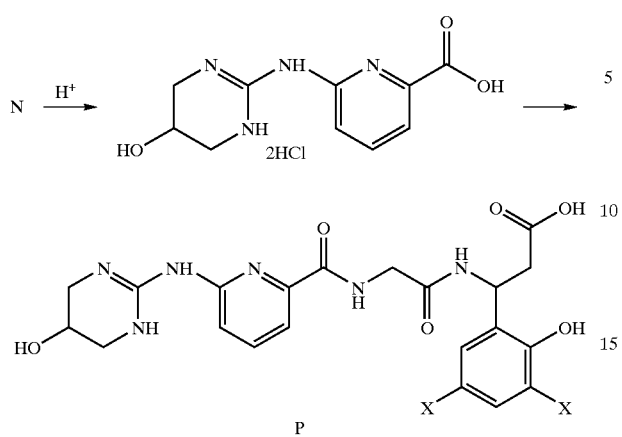
EXAMPLE Q
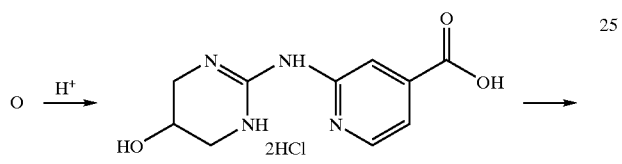
-continued
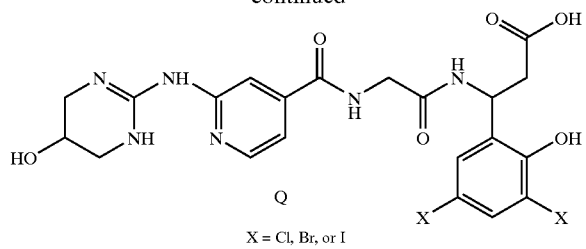
EXAMPLE R
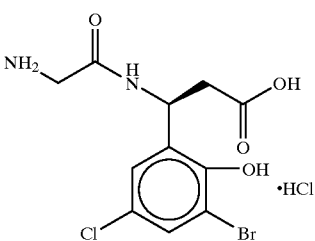
The above compound was prepared using the procedures described in Example G. The reagent 3-bromo-5-chlorosalicylaldehyde was used in Step 2 instead of 3,5-dichlorosalicylaldehyde.
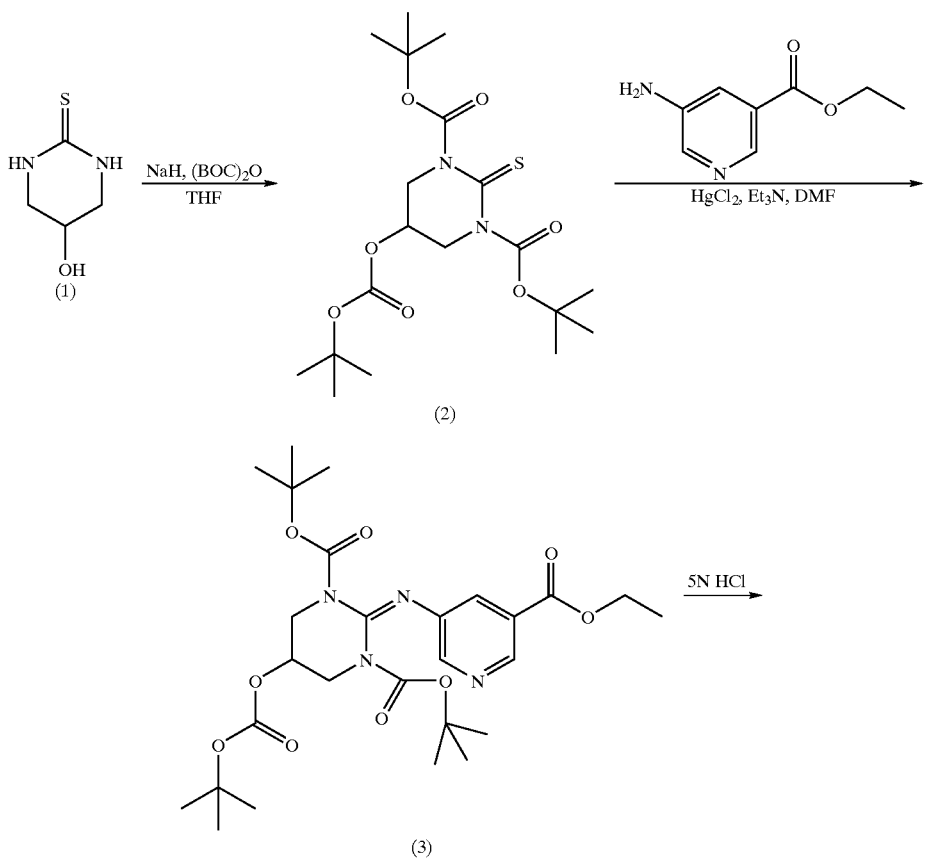

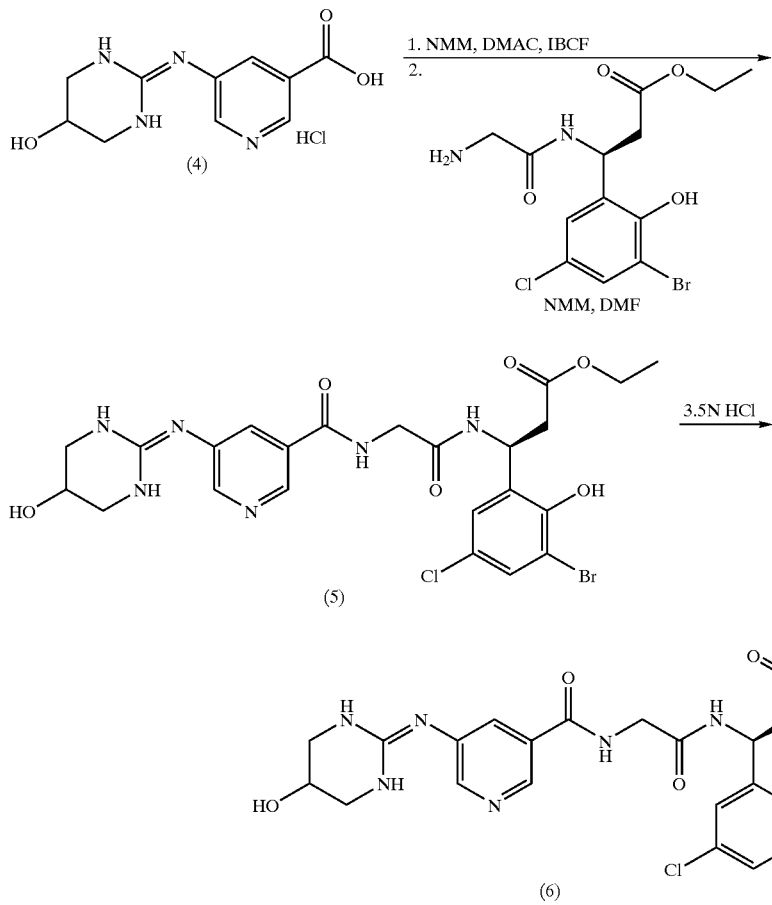

EXAMPLE 9

Step 1

To a mechanically stirred suspension of the reagent 1 (18.68 g) in THF (1 L) at 0° C. was added sodium hydride (19 g of 60% suspension in mineral oil) over 30 minutes. After 30 minutes di-tert-butyl dicarbonate (95 g) was added neat and the reaction mixture was heated to reflux gently for 16 hours. The mixture was cooled to 0° C. and quenched with a saturated solution of NaHCO₃. The mixture was extracted with ethyl acetate. The organic extract was washed with water, dried (Na₂SO₄) and concentrated. The residue was rapidly chromatographed using a small column of silica gel (60 mm×180 mm) to give the desired product 2 as a thick yellow liquid (68 g). NMR was consistent with the assigned structure.

Step 2

A stirred suspension of 3-amino-pyridine-6-carboxylic acid (25 g) in ethanol (300 mL) at 0° C. was saturated with gaseous hydrogen chloride. The mixture was allowed to warm to 23° C. and heated to reflux for 2 hours. A clear solution was obtained. After cooling to 23° C., the mixture was concentrated in vacuo, neutralized with aqueous NaHCO₃ and extracted with ethyl acetate. The organic phase was washed with water, dried over MgSO₄, and concentrated in vacuo to give ethyl 3-amino-pyridine-6-carboxylate as a pale yellow solid.

A mixture of the product of Step 1 (40.0 g), HgCl₂ (25.0 g) triethylamine (27 mL) and ethyl 3-amino-pyridine-6-carboxylate (13 g) and DMF (200 mL) was stirred and heated to 55° C. for 30 hours. The reaction mixture was cooled to 23° C., diluted with ethyl acetate (500 mL) and filtered through celite. The filtrate was washed with water (2×), dried over MgSO₄ and concentrated in vacuo. The residue was chromatographed over silica gel using ethyl acetate in hexane as eluant to give the desired intermediate 3. NMR was consistent with the desired structure.

Step 3

A suspension of the product of Step 2 (13 g) in 5N hydrochloric acid (100 mL) was stirred for 16 hours at 23° C. The mixture was concentrated in vacuo. The residue was triturated with methanol and the white solid was filtered to provide the desired product 4. NMR and MS were consistent with the desired structure.

Step 4

The product of Step 3 (0.308 g) was suspended in DMF (10 mL) and 4-methylmorpholine (0.2 mL) was added to the suspension. The mixture was stirred at 23° C. for 1 hour. After cooling the reaction mixture to 0° C., IBCF (0.129 mL) was added. After ½ hour, a solution of the product of Example R (0.416 g) and 4-methylmorpholine (0.11 mL) in DMF (3 mL) was added. The mixture was allowed to warm to 23° C. over 2 hours. Then the mixture was filtered and the filtrate concentrated in vacuo. The residue was purified by HPLC to provide 5. Micro-analytical data, NMR and MS were consistent with the desired structure.

Step 5

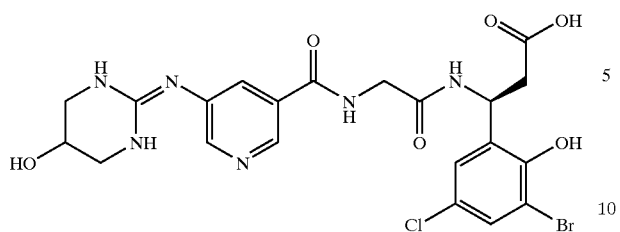

A solution of the product of Step 4 in 3.5N HCl was allowed to stand at 23° C. for 3 hours, concentrated in vacuo and the residue purified by HPLC to provide the desired product. Micro-analytical data, NMR and MS were consistent with the desired product.

Analysis calculated for $C_{21}H_{22}BrClN_6O_6 \cdot 2CF_3CO_2H \cdot H_2O$: C, 36.80; H, 3.21; N, 10.30. Found: C, 36.52; H, 2.90; N, 9.91.

EXAMPLE 10

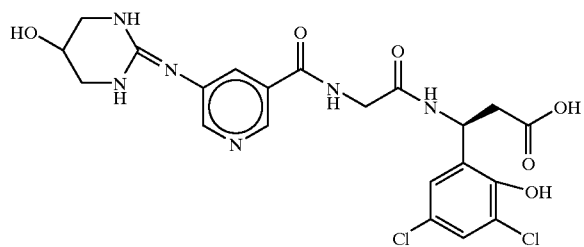

This compound was prepared using the procedure described in Example 9, except that the product of Example G was used instead of the product of Example R in Step 4.

Analysis calculated for $C_{21}H_{22}Cl_2N_6O_6 \cdot 2CF_3CO_2H \cdot H_2O$: C, 38.93; H, 3.40; N, 10.89. Found: C, 39.27; H, 3.12; N, 11.09.

EXAMPLE 11

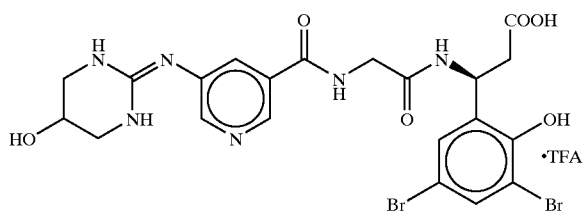

The compound was prepared as described for Example 9 using the product of Example I instead of the product of Example R in Step 4.

Analysis calculated for: $C_{21}H_{22}Br_2N_6O_6 \cdot 2 CF_3COOH \cdot H_2O$ C, 35.65; H, 2.87; N, 9.98. Found: C, 35.81; H, 2.79; N, 10.14.

EXAMPLE 12

Preparation of (3S)-N-[[4-[(1,4,5,6-tetrahydro-5-hydroxy-2-pyrimidinyl)amino]-2-thienyl]carbonyl]glycyl-3-(3,5-dichloro-2-hydroxyphenyl)-β-alanine, trifluoroacetate salt

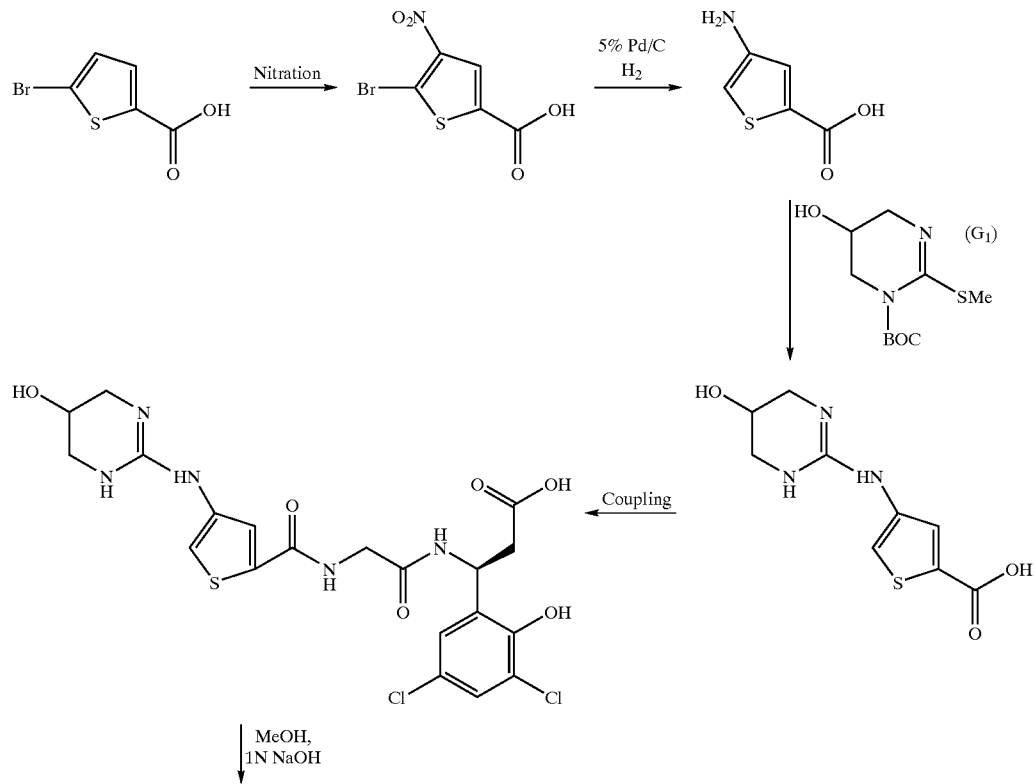

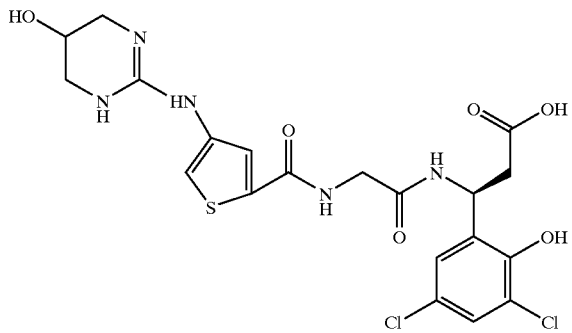

Step 1

A solution of 5-bromo-2-thiophene carboxylic acid (5.0 g) in concentrated sulfuric acid (30 ml) was chilled to −30° C. and treated dropwise with a solution of 70% nitric acid (7.7 ml) (d=1.40) in concentrated sulfuric acid (30 ml). The reaction mixture was stirred for 30 minutes at −25° C. and then poured over ice water slurry and stirred for a few minutes. The precipitated solid was filtered, recrystallized from water and dried to afford a white powder (2.3 g). The $^1$H-NMR was consistent with the proposed structure.

Step 2

A solution of the product from Step 1 (1.7 g) in THF (25 ml) was treated with a catalytic amount of 5% Pd/C under 5 psi atmosphere of hydrogen at room temperature for 16 hours. The reaction mixture was filtered and concentrated. The residue was heated with ethyl acetate and filtered to yield a brown solid (750 mg). $^1$H-NMR was consistent with the proposed structure.

Step 3

A solution of the product from Step 2 (725 mg) and the guanylating reagent G1 in THF (15 ml) and dimethylacetamide (10 ml) was refluxed for 16 hours. The reaction mixture was concentrated and the residue treated with a solution of TFA (5 ml) and CH$_2$Cl$_2$ (5 ml). After stirring at room temperature for 1 hour, the reaction mixture was concentrated and the residue purified on reverse phase HPLC using water (0.5% TFA) and acetonitrile gradient as eluant to afford a light yellow thick liquid (300 mg). $^1$H-NMR was consistent with the proposed structure.

Step 4

In a flame dried flask under N$_2$ the product from Step 3 (275 mg) was dissolved in 8 ml of dimethylacetamide and N-methylmorpholine (81 mg). The stirred solution was chilled to 0° C. and treated dropwise with a solution of isobutyl chloroformate (109 mg) in dimethylacetamide (1 ml). The reaction mixture was stirred for 45 minutes at 0° C. and then treated dropwise with a solution of the product of Example G (286 mg) and N-methylmorpholine (81 mg) in dimethylacetamide (2 ml). The reaction mixture was allowed to warm to room temperature and stirring was continued for 16 hours. The reaction mixture was concentrated and the residue purified using reverse phase HPLC as described in Step 3 to afford a thick colorless liquid (262 mg). $^1$H-NMR was consistent with the proposed structure.

Step 5

A solution of the product from Step 4 (250 mg) in methanol (8 ml) and 1N sodium hydroxide solution (8 ml) was stirred at room temperature for 16 hours. The reaction was quenched with TFA (0.7 ml) and concentrated. The residue was purified using reverse phase HPLC as described in Step 3 to give a white solid (144 mg). $^1$H-NMR was consistent with the proposed structure.

Analysis calculated for C$_{20}$H$_{21}$N$_5$O$_6$Cl$_2$S.1.50TFA.0.25H$_2$O: C, 39.13; H, 3.28; N, 9.92; S, 4.54; Cl, 10.04; found: C, 38.81; H, 3.17; N, 9.90; S, 4.86; Cl, 10.25.

EXAMPLE 13

Preparation of N-[[4-[(4,5-dihydro-1H-imidazol-2-yl)amino]-2-thienyl]carbonyl]glycyl-3-(3,5-dichloro-2-hydroxyphenyl)-β-alanine, trifluoroacetate salt

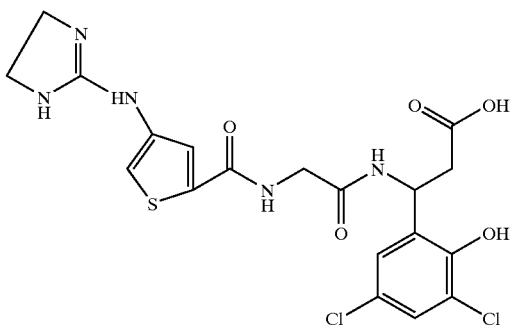

The above compound was prepared in an analogous sequence of reactions as used in the preparation of the compound described in Example 12. The guanylating agent described in Example C (Step 1) was used instead of G1 in Step 3 of Example 12. Similarly, the product of Example D was used instead of the product of Example G in Step 4. $^1$H-NMR was consistent with the proposed structure.

Analysis calculated for: C$_{19}$H$_{19}$N$_5$O$_5$Cl$_2$S.1.50TFA.0.50H$_2$O: C, 38.84; H, 3.18; N, 10.29; S, 4.71; Cl, 10.42. found: C, 38.84; H, 3.01; N, 10.50; S, 5.08; Cl, 11.01.

EXAMPLE 14

Preparation of (3S)-N-[[5-methyl-4-[(1,4,5,6-tetrahydro-5-hydroxy-2-pyrimidinyl)amino]-2-thienyl]carbonyl]glycyl-3-(3,5-dichloro-2-hydroxyphenyl)-β-alanine, trifluoroacetate salt

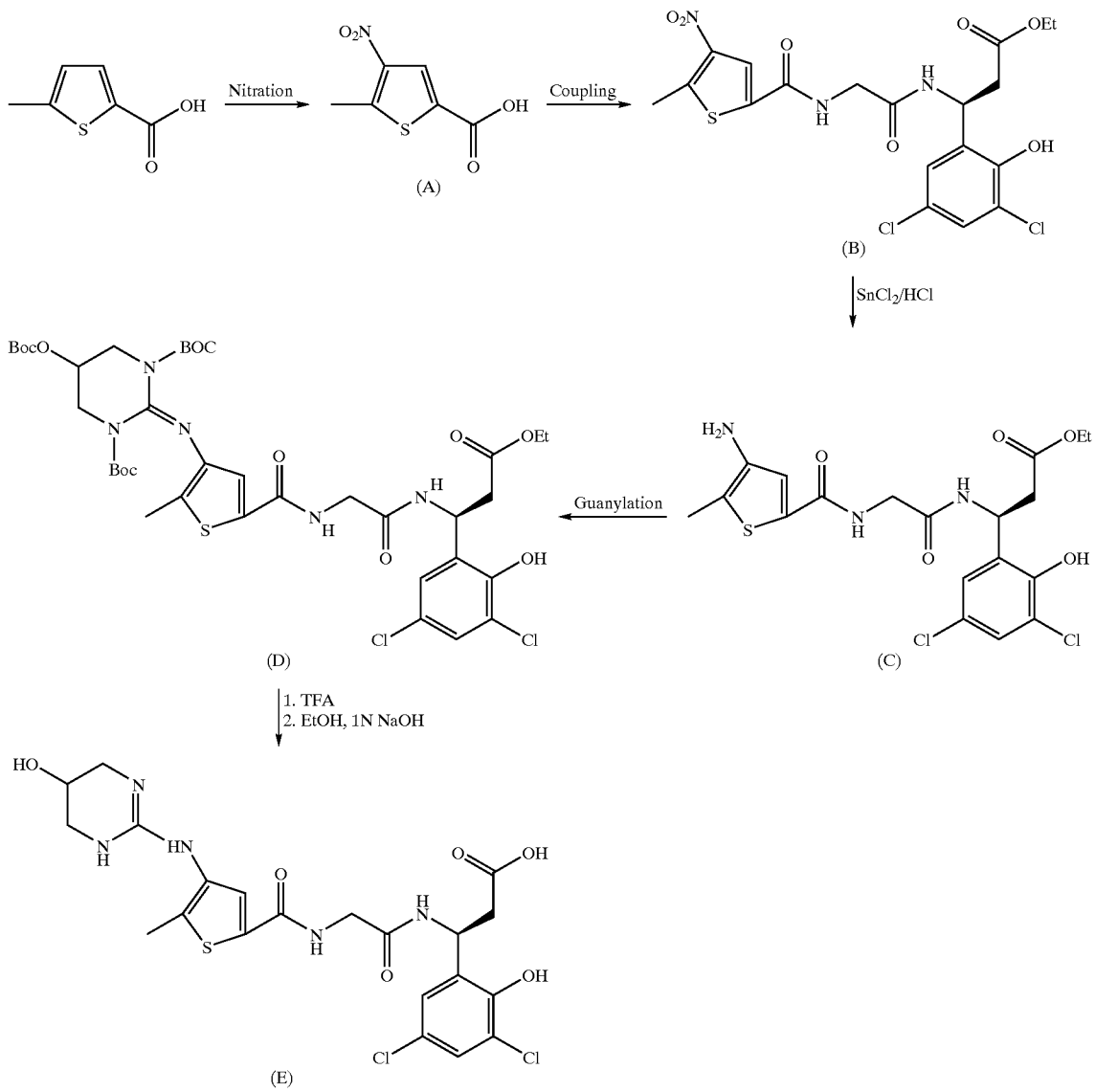

Step 1

(A) was prepared as described in Step 1 of Example 13 using 5-methyl-2-thiophene carboxylic acid (5.2 g). The product was purified by extraction with dilute sodium hydroxide solution, acidification with dilute hydrochloric acid and extraction into ethyl acetate. The organic extract was dried (Na$_2$SO$_4$) and concentrated to afford a yellowish orange solid (2.2 g). $^1$H-NMR was consistent with the proposed structure.

Step 2

(B) was prepared using the product of Step 1 (2.2 g) and following the coupling conditions as described in Step 4 of Example 12. The reaction was concentrated and the residue partitioned between ethyl acetate and water. The organic extract was washed with saturated sodium chloride solution, dried (Na$_2$SO$_4$) and concentrated. The residue was recrystallized from ethyl acetate to afford a tan solid (3.5 g). $^1$H-NMR was consistent with the proposed structure.

Step 3

A solution of the product from Step 2 (2.8 g) in THF (25 ml) was treated dropwise with a solution of tin(II) chloride dihydrate in concentrated hydrochloric acid (1.0 g/2 ml) at room temperature until TLC indicated complete disappearance of the starting material. The organic solvent was removed and the aqueous portion neutralized with sodium bicarbonate solution. The aqueous portion was extracted with CH$_2$Cl$_2$, dried (Na$_2$SO$_4$), and concentrated to afford a yellow powder (1.1 g). $^1$H-NMR was consistent with the proposed structure.

Step 4

To a solution of the product described in Step 3 (375 mg) and the product of Step 1 of Example 9 (519 mg) in DMF (15 ml), mercuric chloride (326 mg) and triethylamine (182 mg) were added. The mixture was heated at 95–100° C. for 3 hours. The reaction mixture was cooled, treated with ethyl acetate (30 ml), stirred for 30 minutes and then filtered through a pad of celite. The filtrate was concentrated and the residue purified using flash chromatography (eluting with 97.5% CHCl$_3$-2.5% CH$_3$OH) to yield a yellowish brown solid (415mg). $^1$H-NMR was consistent with the proposed structure.

Step 5

A solution of the product from Step 4 (400 mg) in CH$_2$Cl$_2$ (7.5 ml) and TFA (7.5ml) was stirred at room temperature for 1 hour. The reaction was concentrated and the residue was stirred into a solution of CH$_3$OH (10 ml) and 1N sodium hydroxide solution (10 ml) at room temperature for 16 hours. The reaction was quenched with TFA (0.8 ml) and concentrated. The residue was purified using reverse phase HPLC as previously described to produce a white solid (80 mg). $^1$H-NMR was consistent with the proposed structure Analysis calculated for: C$_{21}$H$_{23}$N$_5$O$_6$Cl$_2$.1.50 TFA. 0.50 H$_2$O: C, 39.79; H, 3.55; N, 9.67; S, 4.43; Cl, 9.79. found: C, 39.50; H, 3.24; N, 9.58; S, 4.71; Cl, 10.22.

EXAMPLE 15

Preparation of (3S)-N-[[4-(4,5,-dihydro-1H-imidazol-2-yl)amino]-5-methyl-2-thienyl]carbonyl]glycyl-3-(3,5-dichloro-2-hydroxyphenyl)-β-alanine, trifluoroacetate salt

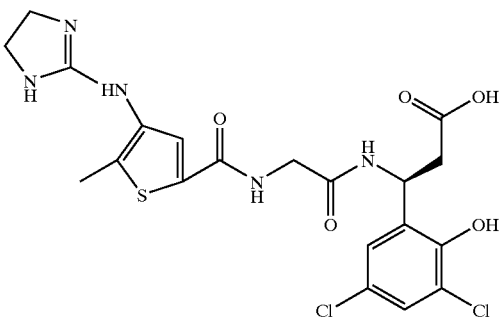

The above compound was prepared in an analogous sequence of reactions as used in the preparation of the compound described in Example 14, except the guanylating agent described in Example C (Step 1) was used instead of the reagent used in Step 4 of Example 14. $^1$H-NMR was consistent with the proposed structure.

Analysis calculated for: C$_{20}$H$_{21}$N$_5$O$_5$Cl$_2$S.1.50 TFA.0.25 H$_2$O. C, 40.04; H, 3.36; N, 10.15; S, 4.65; Cl, 10.28. found: C, 39.82; H, 3.19; N, 10.17; S, 4.86; Cl, 10.69.

EXAMPLE 16

N-[[5-(4,5,-dihydro-1H-imidazol-2-yl)amino]-2-thienyl]carbonyl]glycyl]-3-(3,5-dichloro-2-hydroxyphenyl)-β-alanine, trifluoroacetate salt

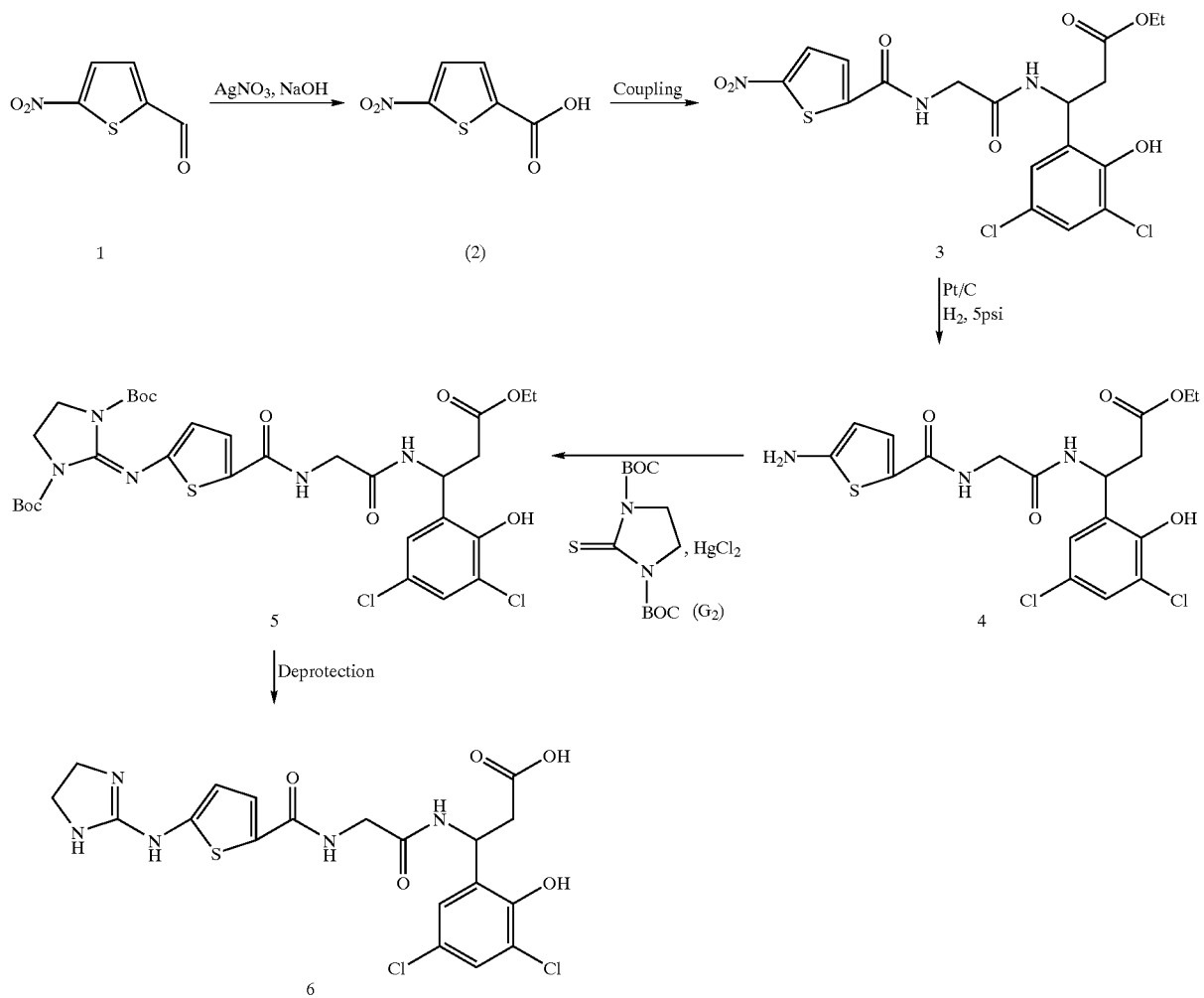

The title compound was synthesized starting with 2-nitro-5-thiophene-carboxylic acid utilizing the same sequence of reactions as described in Example 15. For the guanylation reaction, the conditions described in Step G, Example 17 were followed.

Analysis calculated for: C19H19N5O5Cl2S.1.50 TFA. C, 39.36; H, 3.08; N, 10.43; S, 4.78: found: C, 39.05; H, 2.79; N, 10.37; S, 4.90.

EXAMPLE 17

N-[[5-(4,5,-dihydro-1H-imidazol-2-yl)amino]-6-methoxy-3-pyridinyl]carbonyl]glycyl]-3-(3,5-dichloro-2-hydroxyphenyl)-β-alanine, bis(trifluoroacetate) salt

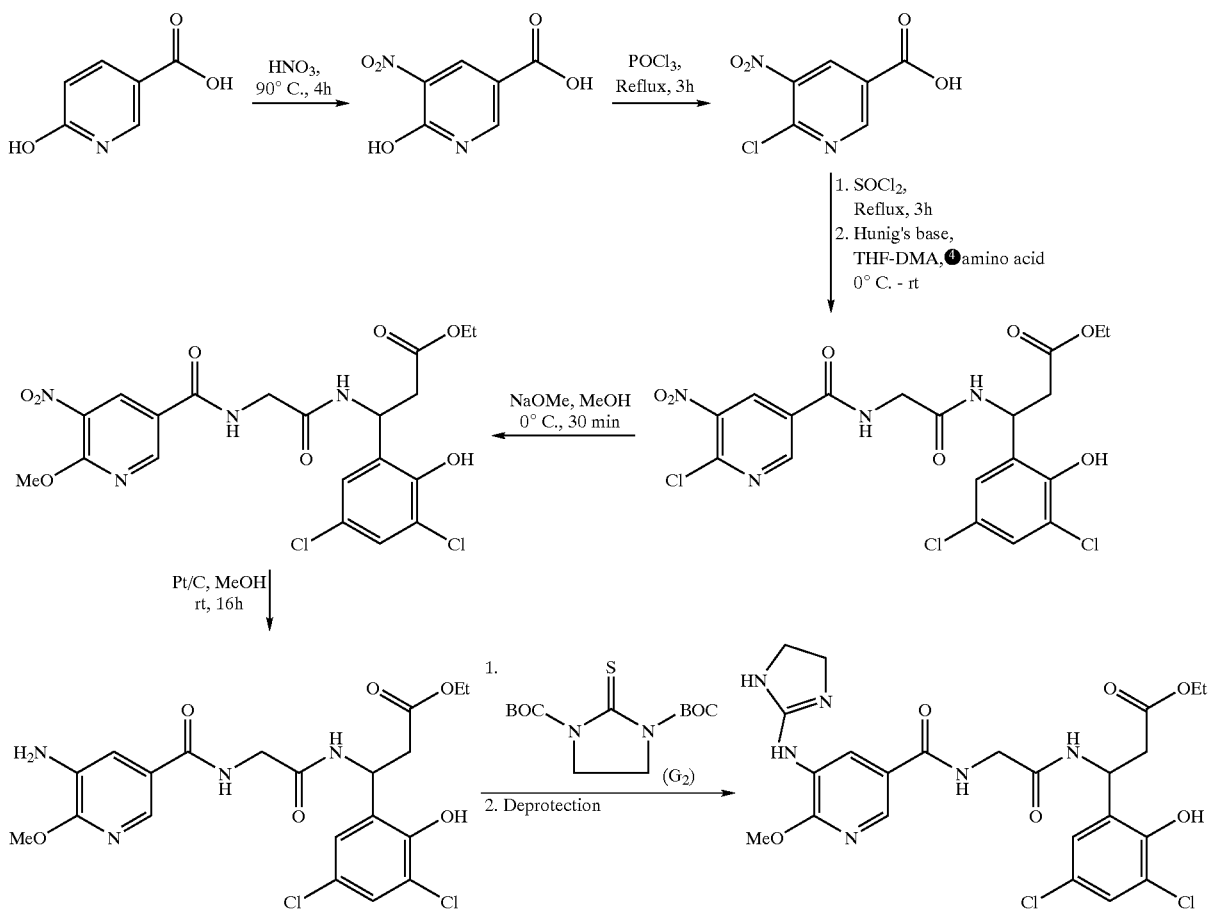

Step 1

A mixture of 6-hydroxynicotinic acid (20 g) and colorless fuming nitric acid (60 ml) (d=1.50) was heated to 90–95° C. for 3 hours. The reaction was cooled to room temperature and poured onto 1.5 litre of an ice-water slurry with stirring and then filtered after 15 minutes. The precipitate was washed with water and dried to afford a light yellow powder (9.3 g). $^1$H-NMR was consistent with the proposed structure.

Analysis calculated for C6H4N2O5: C, 39.14; H, 2.19; N, 15.22. found: C, 39.08; H, 2.17; N, 15.19.

Step 2

A mixture of the product from Step 1 (5.0 g) and phosphorus oxychloride (15 ml) was refluxed for 3 hours. The reaction mixture was cooled to room temperature and added to an ice-water mixture and stirred for 30 minutes. Additional ice was added to keep the mixture cold during this period. The reaction mixture was extracted with a THF-ether (1:2) mixture and the organic extracts washed with saturated sodium chloride solution, dried (Na2SO4) and concentrated. The residue was recrystallized from 1:1 ether-hexane to yield a yellow powder (4.0 g). $^1$H-NMR was consistent with the proposed structure.

Step 3

A solution of the product from Step 2 (1.6 g) in thionyl chloride (5.0 ml) was refluxed for 3 hours. The reaction was cooled to room temperature and evaporated under a stream of nitrogen. The residue was dried under vaccuum and used without further purification. In a flame dried flask under nitrogen, the product of Example D (3.0 g) was dissolved in dimethylacetamide (30 ml) and N,N-diisopropylethylamine (2.3 g). The solution was chilled in an ice bath and a solution of the acid chloride (as obtained above) in THF (20 ml) was added dropwise. The reaction was stirred and allowed to warm to room temperature and then quenched with water (25 ml). The mixture was extracted with ethyl acetate and the organic extracts washed with saturated sodium chloride solution, dried (Na2SO4) and concentrated. The resulting yellow solid was recrystallized from ethyl acetate to afford a light yellow powder (3.4 g). $^1$H-NMR was consistent with the proposed structure

Step 4

To a suspension of sodium methoxide (2.2 g) in methanol (30 ml) was added dropwise at 0° C. a solution of the product of Step 3 (4.5 g) in methanol (30 ml). The reaction was stirred for 30 minutes and then quenched with acetic acid (2.3 ml). The reaction was concentrated and partitioned between ethyl acetate and water. The organic extracts were dried ($Na_2SO_4$), concentrated, and purified on a silica gel column (eluting with 80% ethyl acetate −20% hexane) to produce a light yellow solid (3.5 g). $^1$H-NMR was consistent with the proposed structure.

Step 5

A solution of the product described in Step 4 (1.07 g) in ethanol (25 ml) was treated with a catalytic amount of 3% Pt/C poisoned with sulfur under a 5 psi atmosphere of hydrogen at room temperature for 4 hours. The reaction mixture was filtered and concentrated to yield a white solid (930 mg) which was used without further purification. $^1$H-NMR was consistent with the proposed structure Step 6

To a solution of the product of Step 5 (330 mg), $G_2$ (276 mg) in DMF (10 mL) was added triethylamine (150 mg) and mercuric chloride (258 mg) and the mixture heated at 85° C. under nitrogen for 16 hours. The reaction was cooled, treated with ethyl acetate (25 ml) and filtered. The filtrate was concentrated and the residue purified on a silica gel column eluting with 98% $CH_2Cl_2$-2% methanol to afford white solid (325 mg). $^1$H-NMR was consistent with the proposed structure.

Step 7

A solution of the product from Step 6 (114 mg), TFA (8 ml) and methylene chloride (8 mL) was stirred at room temperature for 90 minutes. The solvent was evaporated and the residue treated with a solution of 1N sodium hydroxide (8 mL) and methanol (8 mL) at room temperature for 16 hours. The reaction was quenched with TFA (1 mL) and concentrated. The residue was purified using reverse phase HPLC as previously described to afford a white solid (76 mg). $^1$H-NMR was consistent with the proposed structure.

Analysis calculated for: $C_{21}H_{22}N_6O_6Cl_2 \cdot 2TFA$: C, 41.74; H, 3.88; N, 12.70. found: C, 41.47; H, 3.49; N, 12.85.

EXAMPLE 18

N-[[5-(4,5,-dihydro-1H-imidazol-2-yl)amino]-1,6-dihydro-1-methyl-6-oxo-3-pyridinyl]carbonyl]glycyl-3-(3, 5-dichloro-2-hydroxyphenyl-β-alanine, (trifluoroacetate) salt

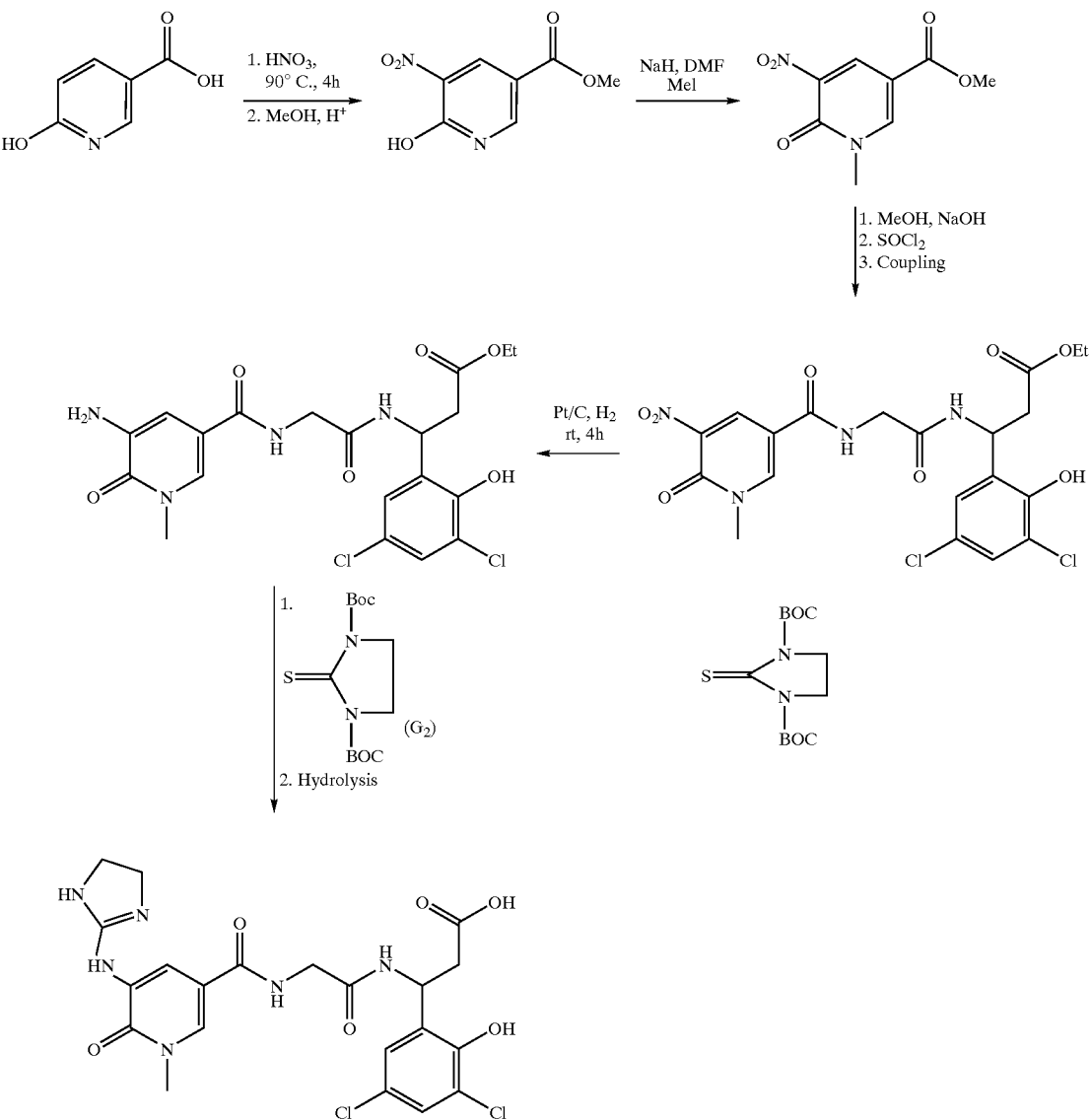

Step 1

A suspension of the product from Example 17, Step 1 (12.0 g) in methanol (200 ml) was treated with concentrated sulfuric acid (1 ml) and brought to reflux. After refluxing for 16 hours, the reaction mixture became a homogenous solution and was allowed to cool to room temperature. Approximately one half of the solvent was removed at which point the product crystallized from solution. The mixture was cooled in an ice bath, filtered and dried to afford a yellow powder (16.7 g). $^1$H-NMR was consistent with the proposed structure.

Step 2

A solution of the product from Step 1 (2.6 g) in DMF (40 ml) was chilled to 0° C. under $N_2$ and treated with a 60% dispersion of sodium hydride in mineral oil (655 mg). The mixture was stirred at 0° C. for 45 minutes and then treated with iodomethane (2.8 g) in one portion. The reaction was stirred at room temperature for 16 hours, and then partitioned between ethyl acetate and water. The aqueous portion was extracted several times with additional ethyl acetate and then the combined organic extracts were washed with saturated sodium chloride solution, dried ($Na_2SO_4$) and concentrated. The residue was purified on a silica gel column (eluting with 2% methanol-98% methylene chloride) to yield a yellow solid (1.9 g). $^1$H-NMR was consistent with the proposed structure.

Step 3

A solution of the product from Step 2 (2.6 g), methanol (60 ml) and 2N sodium hydroxide solution (60 ml) was stirred at room temperature for 16 hours. The reaction was quenched with glacial acetic acid (6.9 ml) and concentrated. The residue was dried under high vacuum. This material was then refluxed with thionyl chloride (100 ml) under nitrogen for 3 hours. The reaction was cooled, concentrated and dried thoroughly under high vacuum to afford a tan solid (2.2 g). $^1$H-NMR was consistent with the proposed structure. In a flame dried flask under nitrogen, the product of Example D (3.5 g) was dissolved in N,N-dimethylacetamide (35 ml) and diisopropylethylamine (2.9 ml). The solution was chilled to 0° C. and treated with a solution of the acid chloride (1.9 g) (as obtained above) in THF (35 ml). The reaction was stirred for 30 minutes and then concentrated under high vacuum to remove the solvents. The residue was partitioned between ethyl acetate and water and the aqueous portion was extracted several times with additional ethyl acetate. The combined organic extracts were washed with water several times and then washed with saturated sodium chloride solution, dried ($Na_2SO_4$) and concentrated to produce a yellow solid (1.3 g). $^1$H-NMR was consistent with the proposed structure.

Step 4

A solution of the product from Step 3 (1.0 g) in THF (10 ml) and DMF (10 ml) was treated with a catalytic amount of 5% Pt/C under a 5 psi atmosphere of hydrogen at room temperature for 4 hours. The reaction mixture was filtered and concentrated. The residue was taken up in minimal amount of THF and allowed to crystallize slowly at room temperature. An equal volume of ethyl acetate was added to the crystallized mixture and digested for 15 minutes. The mixture was cooled, filtered and washed with cold ethyl acetate. The product was dried to afford a white solid (730 mg). $^1$H-NMR was consistent with the proposed structure.

Step 5

To a solution of the product from Step 4 (720 mg) and $G_2$ (581 mg) in DMF (25 ml), triethylamine (304 mg) and mercuric chloride (544 mg) were added and the mixture heated at 85° C. under nitrogen for 1 hour. The reaction mixture was cooled and filtered through a pad of celite. The filtrate was concentrated and purified on a silica gel column (eluting with 10% methanol-90% chloroform) to yield a white solid (375 mg). $^1$H-NMR was consistent with the proposed structure.

Step 6

The above compound was prepared from the compound prepared in Step 5 (360 mg) utilizing the procedure described in Example 14 (Step 5). The crude product was purified using reverse phase HPLC as previously outlined to yield a white solid (223 mg). $^1$H-NMR was consistent with the proposed structure.

Analysis calculated for: $C_{21}H_{22}N_6O_6Cl_2 \cdot 2.5TFA \cdot 0.5H_2O$: C, 38.11; H, 3.14; N, 10.26; Cl, 8.65. found: C, 38.18; H, 3.05; N, 10.79; Cl, 9.34.

EXAMPLE 19

N-[[6-chloro-5-[(4,5,-dihydro-1H-imidazol-2-yl)amino]-3-pyridinyl]carbonyl]-glycyl-3-(3,5-dichloro-2-hydroxyphenyl)-β-alanine, (trifluoroacetate) salt, monohydrate

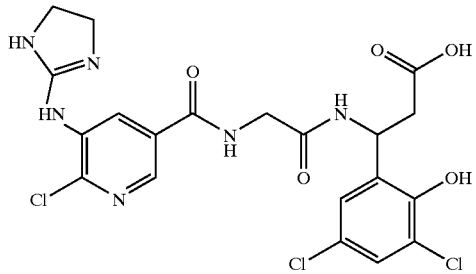

Step 1

A solution of tin(II) chloride (6.3 g) in concentrated hydrochloric acid (10 ml) was prepared and was added dropwise to a solution of the product from Step 3, Example 17 (1.0 g) in THF (15 ml). The reaction was stirred for 15 minutes at which time the reaction had cooled back to room temperature. The organic solvent was removed to give a gummy precipitate. The aqueous portion was decanted and the gummy precipitate partitioned between ethyl acetate and dilute sodium bicarbonate solution. The aqueous portion was extracted several times with additional ethyl acetate and the combined organic extracts were then washed with water and saturated sodium chloride solution, dried ($Na_2SO_4$) and concentrated. The residue was dried under vaccuum to afford a tan powder (375 mg). $^1$H-NMR was consistent with the proposed structure.

Step 2

The compound described in Step 1 (365 mg) was guanylated utilizing the methodology outlined in Step 5, Example 18. The crude product was purified on a silica gel column (eluting with 2% methanol-98% chloroform) to yield a brownish thick liquid (205 mg). $^1$H-NMR was consistent with the proposed structure.

Step 3

The title compound was prepared using the product of Step 2 (200 mg) and following the procedure described in Step 7, Example 17. The crude product was purified using the reverse phase HPLC as previously described to afford a white solid (53 mg). $^1$H-NMR was consistent with the proposed structure.

Analysis calculated for $C_{20}H_{19}N_6O_5Cl_3 \cdot 1.7\,TFA \cdot 1.0\,H_2O$: C, 37.90; H, 3.09; N, 11.33; Cl, 14.34. found: C, 37.53; H, 2.71; N, 11.33; Cl, 15.01.

EXAMPLE 20

N-[[5-[(4,5,-dihydro-1H-imidazol-2-yl)amino]-1,6-dihydro-6-oxo-3-pyridinyl]-carbonyl]glycyl-3-(3,5-dichloro-2-hydroxyphenyl)-β-alanine, (trifluoroacetate) salt

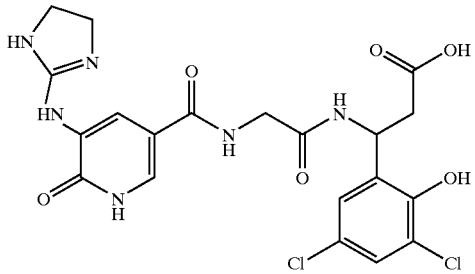

The above compound was prepared by dissolving the product from Example 17, Step 6 (353 mg) in a 6N solution of hydrochloric acid (50 ml) at room temperature for 48 hours. The reaction was concentrated and the residue purified using reverse phase HPLC as previously described to afford a white solid (115 mg). $^1$H-NMR was consistent with the proposed structure.

Analysis calculated for $C_{20}H_{20}N_6O_6Cl_2 \cdot 1.25$ TFA: C, 41.33; H, 3.28; N, 12.85. found: C, 41.57; H, 3.29; N, 12.92.

EXAMPLE 21

Preparation of (3S)-N-[[1,6-dihydro-6-oxo-5-[(1,4,5,6-tetrahydro-5-hydroxy-2-pyrimidinyl)amino]-3-pyridinyl]carbonyl]glycyl-3-(3,5-dichloro-2-hydroxyphenyl)-β-alanine, trifluoroacetate salt

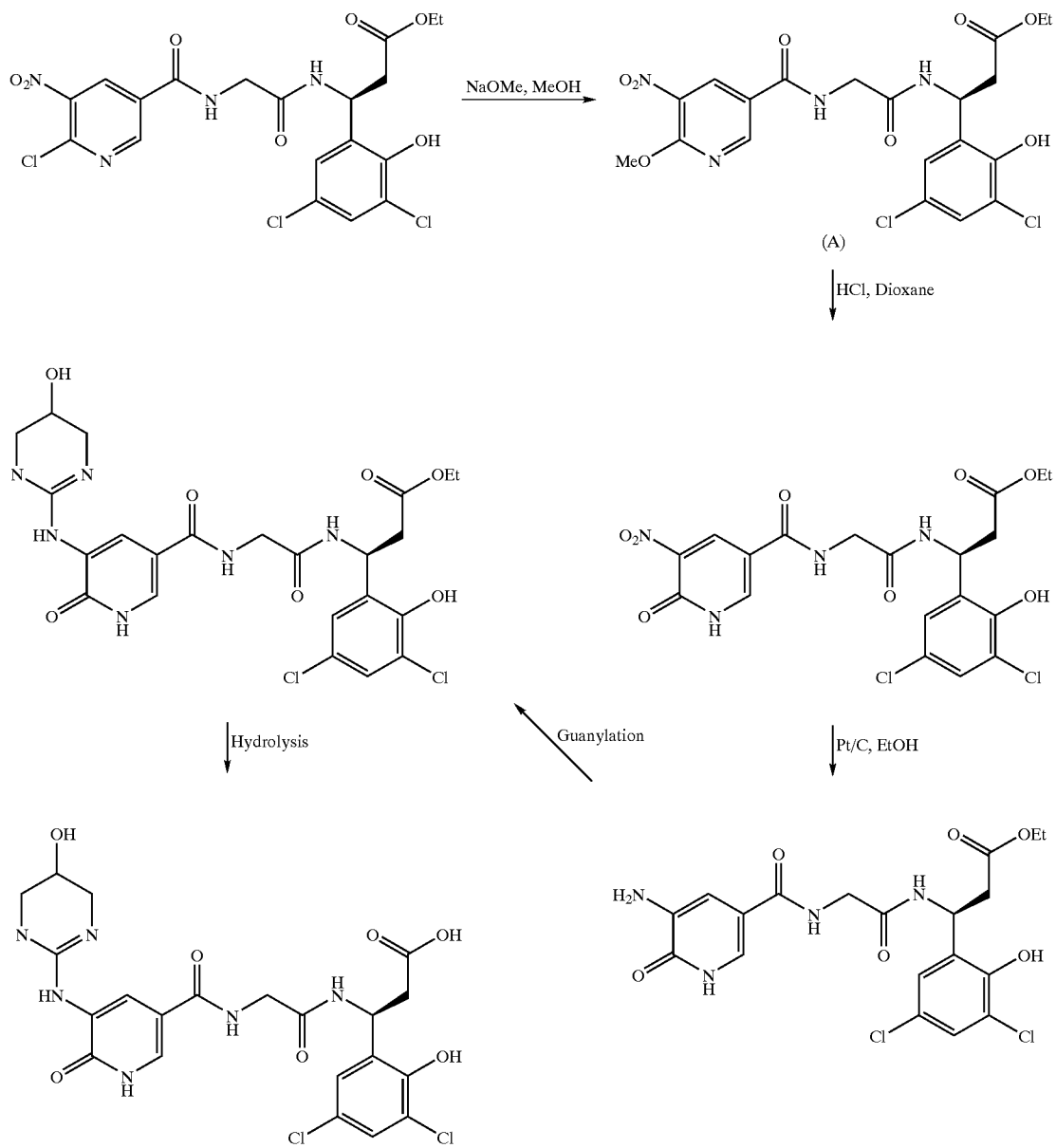

The starting material used in the preparation of the title compound was synthesized utilizing the sequence of reactions described in Example 17 (Steps 1–3). Instead of the product of Example D the chiral intermediate of Example G was utilized in the coupling reaction detailed in Step 3.

Step 1

(A) was prepared using the procedure given in Step 4, Example 17. $^1$H-NMR was consistent with the proposed structure.

Step 2

A solution of the material from Step 1 (2.7 g) in 4N anhydrous HCl/dioxane (100 ml) was warmed to 45° C. under $N_2$ for 72 hours. The reaction was concentrated to dryness to afford a light brown solid (2.6 g). $^1$H-NMR was consistent with the proposed structure.

Step 3

A solution of the product from Step 2 (1.85 g) in ethanol (50 ml) was treated with a catalytic amount of 5% Pt/C under a 5 psi atmosphere of hydrogen at room temperature for 2 hours. The reaction mixture was filtered and concentrated and the residue purified using reverse phase HPLC to yield a white solid (507 mg). $^1$H-NMR was consistent with the proposed structure.

Step 4

To a solution of the product from Step 3 (500 mg) and the product of Step 1 of Example 4 (650 mg) in DMF (15 ml), triethylamine (304 mg) and mercuric chloride (408 mg) were added and the mixture heated to 100° C. for 2 hours under nitrogen. The reaction mixture was cooled to room temperature and stirred with ethyl acetate (30 ml) for 15 minutes and then filtered. The filtrate was concentrated and the residue treated with a solution of TFA (7 ml) and $CH_2Cl_2$ (7 ml) at room temperature for one hour. The mixture was concentrated and the residue purified using reverse phase HPLC as previously described to afford a white solid (400 mg). $^1$H-NMR was consistent with the proposed structure.

Step 5

A solution of the product from Step 4 (200 mg), 1N sodium hydroxide (8 ml) and methanol (8 ml) was stirred at room temperature for 16 hours. The reaction was quenched with TFA (1 ml) and concentrated. The residue was purified using reverse phase HPLC as previously described to yield a white solid (79 mg). $^1$H-NMR was consistent with the proposed structure.

Analysis calculated for $C_{21}H_{22}N_6O_7Cl_2 \cdot 1.5$ TFA: C, 40.46; H, 3.32; N, 11.80. found: C, 40.12; H, 3.57; N, 12.26.

EXAMPLE 22

Preparation of N-[[(4,5,-dihydro-1H-imidazol-2-yl)amino]-2-methoxy-3-pyridinyl]carbonyl]glycyl-3-(3,5-dichloro-2-hydroxyphenyl)-β-alanine, (trifluoroacetate) salt

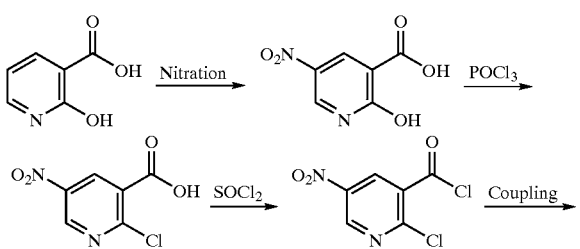

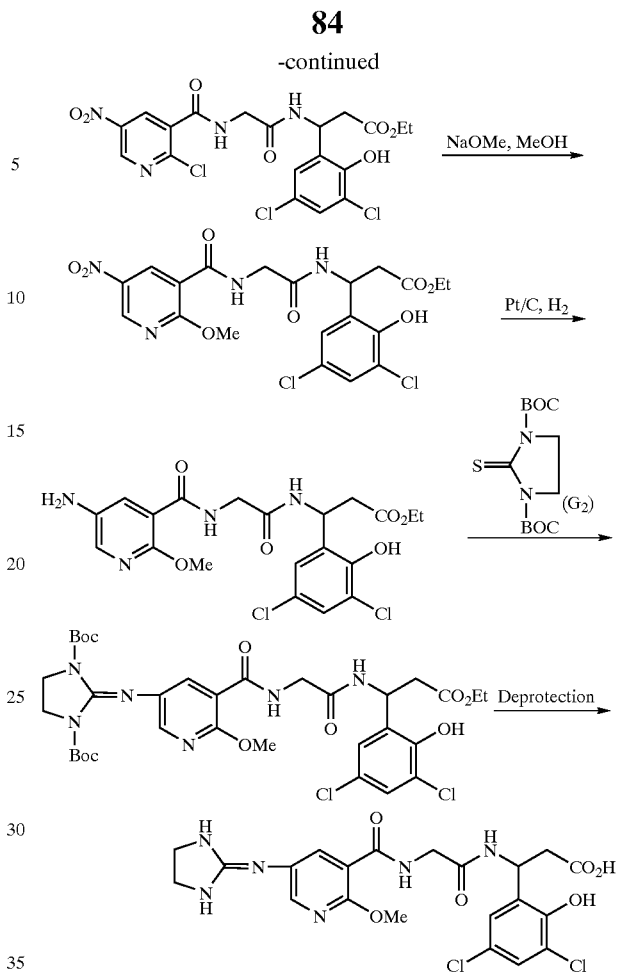

Step 1

To a solution of 2-hydroxynicotinic acid (10.0 g, 71.9 mmol) in concentrated sulfuric acid (28.6 ml), was added fuming nitric acid (7.1 ml) in a dropwise fashion. The reaction mixture was heated at 55° C. for 4 hours. The cooled reaction mixture was poured onto ice-water. The product precipitated as a yellow solid. The precipitated solid was collected by filtration, washed with water, and air dried to yield the desired product (7.2 g, 54% yield). NMR was consistent with the proposed structure.

Step 2

A solution of the product of Step 1 (5.0 g, 27.2 mmol) in phosphorus oxychloride (13.5 g) was refluxed for 4.5 hours. The cooled reaction mixture was poured onto ice water (200 g). The resulting mixture was stirred for 30 minutes and extracted with tetrahydrofuran/ethyl acetate (2/1). The organic layer was washed with brine, dried over $Na_2SO_4$, and filtered. The filtrate was concentrated to give an oil. The oil was treated with a mixture of hexane/ether (4/1) to give the desired product as a fine yellow powder (5.0 g, 91% yield). NMR was consistent with the proposed structure.

Step 3

A solution of the product of Step 2 (3.1 g, 15.3 mmol) in thionyl chloride (8.1 ml) was refluxed for 4.5 hours. The remaining thionyl chloride was removed from the reaction mixture under reduced pressure to give a pale brown oil. This oil was dried under vacuum to give the product as a yellow solid (2.7 g, 79% yield). NMR was consistent with the proposed structure.

Step 4

Diisopropylethylamine (3.7 g, 4.9 ml) was added to a solution of the product of Example D (5.5 g, 14.8 mmol) in N,N-dimethylacetamide (40 ml) and tetrahydrofuran (15 ml) and the reaction mixture cooled to −5° C. A solution of the product of Step 3 (3.1 g, 14.1 mmol) in tetrahydrofuran (25 ml) was added to the reaction over 15 minutes. The reaction was stirred at −5° C. for 30 minutes and allowed to warm to room temperature. After 3 hours, tetrahydrofuran was removed from the reaction mixture under reduced pressure. The reaction mixture was poured onto ice-water. The precipitated solid was collected by filtration, washed with water, and dried in air to give the product as a yellow solid (6.2 g, 85% yield). NMR was consistent with the proposed structure.

Step 5

A solution of the product of Step 4 (4.0 g, 7.7 mmol) and sodium methoxide (1.67 g, 30.8 mmol) in methanol (45 ml) was stirred at 0° C. for 4 hours. The reaction was neutralized with acetic acid. Methanol was removed from the reaction mixture and the crude mixture was purified by chromatography (silica gel, ethyl acetate-toluene, 6/4) to give the desired product as a yellow solid (2.5 g, 67% yield). NMR was consistent with the proposed structure.

Step 6

A mixture of the product of Step 5 (0.99 g, 1.9 mmol), 3% platinum on carbon, and methanol was treated with $H_2$ gas under 5 psi at room temperature for 16 hours. Platinum catalyst was removed by filtration. Methanol was removed under reduced pressure to give the desired product as a yellow solid (0.62 g, 70% yield). This was used in the next reaction without further purification. NMR was consistent with the proposed structure.

Step 7

A mixture of the product of Step 6 (0.26 g, 0.54 mmol), $G_2$ (0.18 g, 0.59 mmol), triethylamine (0.25 g, 1.78 mmol), mercury(II) chloride (0.16 g, 0.59 mmol), and N,N-dimethylformamide (15 ml) was heated at 90–5° C. for 16 hours. The cooled reaction mixture was filtered through a short celite column with ethyl acetate (40 ml) and then dichloromethane (30 ml). The crude mixture was chromatographed (silica gel, $CH_2Cl_2$—$CH_3OH$—$NH_4OH$, 95/5/0.5) to give the product as a yellow solid (0.31 g, 76% yield). NMR was consistent with the proposed structure.

Step 8

A solution of the product of Step 7 (0.31 g, 0.41 mmol), trifluoroacetic acid (3.5 ml), and dichloromethane (7.0 ml) was stirred at room temperature for 2 hours. Trifluoroacetic acid and dichloromethane were removed under reduced pressure and the crude mixture was treated with methanol (5 ml) and sodium hydroxide solution (2N, 2.5 ml) for 18 hours at room temperature. Acetic acid was added to netrualize sodium hydroxide. Methanol was removed to give a crude mixture. The crude mixture was purified using reverse phase HPLC to give the above compound as a white solid (0.10 g, 36% yield).

Analysis calculated for $C_{21}H_{22}N_6O_6Cl_2 \cdot 1.3CF_3COOH \cdot 0.25H_2O$: C, 41.80; H, 3.54; N, 12.39; Cl, 10.46. Found: C, 42.12; H, 3.84; N, 11.87; Cl, 10.99.

EXAMPLE 23

Preparation of N-[[5-(4,5,-dihydro-1H-imidazol-2-yl)amino]-1,2-dihydro-2-oxo-3-pyridinyl]-carbonyl]glycyl-3-(3,5-dichloro-2-hydroxyphenyl)-β-alanine, (trifluoroacetate) salt

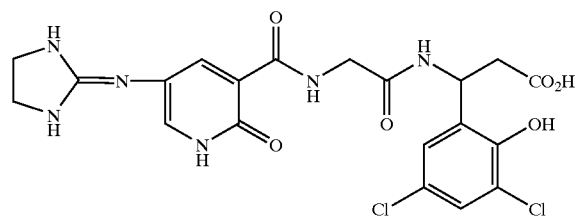

A solution of the product (0.21 g, 0.28 mmol) of Step 7, Example 22, in dioxane (4 ml) was treated with 6N HCl (6 ml) at room temperature for 72 hours. The solvent was removed under reduced pressure and the crude mixture purified on a reverse phase HPLC using acetonitrile-water as eluent to give the desired compound as an off white solid (0.052 g, 27% yield).

Analysis calculated for $C_{20}H_{20}N_6O_6Cl_2 \cdot 1.6CF_3COOH$: C, 40.17; H, 3.14; N, 12.11; found: C, 40.10; H, 3.22; N, 11.84.

EXAMPLE 24

Preparation of N-[[(4,5-dihydro-1H-imidazol-2-yl)amino]-1-methyl-1H-pyrazol-3yl]carbonyl]glycyl-3-(3,5-dichloro-2-hydroxyphenyl)-β-alanine, (trifluoroacetate) salt

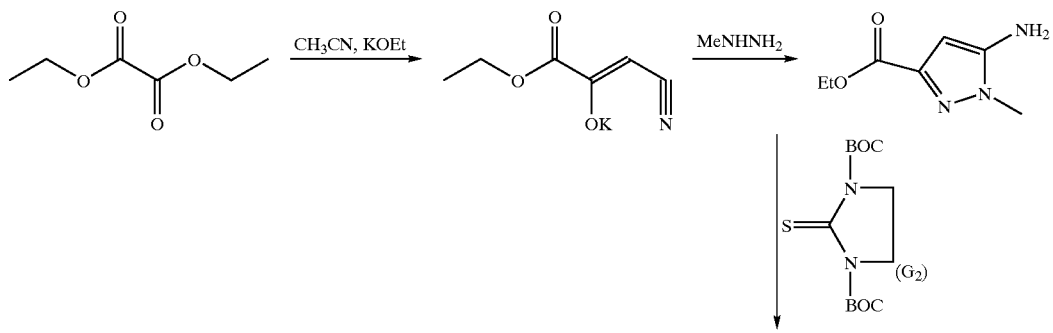

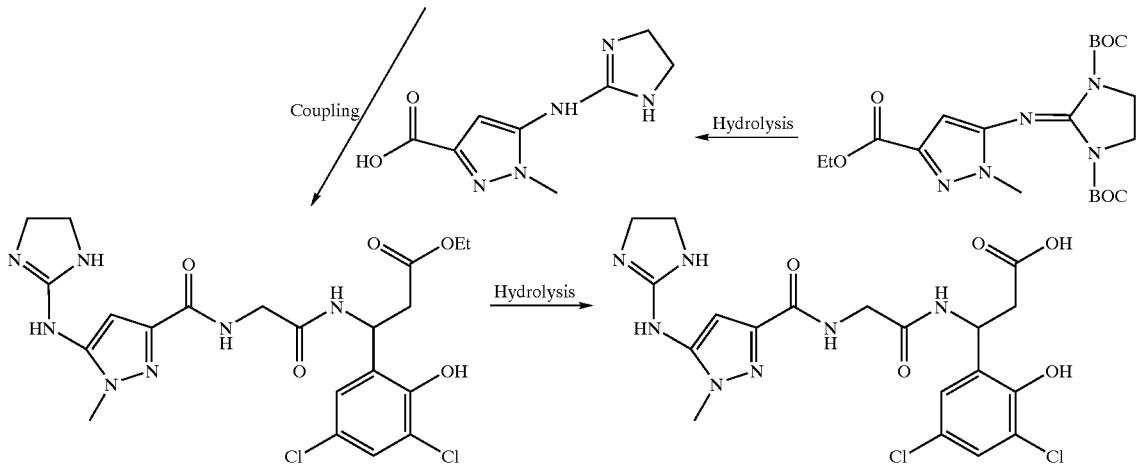

The Steps 1 and 2 in the synthesis of the target compound were carried out following the literature procedures (Justus Liebigs. Ann. Chem, 512, 97, 1934 and J. Heterocyclic Chem. 21, 737, 1994 respectively).

Step 3

To a solution of the product of Step 2 (0.9 g, 5.3 mmol) and $G_2$ (1.9 g, 5.9 mmol) in DMF (25 ml), triethylamine (2.5 ml, 17.6 mmol) and mercuric chloride (1.6 g, 5.9 mmol) were added. After heating the mixture at 80–85° C. for 18 hours, the reaction mixture was cooled and filtered through a celite column. The residue was washed with methylene chloride and the combined fractions concentrated. The residue was redissolved in methylene chloride and washed with water and brine. After drying over sodium sulfate, the mixture was filtered and concentrated. The crude orange solid (1.8 g) was purified using silica gel chromatography (hexane/ethyl acetate 1/1) to give the N-Boc protected product as an off-white solid (1.4 g).

Step 4

To a solution of the product of Step 3 (2.4 g, 5.5 mmol) in ethanol (50 ml), aqueous lithium hydroxide (526 mg in 5 ml water) was added. The reaction mixture was stirred at room temperature for 24 hours. Acetic acid (22 ml) was added to the reaction and the mixture stirred for 15 miniutes. After removal of the solvent under reduced pressure, the crude mixture was purified on a reverse phase HPLC (acetonitrile/water containing trifluoroacetic acid) to give the product as a TFA salt as a thick white liquid. The residue was treated with hydrogen chloride (4M solution in dioxane) and stirred for 10 minutes. The reaction was concentrated to remove the solvent and the process repeated twice to give the desired product as a white solid (3.9 g). The product was used in the next Step without further purification.

Step 5

To a solution of the of the product of Step 4 (0.9 g, 3.7 mmol) in DMF (15 ml) at 0° C., N-methylmorpholine (605 ml, 5.5 mmol) and isobutyl chloroformate (475 ml, 3.7 mmol) were added sequentially. After stirring for 5 minutes, a solution of the product of Step D in DMF (10 ml) containing N-methylmorpholine (605 ml, 5.5 mmol) was injected into the reaction. The mixture was allowed to stir at 0° C. for 1 hour and at room temperature for 36 hours. The solvent was removed under reduced pressure and the residue purified on a reverse phase HPLC (acetonitrile/water containing trifluoroacetic acid) to give the product (525 mg) as a TFA salt.

Step 6

To a solution of the product of Step 5 (540 mg, 1 mmol) in ethanol (50 ml), aqueous lithium hydroxide (144 mg in 10 ml water) was added. The reaction mixture was stirred at room temperature for 24 hours. Acetic acid (305 ml) was added to the reaction and the mixture stirred for 15 minutes. After removal of the solvent under reduced pressure, the crude mixture was purified on a reverse phase HPLC (acetonitrile/water containing trifluoroacetic acid) to give the desired product (486 mg, 75% yield) as a TFA salt.

Analysis calculated for $C_{19}H_{21}N_7O_5Cl_2 \cdot 1.5CF_3CO_2H$: C, 39.48; H, 3.39; N, 14.65. Found: C, 39.29; H, 3.14; N, 14.72.

NMR and MS were consistent with the desired structure.

EXAMPLE 25

Preparation of N-[[5-[(4,5-dihydro-1H-imidazol-2-yl)amino]-1H-pyrazol-3-yl]carbonyl]-glycyl-3-(3,5-dichloro-2-hydroxyphenyl)-β-alanine, (trifluoroacetate) salt

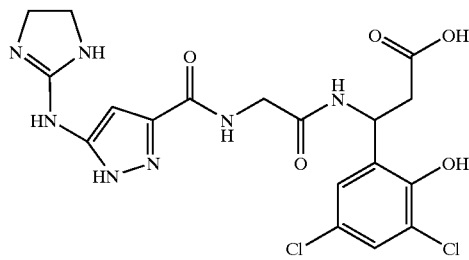

The compound was synthesized as in the Example 24 utilizing benzylhydrazine instead of methylhydrazine in Step 2. The resulting N-benzyl pyrazole compound was deprotected in the last Step using catalytic hydrogenation conditions (5% Pd/C, 20 psi, room temperature, 26 hours). This reaction was carried out using acetic acid-trifluoroacetic acid (4/1) as the solvent.

Analysis calculated for $C_{18}H_{19}N_7O_5Cl_2 \cdot 1.75CF_3CO_2H \cdot 1.25H_2O$: C, 36.56; H, 3.32; N, 13.88. found: C, 36.35; H, 2.96; N, 14.28.

NMR and MS were consistent with the desired structure.

EXAMPLE 26

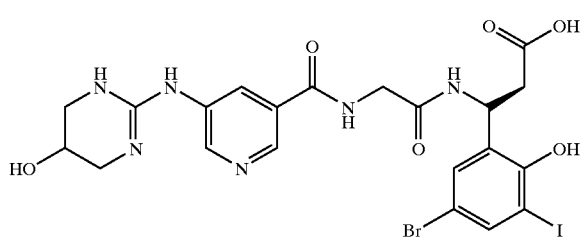

The above compound was prepared as described in Example 9 except the product of Example S was used instead of the product of Example R in Step 4.

Analysis calculated for $C_{21}H_{22}BrIN_6O_6 \cdot 2\ CF_3COOH \cdot 0.25\ H_2O$ C, 33.60; H, 2.76; N, 9.40. Found C, 34.23; H, 2.35; N, 9.72.

EXAMPLE 27

Step 1
A solution of the starting material (1.4 g) in ethanol (50 ml) was treated with a catalytic amount of 5% Pt/C under 5 psi pressure of hydrogen at room temperature for 5 hours. The reaction mixture was filtered, concentrated, and dried to afford a white solid (1.1 g). $^1$H-NMR was consistent with the proposed structure.

Step 2
The compound 2 was prepared by following the experimental procedure given in Step 4 of Example 21. $^1$H-NMR was consistent with the proposed structure.

Step 3
The ester group of compound 2 was hydrolyzed following the experimental procedure given in Step 5 of Example 21. $^1$H-NMR was consistent with the proposed structure.

Analysis calculated for $C_{22}H_{24}N_6O_7Cl_2 \cdot 1.50\ TFA \cdot 0.25\ H_2O$: C, 41.08; H, 3.59; N, 11.50. Found: C, 41.03; H, 3.69; N, 11.45.

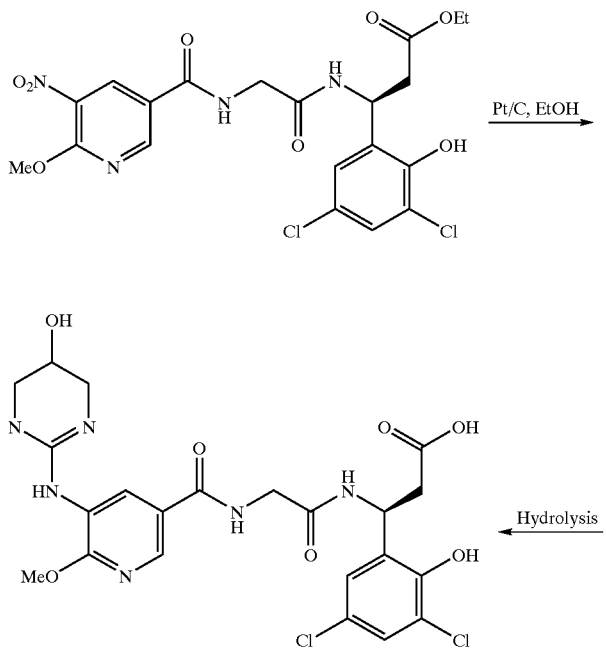

The starting material needed in this preparation was synthesized utilizing the procedure of Example 21, Step 1.

EXAMPLE 28

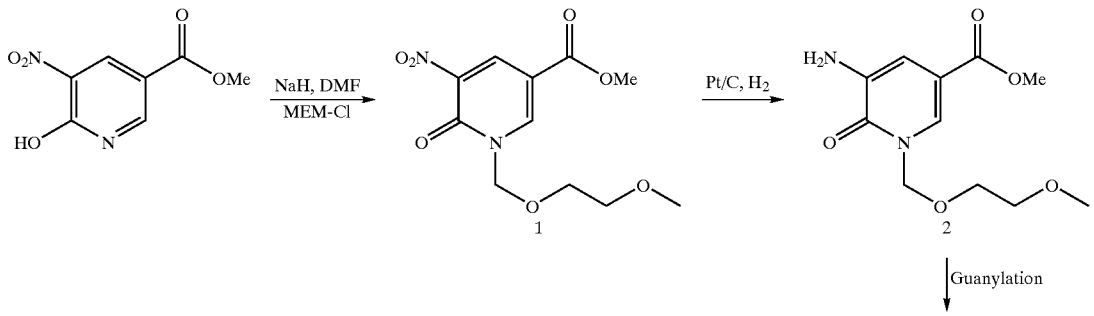

-continued

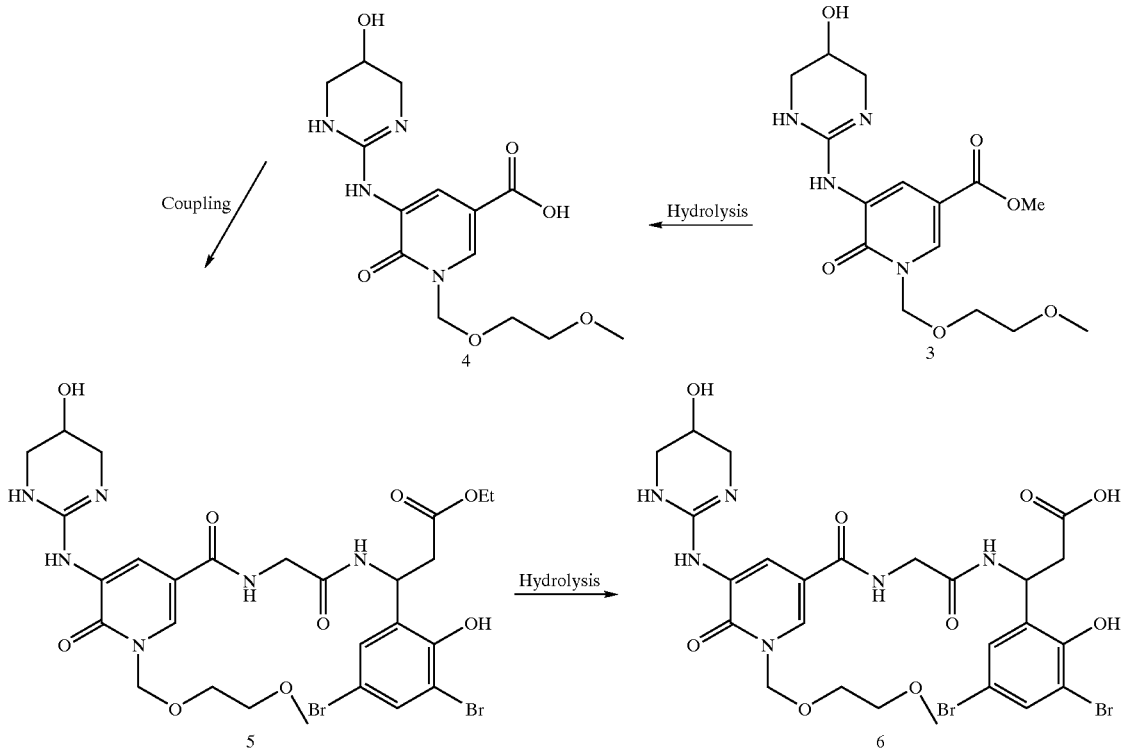

The starting material needed in this preparation was prepared as described in Step 1, Example 18.

Step 1

The compound 1 was prepared following the procedure given in Step 2 of Example 18 except that 2-methoxyethoxymethyl chloride was used as the alkylating agent instead of iodomethane. $^1$H-NMR was consistent with the proposed structure.

Step 2

A solution of the product described in Step 1 (4.6 g) in methanol (50 ml) was treated with a catalytic amount of 5% Pt/C under 5 psi pressure of hydrogen at room temperature for 2 hours. The reaction mixture was filtered, concentrated and dried to afford a viscous oil (4.3 g). $^1$H-NMR was consistent with the proposed structure.

Step 3

A portion of the product of Step 2 (2.0 g) was guanylated using the reaction conditions described in Step 4 of Example 21 to afford the product 3 as a viscous golden oil (890 mg). $^1$H-NMR was consistent with the proposed structure.

Step 4

The ester group from the product 3 was hydrolyzed using the experimental procedure given in Step 5 of Example 21. $^1$H-NMR was consistent with the proposed structure.

Step 5

The product of Step 4 was coupled to the product of Example I following the procedure given in Step 4 of Example 12. $^1$H-NMR was consistent with the proposed structure.

Step 6

The ester group from the product of Step 5 was hydrolyzed following the procedure given in Step 5 of Example 21. $^1$H-NMR was consistent with the proposed structure.

Analysis calculated for $C_{25}H_{31}N_6O_9Br_2 \cdot 1.75TFA \cdot 0.25 H_2O$: C, 37.07; H, 3.63; N, 9.10. Found: C, 36.86; H, 3.66; N, 9.39.

EXAMPLE 29

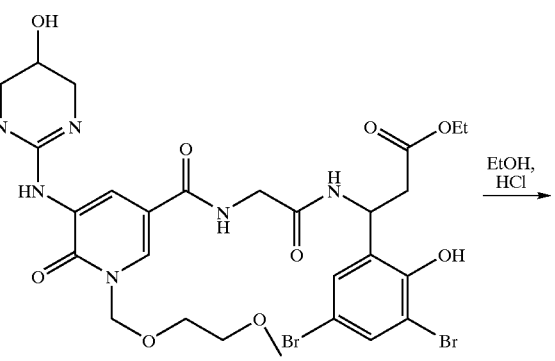

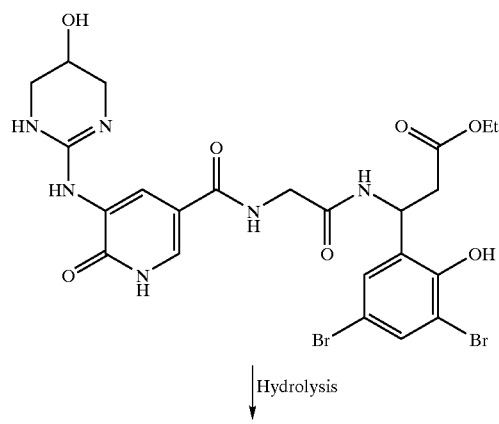

-continued

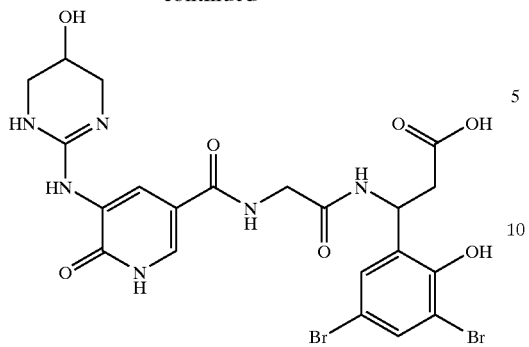

The product of Step 5 of Example 28 was used as the starting material in this procedure.

Step 1

A portion (425 mg) of the starting material was treated with saturated anhydrous HCl in ethanol (10 ml) at room temperature for four hours. The reaction mixture was concentrated to dryness and the product was used in the next step without purification.

Step 2

The ester group from the crude product of Step 1 was hydrolyzed following the procedure in Step 5 of Example 21. $^1$H-NMR was consistent with the proposed structure.

Analysis calculated for $C_{21}H_{22}N_6O_7Br_2 \cdot 1.75TFA \cdot 0.25 H_2O$: C, 35.27; H, 2.93; N, 10.07. Found: C, 35.21; H, 3.16; N, 10.27.

EXAMPLE S

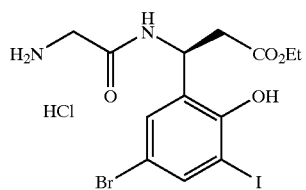

The above compound was prepared following the procedures described for Example G,. In step 2A, 3-iodo-5-bromosalicylaldehyde was used instead of 3,5-dichlorosalicylaldehyde.

EXAMPLE T

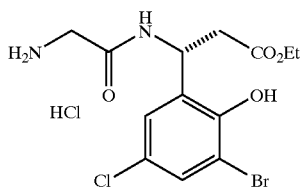

The above compound was prepared following the procedures described for Example G. In step 2A, 3-bromo-5-chlorosalicylaldehyde was used instead of 3,5-dichlorosalicylaldehyde. Similarly, in step 2B, R-phenylglycinol was used instead of S-phenylglycinol.

EXAMPLE U

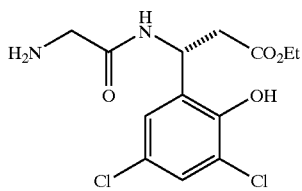

The above compound was prepared following the procedures described for Example D. The racemic mixture obtained in step 2 was resolved as described below.

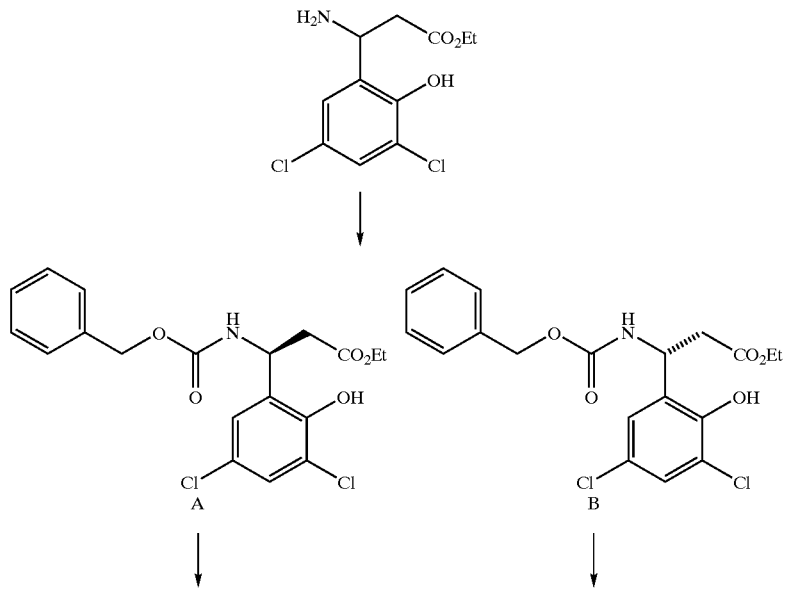

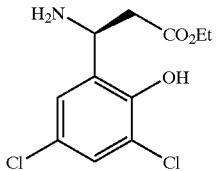

Step 1

To the racemic amino ester hydrochloride (50.0 g, 158.9 mmol) obtained from Step 2, example D, in CH$_2$Cl$_2$ (500 mL) and water (380 mL) was added NaHCO$_3$ (38.2 g, 454.5 mmol). The mixture was stirred at room temperature for 10 minutes with vigorous gas evolution. A solution of benzyl chloroformate (43.4 g, 222.8 mmol) in CH$_2$Cl$_2$ (435 mL) was added over 20 minutes with rapid stirring. After 40 minutes, the reaction mixture was poured into a separatory funnel and the organic solution collected. The aqueous phase was washed with CH$_2$Cl$_2$(170 mL). The combined organic solution was dried (MgSO$_4$) and concentrated in vacuo. The resulting gummy solid was triturated with hexane and collected by filtration. The tan solid was dried in vacuo to give the desired racemic product, (62.9 g, 96%. yield). This material was subjected to reverse phase HPLC using a chiral column to give each pure enantiomer, A and B. The column employed was a Whelk-O (R,R), 10 micron particle size using a 90:10 heptane:ethanol mobile phase. Optical purity was determined to be >98% using analytical HPLC with similar solvent and conditions. $^1$H NMR was consistent with proposed structure.

Step 2A

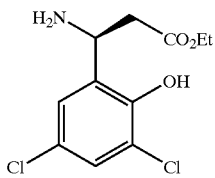

To a solution of Enantiomer A, Step 1 (57.9 g, 140.4 mmol) in CH$_2$Cl$_2$(600 mL) was added trimethylsilyl iodide (33.7 g, 168.5 mmol) in CH$_2$Cl$_2$ (125 mL) via canula. The orange solution was stirred at room temperature for 1 hour. Methanol (27.3 mL, 674.1 mmol) was added dropwise and the solution stirred for 15 minutes. The reaction solution was concentrated in vacuo to give an orange oil. The residue was dissolved in methyl t-butyl ether (670 mL) and extracted with 1M HCl (420 mL) and water (1×230 mL, 1×130 mL). The aqueous extracts were back washed with MTBE (130 mL). To the aqueous solution was added solid NaHCO$_3$ (52.9 g, 630 mmol) in small portions. The basified aqueous mixture was extracted with MTBE (1×1.2 L, 2×265 mL). The combined organic solution was washed with brine and concentrated in vacuo to give the desired product, (28.6 g, 73% yield). $^1$H NMR was consistent with proposed structure.

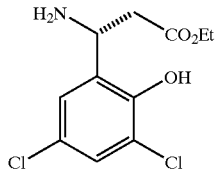

Step 2B

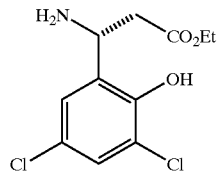

To a solution of the Enantiomer B, Step 1, the compound of Example 1 (38.5 g, 93.4 mmol) in CH$_2$Cl$_2$ (380 mL) was added trimethylsilyl iodide (25.0 g, 125.0 mmol) in CH$_2$Cl$_2$ (80 mL) via canula. The orange solution was stirred at room temperature for 1.5 hours. Methanol (20.0 mL, 500.0 mmol) was added dropwise and the solution stirred for 20 minutes. The reaction solution was concentrated in vacuo to give an orange oil. The residue was dissolved in diethyl ether (450 mL) and extracted with 1M HCl (320 mL) and water (1×200 mL, 1×100 mL). The aqueous extracts were back washed with diethyl ether (100 mL). To the aqueous solution was added solid NaHCO$_3$ (40.1 g, 478 mmol) in small portions. The basified aqueous mixture was extracted with diethyl ether (1×1.0 L, 2×200 mL). The combined organic solution was washed with brine and concentrated in vacuo to give the desired product (20.8 g, 80% yield).

Anal. calculated for C$_{11}$H$_{13}$Cl$_2$NO$_3$: C, 47.50; H, 4.71; N, 5.04. Found: C, 47.11; H, 4.66; N, 4.93.

The product of step 2B was converted to the target intermediate by using the reagents and conditions described in steps 4 and 5 of example G.

EXAMPLE V

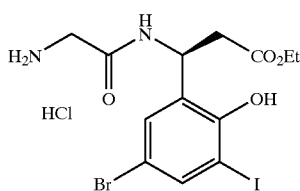

The above compound was prepared following the procedures described in Example G. In step 2A, 5-bromo-3-iodobenzaldehyde was used instead of 3,5-dichlorosalicylaldehyde.

EXAMPLE 30

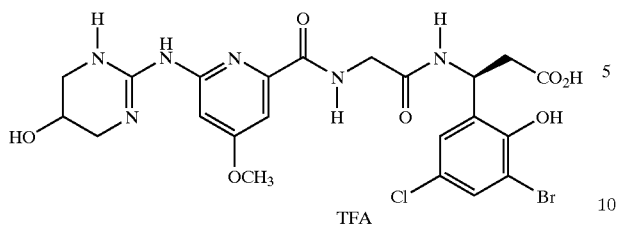

Step 1

Preparation of

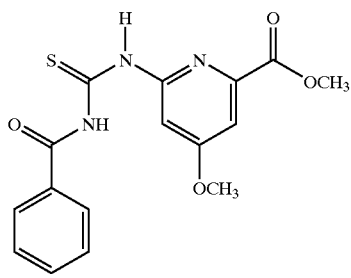

To a stirred solution of methyl 4-methoxy-2-aminopicolinate (602 mg, 3.3 mmol) (JACS, 78, 4130, 1956) in $CH_2Cl_2$ (20 ml), was added benzoylisothiocyanate (1 ml, Aldrich), and the reaction mixture was stirred at room temperature for 90 minutes. The mixture was diluted with ether (20 ml). The mixture was cooled in an ice bath and solid was filtered and washed with ether and dried to give the desired compound (828 mg, 73.27% yield) as white solid: $^1$H NMR: 300 MHz was consistent with proposed structure

Step 2

Preparation of

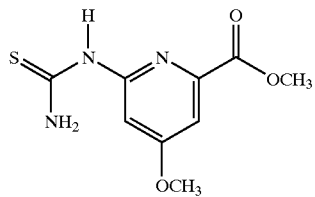

To a stirred solution of the product of Step 1 (750 mg, 2.17 mmol) in methanol (30 ml), under nitrogen atmosphere was added NaOMe (538 mg). The reaction mixture was stirred at room temperature for 2 hours. The mixture was quenched with glacial acetic acid (0.575 ml), and was stirred at room temperature for 15 minutes. The solid was filtered under vacuum, washed with cold methanol and dried to give the desired compound (385 mg, 73% yield) as white solid: $^1$H NMR: 300 MHz was consistent with proposed structure.

Step 3

Preparation of

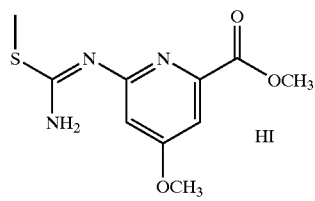

To a stirred solution of the product of Step 2 (364 mg, 1.5 mmol) in methanol (20 ml), was added iodomethane (0.25 ml). The reaction mixture was heated to reflux for 2 hours. The mixture was cooled to room temperature and was concentrated to give the desired compound (560 mg) as white solid: $^1$H NMR: 300 MHz was consistent with proposed structure.

Step 4

Preparation of

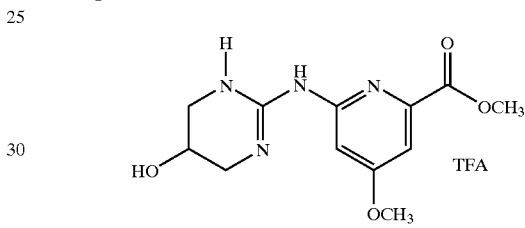

To a stirred solution of the product of Step 3 (500 mg, 1.30 mmol) in N,N-dimethylacetamide (10 ml), was added 1,3-diamino-2-hydroxypropane (123 mg, 1.37 mmol). The reaction mixture was heated to 90° C. for 2 hours. The mixture was concentrated in vacuo to give the crude product which was purified by reverse phase HPLC to give the desired compound (228 mg) as white solid. $^1$H NMR: 300 MHz was consistent with proposed structure.

Step 5

Preparation of

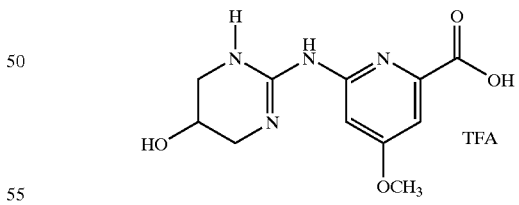

To a stirred solution of the product of Step 4 (200 mg) in methanol (3 ml), and THF (3 ml), was added 1N NaOH solution (3 ml). The reaction mixture was stirred at room temperature for 1 hour. The mixture was concentrated in vacuo to yield an oily gum which was taken up in water (2 ml), and was neutralized with 1N HCl (3 ml). The mixture was concentrated in vacuo to give the crude product which was purified by reverse phase HPLC to give the desired compound (228 mg) as white solid. $^1$H NMR: 300 MHz was consistent with the proposed structure.

Step 6
Preparation of

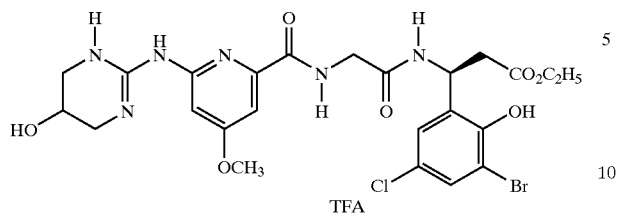

To a stirred solution of the product of Step 5 (151.25 mg, 0.5 mmol) in N,N-dimethylacetamide (5 ml) was added 4-methylmorpholine (202 mg, 2 mmol), and 1-hydroxybenzotriazole (67 mg, 0.5 mmol), and, the amino ester product of Example R (208.5 mg, 0.5 mmol). The mixture was stirred at room temperature for 5 minutes. The reaction mixture was treated with 1-[3-(dimethylamino)propyl-3-ethylcarbodiimide (96 mg, 0.5 mmol), and 4-(dimethylamino)pyridine (10 mg). The reaction mixture was stirred at room temperature under nitrogen atmosphere for 72 hours. The reaction mixture was quenched with water (1 ml) and concentrated in vacuo to give the crude product which was purified by reverse phase HPLC to give the desired compound (42 mg) as white solid. $^1$H NMR: 400 MHz was consistent with the proposed structure.

Step 7
Preparation of

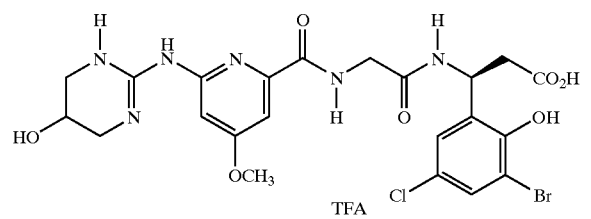

To a stirred solution of the product of Step 6 (35 mg) in methanol (3 ml), and THF (3 ml), was added 1N NaOH solution (3 ml). The reaction mixture was stirred at room temperature for 1 hour. The mixture was concentrated in vacuo to yield an oily gum which was taken up in water (2 ml), and neutralized with 1N HCl (3 ml). The mixture was concentrated in vacuo to give the crude product which was purified by reverse phase HPLC to give the desired compound (22 mg) as a white solid. $^1$H NMR: 400 MHz was consistent with the proposed structure.

Analysis Calculated for: $C_{22}H_{24}N_6O_7BrCl\cdot2TFA$, $0.5H_2O$: C, 37.22; H, 3.25; N, 10.04. Found: C, 36.91; H, 3.17; N, 10.02.

EXAMPLE 31

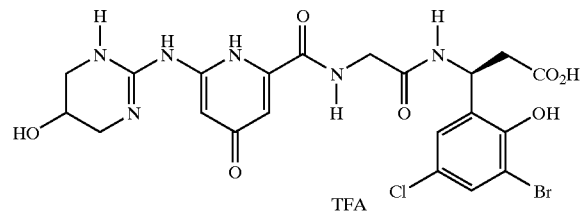

Step 1
Preparation of

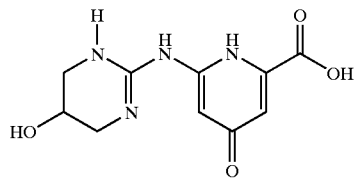

To a stirred solution of the product of Step 4 of Example 30 (900 mg) in glacial acetic acid (10 ml) was added 48% HBr (10 ml). The reaction mixture was heated to reflux for 3 hours The mixture was cooled to room temperature and stirred at room temperature for 18 hours. The mixture was concentrated in vacuo to give the crude product which was purified by reverse phase HPLC to give the desired compound (720 mg) as an oily gum. $^1$H NMR: 300 MHz was consistent with the proposed structure.

Step 2
Preparation of

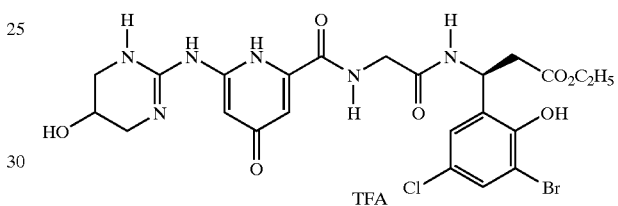

To a stirred solution of the product of Step 1 (720 mg, 1.7 mmol) in N,N-dimethylacetamide (10 ml) was added 4-methylmorpholine (520 mg, 5.2 mmol), and 1-hydroxybenzotriazole (221 mg, 1.71 mmol), and the amino ester product of Example R (710 mg, 1.71 mmol). The mixture was stirred at room temperature for 5 minutes. The reaction mixture was treated with 1-[3-(dimethylamino)propyl-3-ethylcarbodiimide (211 mg, 1.7 mmol), and 4-(dimethylamino)pyrdine (10 mg). The reaction mixture was stirred at room temperature under nitrogen atmosphere for 72 hours. The reaction mixture was quenched with water (1 ml) and concentrated in vacuo to give the crude product which was purified by reverse phase HPLC to give the desired compound (182 mg) as white solid. $^1$H NMR: 300 MHz was consistent with the proposed structure.

Step 3
Preparation of

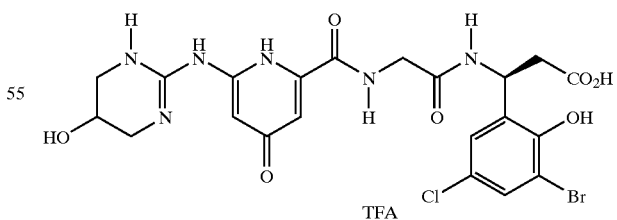

To a stirred solution of the product of Step 2 (100 mg) in methanol (3 ml), and THF (3 ml), was added 1N NaOH solution (3 ml). The reaction mixture was stirred at room temperature for 1 hour. The mixture was concentrated in vacuo to yield an oily gum which was taken up in water (2 ml), and neutralized with 1N HCl (3 ml). The mixture was concentrated in vacuo to give the crude product which was purified by reverse phase HPLC to give the desired compound (42 mg) as a white solid. $^1$H NMR: 300 MHz was consistent with the proposed structure.

Analysis Calculated for $C_{21}H_{22}N_6O_7BrCl \cdot 1.5TFA$, $0.5H_2O$: C, 37.64; H, 3.22; N, 10.97. Found: C, 37.56; H, 3.05; N, 10.99.

EXAMPLE 32

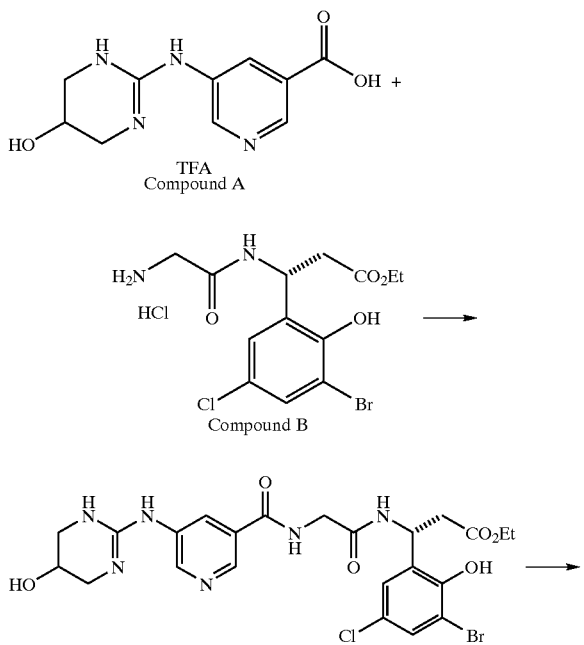

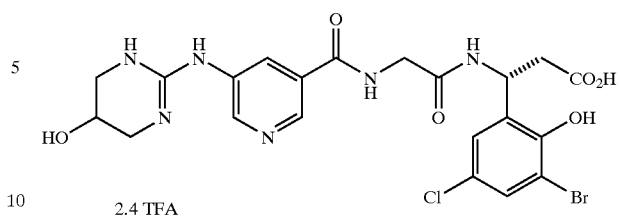

2.4 TFA

To a solution of the product of Step 3, Example 9 (860 mg, 2.45 mmol) and the product of Example T (1.0 g, 2.41 mmol) in dimethylacetamide (24 mL) at 0° C. was added HOBT (358 mg, 2.64 mmol) followed by N-methylmorpholine (0.6 mL, 5.15 mmol). The reaction solution was stirred for 15 minutes and EDC (470 mg, 2.45 mmol) was added. The mixture was warmed to room temperature overnight. The mixture was concentrated in vacuo and the residue partitioned between ethyl acetate and water. The aqueous solution was extracted with ethyl acetate and the combined organic layers were dried ($Na_2SO_4$) and concentrated. The residue was purified by RP HPLC (90:10 water/TFA:MeCN starting gradient, retention time 22.5 min) to give the desired coupled product along with recovered Compound B (480 mg). This material (compound B) was treated with 1M aqueous NaOH (6 mL) and stirred for 3 hours. The solution was acidified to pH 4 with TFA. The mixture was purified by RP HPLC (95:5 water/TFA:MeCN starting gradient, retention time 24.5 min) to give the desired product (160 mg, 8% yield for the two steps).

Analysis calculated for: $C_{21}H_{22}BrClN_5O_6 + 2.4$ TFA: C, 36.74; H, 2.92; N, 9.96. Found: C, 36.83; H, 3.07; N, 9.88.

$^1$H NMR was consistent with the proposed structure.

EXAMPLE 33

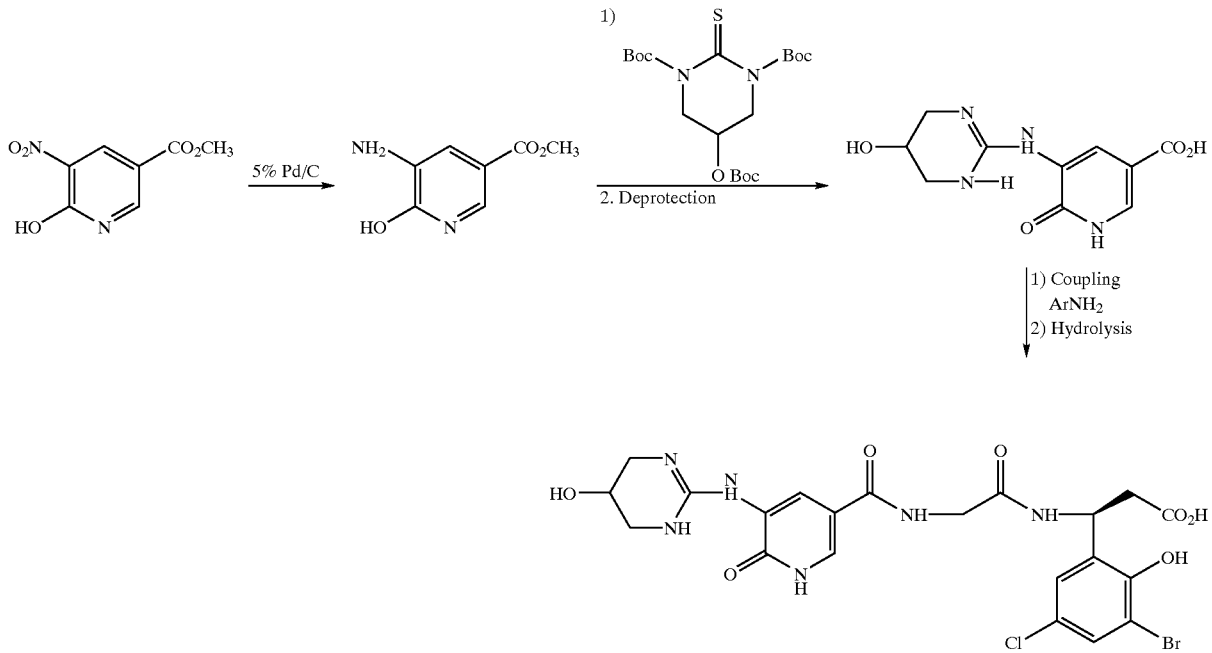

Step 1

A solution of the material from Step 2, Example 18 (5.72 g) in THF (80 ml) was treated with a catalytic amount of 5% Pd/C under a 5 psi atmosphere of hydrogen at room temperature for 2 hours. The reaction mixture was filtered and the residue washed with DMF (250 ml). The filtrate was concentrated and the residue treated with ether, filtered, and air dried to afford a brown powder (4.9 g) which was used directly in the next step without further purification. $^1$H-NMR was consistent with the proposed structure.

Step 2

The material from Step 1 (500 mg) was guanylated using the tris boc reagent and the conditions described in Step 4 of Example 21 to afford the desired product (128 mg) as a golden glass. $^1$H-NMR was consistent with the proposed structure.

Step 3

The ester group from the product of Step 2 was hydrolyzed using the experimental procedure given in Step 5 of Example 21. $^1$H-NMR was consistent with the proposed structure.

Analysis calculated for: $C_{11}H_{14}N_4O_4 \cdot 1.5TFA$ C, 38.45; H, 3.57; N, 12.81. Found: C, 38.32; H, 3.77; N, 12.80.

Step 4

The desired compound was prepared utilizing the same methodology as described in Step 4, Example 12 by coupling the product described in Step 3 with the product of Example R. $^1$H-NMR was consistent with the proposed structure.

Step 5

The ester group from the product in Step 4 was hydrolyzed utilizing the same procedure as described in Step 5 of Example 12. $^1$H-NMR was consistent for the proposed structure.

Analysis calculated for: $C_{21}H_{22}N_6O_7BrCl \cdot 1.5TFA \cdot 0.25H_2O$ C, 37.86; H, 3.18; N, 11.04; Cl, 4.66; Br, 10.50. Found: C, 37.60; H, 3.26; N, 11.20; Cl, 4.79; Br, 10.19.

EXAMPLE 34

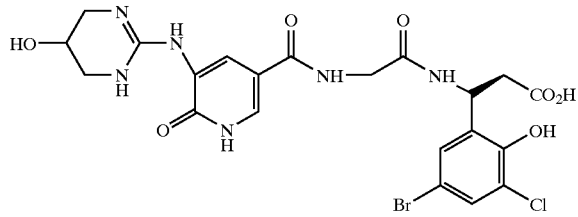

The above compound was prepared utilizing the methodology described in Example 33. In Step 4, the product of Example H was used instead of the product of Example R.

Analysis calculated for: $C_{21}H_{22}N_6O_7BrCl \cdot 2.0TFA \cdot 0.5H_2O$ C, 36.49; H, 3.06; N, 10.21. Found C, 36.10, H, 2.83; N, 10.29.

EXAMPLE 35

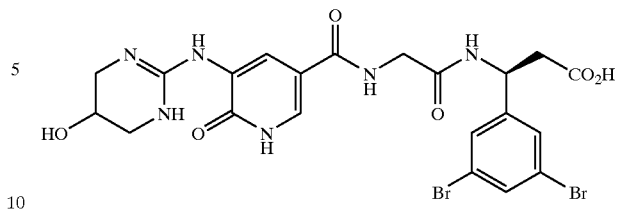

The above compound was prepared utilizing the methodology described in Example 33. In Step 4, the product of Example V was used instead of the product of Example R.

Analysis calculated for: $C_{21}H_{22}N_6O_6Br_2 \cdot 1.75TFA$. C, 35.76; H, 3.03; N, 10.21. Found: C, 35.58; H, 3.07; N, 10.61.

EXAMPLE 36

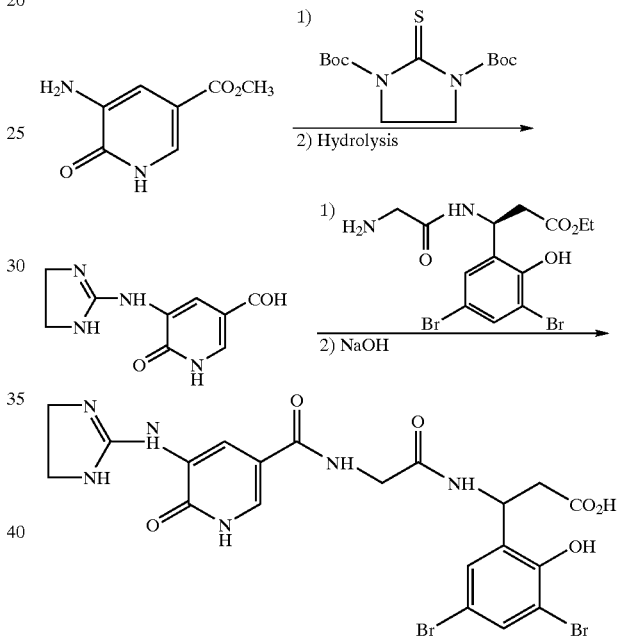

Step 1

The product from Step 1 of Example 33 (261 mg) was guanylated using the bis-boc reagent $G_2$ and the reaction conditions described in Step 5 of Example 18 to afford the product as a white solid (207 mg). This material was then saponified using the experimental conditions described in Step 5, Example 21. The $^1$H-NMR was consistent with the proposed structure.

Step 2

The desired compound was prepared utilizing the same methodology as described in Step 4 of Example 12. The product described in Step 1 was coupled with the product of Example I. $^1$H-NMR was consistent with the proposed structure.

Step 3

The ester group from the product in Step 2 was hydrolyzed utilizing the same procedure as described in Step 5 of Example 12. $^1$H-NMR was consistent with the proposed structure.

Analysis calculated for $C_{20}H_{20}N_6O_6Br_2 \cdot 1.75TFA \cdot 0.25H_2O$ C, 35.10; H, 2.79; N, 10.45. Found: C, 34.85; H, 2.59; N, 10.62.

EXAMPLE 37

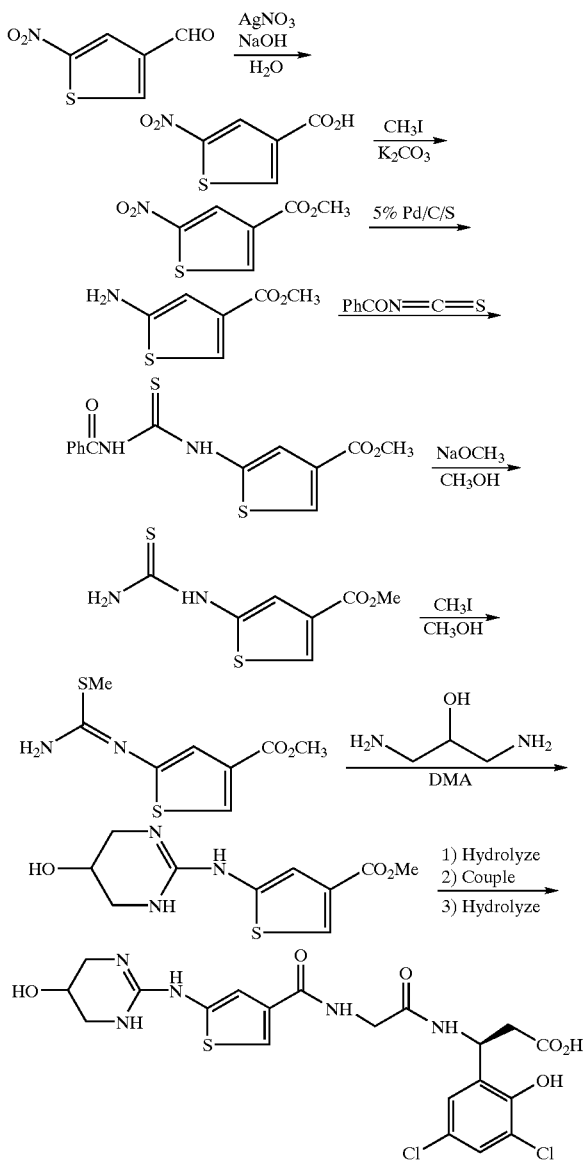

Step 1
2-nitrothiophene-4-carboxaldehyde (5.0 g) was suspended in water (100 ml) at room temperature and a solution of sodium hydroxide (5.2 g) in water (50 ml) was added in one portion. The black reaction mixture was stirred at room temperature for 1 hour and then filtered through a pad of celite. The filtrate was acidified with 1N HCl solution and then extracted with ethyl acetate. The combined organic extracts were washed with saturated sodium chloride solution, dried ($Na_2SO_4$) and concentrated to afford a light yellow solid (5.0 g) which was used without further purification. $^1$H-NMR was consistent with the proposed structure.

Step 2
The product from Step 1 (2.5 g) was stirred with potassium carbonate (2.0 g) and methyl iodide (2.2 g) in DMF (30 ml) at room temperature for 16 hours. The reaction mixture was partitioned between ethyl acetate and water and the layers separated. The aqueous portion was extracted with additional ethyl acetate and then the combined organic extracts were washed with water, saturated sodium chloride solution, dried ($Na_2SO_4$) and concentrated. The dark colored residue was purified on a silica gel column with 15% ethyl acetate-85% hexane to yield a yellow solid (950 mg). $^1$H-NMR was consistent with the proposed structure.

Step 3
The product obtained in Step 2 (2.0 g) was dissolved in methanol (50 ml) and treated with a catalytic amount of 5% Pd/C under a 50 psi atmosphere of hydrogen at 60° C. for 32 hours. The reaction was cooled and filtered and the filtrate was concentrated. The residue was purified on a silica gel column eluting with 25% ethyl acetate-75% hexane to afford a light yellow solid (920 mg). $^1$H-NMR was consistent with the proposed structure.

Step 4
A solution of the product from Step 3 (900 mg) was dissolved in ethyl acetate (20 ml) and treated with benzoyl isothiocyanate (947 mg) in one portion at room temperature. The reaction was stirred for 30 minutes and the precipitate filtered, washed with ethyl acetate and air dried to yield a light yellow solid (1.51 g). $^1$H-NMR was consistent with the proposed structure.

Step 5
The product obtained in Step 4 of Example 35 was dissolved in methanol (70 ml) and treated with sodium methoxide (1.3 g) portionwise at room temperature. The reaction was stirred for 30 minutes and then quenched with glacial acetic acid (1.4 g). The reaction was concentrated and the residue was partitioned between ethyl acetate and water. The aqueous portion was extracted with additional ethyl acetate and the combined organic extracts were washed with saturated sodium chloride solution, dried ($Na_2SO_4$) and concetrated to yield a light yellow powder (900 mg). $^1$H-NMR was consistent with the proposed structure.

Step 6
The product from Step 5 (900 mg) was dissolved in methanol (20 ml) and treated with methyl iodide (1.4 g). The reaction was refluxed for 2 hours and then cooled and concentrated. The residue was treated with ether, filtered and air dried to produce a white solid (1.27 g). $^1$H-NMR was consistent with the proposed structure.

Step 7
The product from Step 6 (1.2 g) was heated at 95–100° C. with 1,3-diamino-2-hydroxypropane (469 mg) and DMA (20ml) for 8 hours. The reaction was cooled and the solvent removed under high vacuum. The residue was purified via reverse phase HPLC eluting with a water (0.5% TFA)-acetonitrile gradient to afford the desired product (255 mg). $^1$N-NMR was consistent with the proposed structure.

Step 8
The desired compound was prepared as using the material produced in Step 7 using the conditions described in Step 5, Example 21. $^1$H-NMR was consistent with the proposed structure.

Step 9
The desired compound was prepared utilizing the same methodology as is described in Step 4 of Example 12 by coupling the product from Step 8 with the material from Example G. $^1$H-NMR was consistent with the proposed structure.

Step 10
The ester group from the product Step 9 was hydrolyzed utilizing the same procedure as described in Step 5 of Example 12. $^1$H-NMR was consistent with the proposed structure.

Analysis calculated for $C_{20}H_{21}N_5O_6C_{12}S$. 1.75TFA. C, 38.43; H, 3.19; N, 9.54; S, 4.37. Found: C, 38.43; H, 3.39; N, 9.73; S, 4.27.

EXAMPLE 38

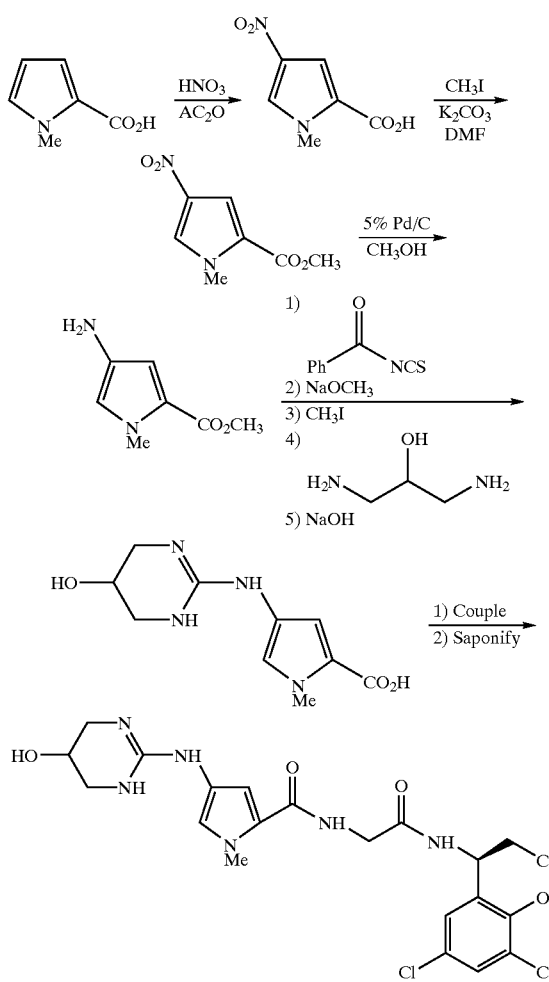

Step 1

Acetic anhydride (20 ml) was treated with 70% nitric acid (4 ml) at room temperature. This solution was then added drop wise to a stirred mixture of N-methyl pyrrole-2-carboxylic acid (5.0 g) in acetic anhydride (30 ml) at −30°. The reaction was stirred and allowed to warm to room temperature for 30 minutes. The reaction was then re-chilled to −25° and filtered through a cold filter, washed with cold hexane and air dried to afford yellow powder (1.5 g). $^1$H-NMR was consistent with the proposed structure.

Step 2

The desired compound was prepared utilizing the procedure described in Step 2, Example 37 using the product prepared in Step 1. The crude product was purified by chromatography on a silica gel column eluting with 40% ethyl acetate-hexane. $^1$H-NMR was consistent with the proposed structure.

Step 3

The product from Step 2 (1.0 g) was dissolved in methanol (25 ml) and treated with a catalytic amount of 5% Pd/C under a 5 psi atmosphere of hydrogen at room temperature for 3 hours. The reaction was filtered and concentrated to afford a deep red liquid (1.0 g) which was used without further purification. $^1$H-NMR was consistent with the proposed structure.

Step 4

The desired compound was prepared using the product described in Step 3 utilizing the sequence of Steps 4–8 described in Example 37. $^1$H-NMR was consistent with the proposed structure.

Step 5

A solution of the product from Step 4 (425 mg), 2-chloro-4,6-dimethoxytriazine (201 mg) and N-methylmorpholine (263 mg) in DMA (10 ml) was stirred in an ice bath under nitrogen. The reaction was allowed to warm to room temperature and stirring was continued for 3 hours. A solution of the product of Example G (386 mg) and N-methylmorpholine (105 mg) in DMA (5 ml) was prepared and added to the reaction at room temperature in one portion. The reaction was stirred for 15 hours, quenched with TFA (1.5 ml) and then concentrated under high vacuum. The residue was purified via reverse phase HPLC eluting with a water (0.5% TFA)-acetonitrile gradient to afford a white solid (706 mg). $^1$H-NMR was consistent with the proposed structure.

Step 6

The ester group from the product in Step 5 was hydrolyzed utilizing the same procedure described in Step 5 of Example 12. $^1$H-NMR was consistent with the proposed structure.

Analysis calculated for: $C_{21}H_{24}N_6O_6Cl_2$ 1.5TFA0.5H$_2$O C, 40.75; H, 3.78; N, 11.88; Cl, 10.02. Found: C, 40.40; H, 3.68; N, 12.10; Cl, 10.20.

EXAMPLE 39

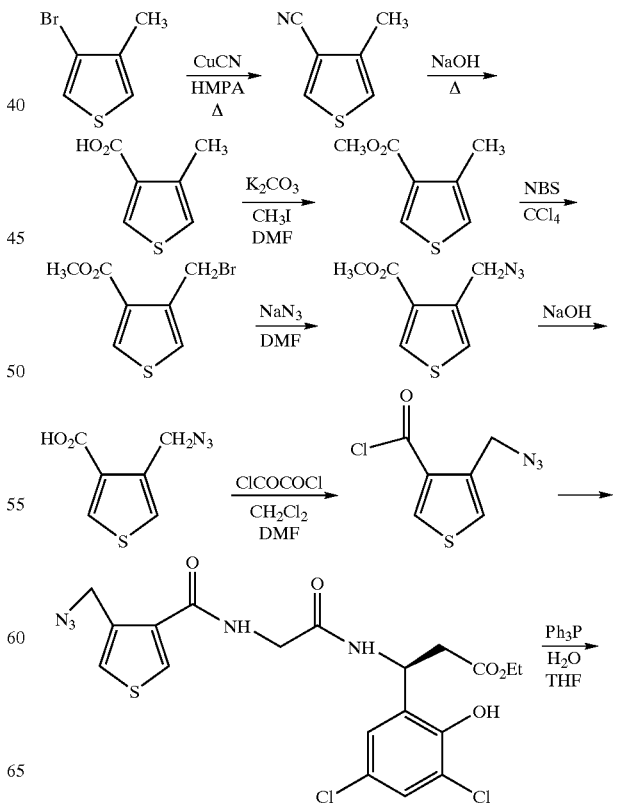

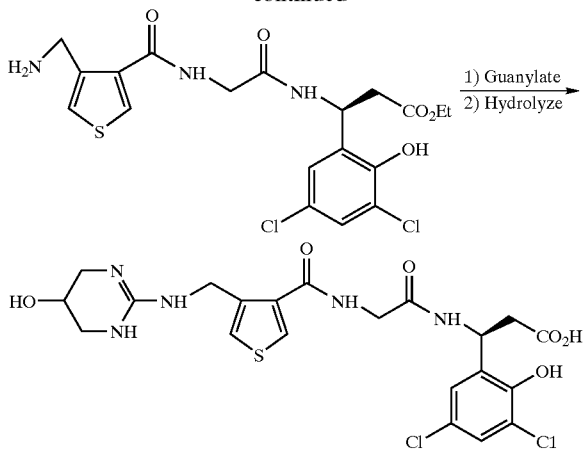

Step 1

A mixture of 3-bromo-4-methyl thiophene, (10 g) copper (1) cyanide (11.3 g) and HMPA (15 ml) was heated at 130–140° for 18 hours. The mixture was cooled and poured into a stirred solution of sodium cyanide (18.8 g) in water (28 ml) and stirred for 1 hour. The thick brown mixture was diluted with some additional water and extracted with ether. The combined ethereal extracts were washed with water, saturated sodium chloride solution, dried ($Na_2SO_4$) and concentrated. The residue was purified on a silica gel column eluting with 90% hexane-10% ethyl acetate to afford a pale yellow liquid (5.2 g). $^1$H-NMR was consistent with the proposed structure.

Step 2

A mixture of the nitrile prepared in Step 1 (1.5 g) and 2N sodium hydroxide solution (150 ml) was refluxed for 1 hour. The reaction was cooled and acidified with 2N hydrochloric acid until pH ~2 and extracted with ether. The combined ethereal extracts were dried ($Na_2SO_4$) and concentrated to afford a white solid (16.4 g) which was used without further purification. $^1$H-NMR was consistent with the proposed structure.

Step 3

The product from Step 2 (16.4 g) was esterified as described in Step 2 of Example 37 to afford the desired product (13.6 g) after purification on a silica gel column eluting with 10% ethyl acetate-90% hexane. $^1$H-NMR was consistent with the proposed structure.

Step 4

A mixture of N-bromosuccinimide (6.3 g) and dibenzoyl peroxide (100 mg) in carbon tetrachloride (25 ml) was added over a period of 90 minutes to a refluxing solution of the product from Step 3 (5.0 g) and dibenzoyl peroxide (100 mg) in $CCl_4$ (25 ml). After refluxing for 2 hours the reaction mixture was cooled, filtered and concentrated and the residue purified on a silica gel column eluting with 10% ethyl acetate-90% hexane to afford the desired compound (4.3 g). $^1$H-NMR was consistent with the proposed structure.

Step 5

A mixture of the product described in Step 4 (4.2 g), sodium azide (2.9 g) and DMF (50 ml) was heated at 55° under nitrogen for 5 hours. The reaction mixture was cooled and partitioned between water and ethyl acetate. The layers were separated and the aqueous portion was extracted with additional ethyl acetate. The combined organic extracts were washed with saturated sodium chloride solution, dried ($Na_2SO_4$) and concentrated to afford a golden oil (3.5 g) which was used without further purification. $^1$H-NMR was consistent with the proposed structure.

Step 6

A solution of the product described in Step 5 (1.0 g) 1N sodium hydroxide solution (15 ml) and methanol (15 mL) was stirred at room temperature for 16 hours. The reaction was treated with glacial acetic acid (2 ml) and concentrated. The residue was partitioned between water and ethyl acetate. The layers were separated and the aqueous portion was extracted with additional ethyl acetate. The combined organic extracts were washed with water, saturated sodium chloride solution, dried ($Na_2SO_4$) and concentrated. The residue was dried at 61° for 2 hours under high vacuum to afford a white solid (860 mg). $^1$H-NMR was consistent with the proposed structure.

Step 7

A solution of the product described in Step 6 (850 mg) in methylene chloride (10 ml) was chilled in an ice bath and treated with a 2N solution of oxalyl chloride (5 ml) in methylene chloride in one portion followed by 2 drops of DMF. The reaction was stirred for 2 hours while allowing to warm to room temperature. The solution was concentrated and dried under high vacuum at room temperature for 16 hours to afford a yellow brown solid (785 mg). $^1$H-NMR was consistent with the proposed structure.

Step 8

In a flame dried flask under nitrogen was placed a solution of diisopropylethylamine (1.3 ml), the product of Example G (1.4 g) and DMA (10 ml). The solution was chilled in an ice bath and a solution of the acid chloride from Step 7 (770 mg) in DMA (5 ml) was added dropwise. The reaction was stirred for 30 minutes after the addition was completed and then partitioned between ethyl acetate and water. The layers were separated and the aqueous portion was extracted with additional ethyl acetate. The combined organic extracts were purified on a silica gel column eluting with 50% ethyl acetate-50% hexane to afford white solid (1.0 g). $^1$H-NMR was consistent with the proposed structure.

Step 9

A solution of the product from Step 8 (806 mg) in ethanol (20 ml) was heated with a catalytic amount of 5% Pt/C under a 5 psi atmosphere of hydrogen at room temperature for 21 hours. The reaction was filtered and concentrated and the residue was purified via reverse phase HPLC eluting with a water (0.5% TFA)-acetonitrile gradient to afford a white solid (480 mg). $^1$H-NMR was consistent with the proposed structure.

Step 10

The product described in Step 9 (550 mg) was guanylated and purified using the conditions described in Step 4 of Example 21 to afford a white solid (206 mg). $^1$H-NMR was consistent with the proposed structure.

Step 11

The ester group from the product in Step 10 was hydrolyzed utilizing the same procedure set forth in Step 5 of Example 12. $^1$H-NMR was consistent with the proposed structure.

Analysis calculated for: $C_{21}H_{23}N_5O_5Cl_2S.1.5TFA$, $0.5H_2O$ C, 39.79; H, 3.55; N, 9.67; Cl, 9.79; S, 4.43. Found: C, 39.91; H, 3.58; N, 9.94; Cl, 10.06; S, 4.52.

EXAMPLE 40

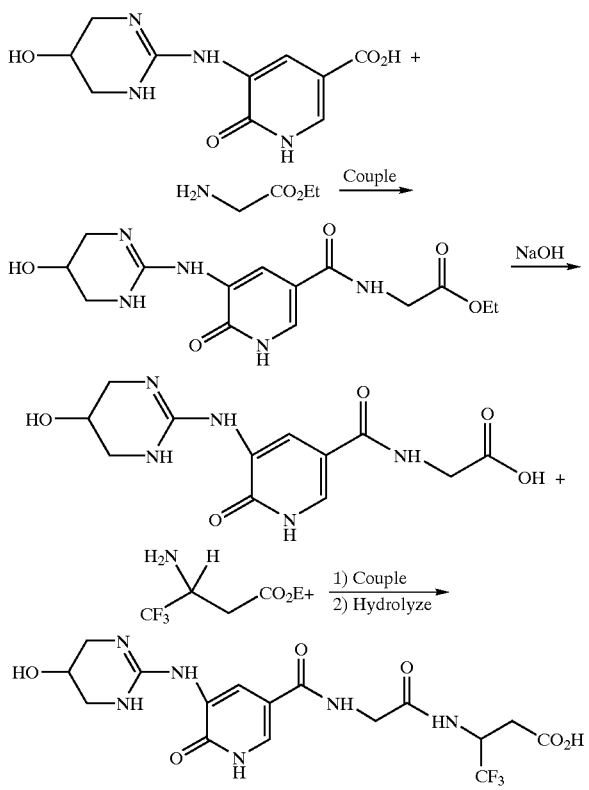

Step 1

The product prepared in Step 3 of Example 33 (1.0 g) was coupled with glycine ethyl ester hydrochloride utilizing the procedure described in Step 5 of Example 38 to afford a yellow solid (1.1 g) after a similar purification. $^1$H-NMR was consistent with the proposed structure.

Step 2

The produce described in Step 1 (1.0 g) was hydrolyzed using the procedure described in Step 5 of Example 21 to afford a white solid (910 mg). $^1$H-NMR was consistent with proposed structure.

Step 3

The product from Step 2 was coupled with 3-amino-4,4,4-trifluoro-butyric acid ethyl ester hydrochloride urilizing the protocol described in Step 5 of Example 38. $^1$H-NMR was consistent with the proposed structure.

Step 4

The ester group from the product in Step 3 was hydrolyzed utilizing the procedure described in Step 5 of Example 12. $^1$H-NMR was consistent with the proposed structure.

Analysis calculated for: $C_{17}H_{20}N_5O_6F_3$ 1.5TFA C, 38.01; H, 3.67; N, 11.08. Found C, 37.88; H, 3.64; N, 1102.

EXAMPLE 41

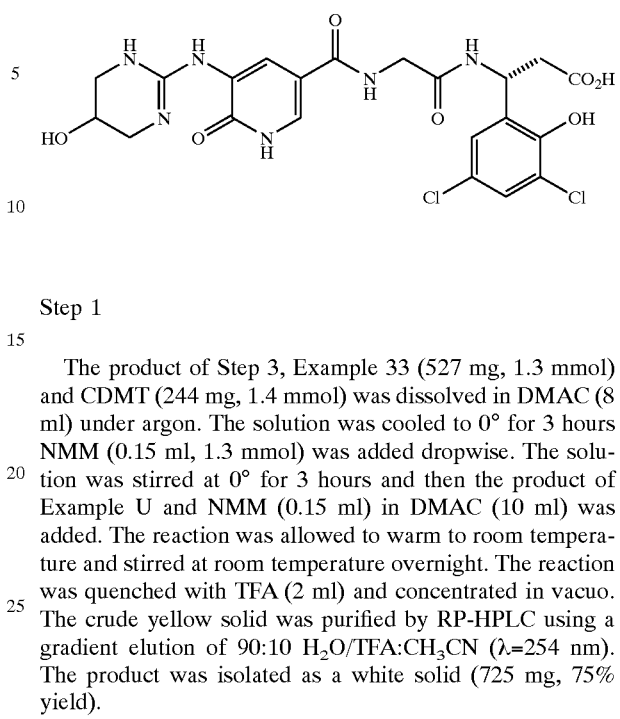

Step 1

The product of Step 3, Example 33 (527 mg, 1.3 mmol) and CDMT (244 mg, 1.4 mmol) was dissolved in DMAC (8 ml) under argon. The solution was cooled to 0° for 3 hours NMM (0.15 ml, 1.3 mmol) was added dropwise. The solution was stirred at 0° for 3 hours and then the product of Example U and NMM (0.15 ml) in DMAC (10 ml) was added. The reaction was allowed to warm to room temperature and stirred at room temperature overnight. The reaction was quenched with TFA (2 ml) and concentrated in vacuo. The crude yellow solid was purified by RP-HPLC using a gradient elution of 90:10 $H_2O$/TFA:$CH_3CN$ ($\lambda$=254 nm). The product was isolated as a white solid (725 mg, 75% yield).

Analysis Calculated for $C_{23}H_{26}N_6O_7Cl_2$ 1.5 TFA: C, 42.12; H, 3.74; N, 11.35. Found C, 42.26; H, 3.87; N, 11.45.

H.R.M.S. M+1 calculated for $C_{23}H_{27}N_6O_7Cl_2$ 569.1318. Found 569.1323.

Step 2

The product from Step 1 (725 mg, 0.98 mmol) was dissolved in THF(5 ml)/1$CH_3OH$) and 1M NaOH (6.5 ml) was added. The reaction was stirred at room temperature overnight and then 1M HCl (6.5 ml) was added. After concentrating in vacuo, the crude yellow solid was purified by RP-HPLC using a gradient elution of 95:5 $H_2O$/TFA:$CH_3CN$ ($\lambda$=254 nm). The product was isolated as a white solid (589 mg, 79% yield).

Analysis Calculated for: Anal. calcd for $C_{21}H_{22}N_6O_7Cl_2$ 1.9 TFA. C, 39.30; H, 3.18; N, 11.09. Found C, 39.22; H, 3.16; N, 11.39.

H.R.M.S. M+1 calculated for $C_{21}H_{23}N_6O_7Cl_2$ 541.1005. Found 541.1000.

EXAMPLE 42

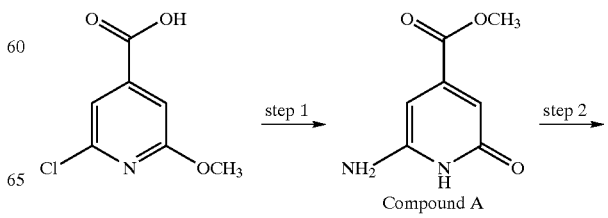

Compound A

113

-continued

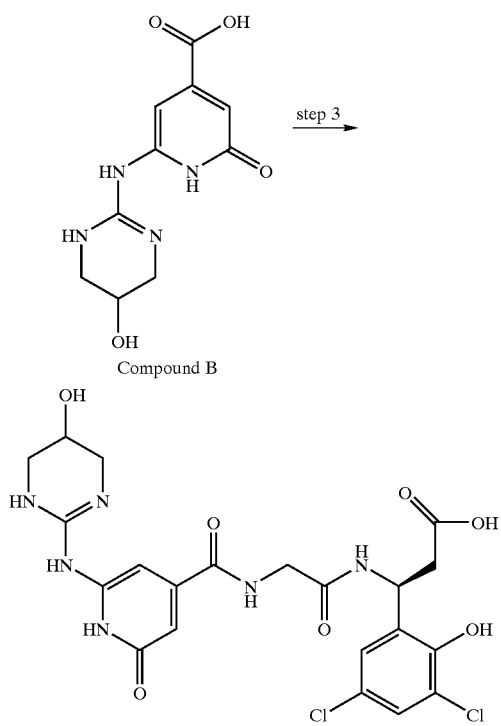

Compound B

Step 1

2-methoxy-6-chloropyridine carboxylic acid (10 g; 0.053 mol) was dissolved in an excess of concentrated aqueous ammonium hydroxide in a high pressure reactor and heated to 175° C. for 24 hours to obtain a pressure of 500 psi. The solution was evaporated to dryness under reduced pressure and converted to the acid by treatment with 2N HCl at 25° C. for 2 days and then evaporated to dryness under high vacuum, while heating to 60° C. After 12 hours, the residual water was azeotropically removed with absolute ethanol and the resulting residue was treated with methanol and evaporated under reduced pressure three times. The resulting residue was dissolved in methanol (250 ml) and 4N HCl in dioxane (25 mol) was added to this solution and then refluxed for 2.5 days. The solvent was removed by evaporating under reduced pressure and the resulting crude residue was purified by reverse phase HPLC (gradient, 95/5 0.1% TFA in $H_2O/CH_3CN$-60/40 0.1% TFA in $H_2O/CH_3CN$). The desired product was dissolved in methanol and treated with solid sodium bicarbonate, filtered, and the solvent evaporated. The resulting solid was suspended in 50/50 ethylacetate/hexane and the solid was collected by filtration to obtain of the desired brown solid (1.7 g, 20% yield).

Step 2

The compound (300 mg; 1.8 mmol) from Step 1 was dissolved in DMF (7.1 ml) and the product of Step 1, Example 9 (927 mg; 2.1 mmol) was added followed by triethylamine (0.44 ml, 325 mg; 3.2 mmol) and mercuric chloride (326 mg; 1.2 mmol). The reaction mixture was stirred at 25° C. for 3.5 hours then heated to 60° C. for 16 hours. Ethyl acetate (7 ml) was added to the reaction after cooling to room temperature and the heterogeneous solution was filtered through celite. The celite was washed thoroughly with 97/3 ethylacetate/ethanol. The solvents were removed under reduced pressure and the resulting crude red oil was dissolved in methylene chloride (30 ml) and treated with trifluoroacetic acid (2.77 ml) and refluxed for 1 hour.

114

The reaction was cooled and the solvent was removed under reduced pressure to give a brown oil. The sample was purified by reverse phase HPLC (C18, gradient 90/10 0.1% $TFA/H_2O$) to give an impure compound which was dissolved in methanol (2 ml) and treated with 1N NaOH (0.15 ml) and stripped to dryness to give a dark brown oil. This oil was purified by reverse phase HPLC (C18, gradient 99/1 0.1% $TFA/H_2O/CH_3CN$) to give a tan solid (36 mg).

Step 3

The compound (74 mg; 0.18 mmol) from the previous step was dried in the vacuum oven overnight and dissolved in DMF (1 ml) (stored over molecular sieves) and cooled to 0° C. Then N-methylpiperidine (27 ml; 22 mg; 0.22 mmol) was added followed by isobutylchloroformate (47 ml; 49 mg; 0.36 mmol) and stirred for 5 minutes. A solution (0.2 mL) of the product of Example G in DMF was added and the residual β-aminoester was washed with additional DMF (0.2 ml). Next N-methylpiperidine (22 ml; 18 mg; 0.18 mmol) was added. The reaction mixture was allowed to slowly warm to room temperature. After stirring at 25° C. for 12 hours the solvent was removed under high vacuum to give a red-brown oil which was purified by reverse phase HPLC (C18, gradient 80/20 0.1% $TFA/H_2O/CH_3CN$) to give the coupled product (22 mg) and the coupled product with an isobutylformyl group incorporated on the pyridone oxygen atom (47 mg). These products were combined and dissolved in methanol (2 ml) to which 1N aqueous sodium hydroxide (240 ml) was added. The reaction was stirred at 25° C. overnight and trifluoroacetic acid (84.7 ml) was added. The solvent was removed under reduced pressure and purified by reverse phase HPLC (C18, gradient 95/5 0.1% $TFA/H_2O/CH_3CN$) to give the desired product (37 mg).

Microanalytical calcd.for $C_{21}H_{22}N_6O_7Cl_2$. 2.1TFA. 0.2 $H_2O$ C, 38.58; H, 3.15; N, 10.71. Found 38.12; H, 3.36; N, 10.71.

EXAMPLE 43

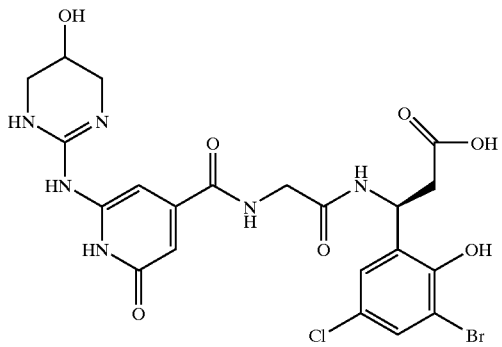

The above compound was prepared following the procedure described in Step 3, Example 42 by reacting the product of Step 2, Example 42 with the product of Example R.

Microanalytical calculated for: $C_{21}$ $H_{22}N_6O_7ClBr$. 1.8TFA: C, 37.35; H, 3.03; N, 10.62. Found C, 37.31; H, 3.23; N, 10.65.

EXAMPLE 44

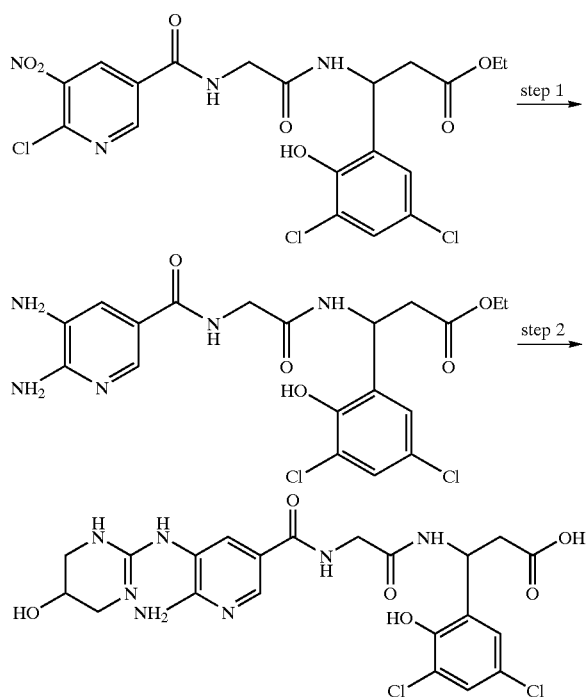

Step 1

The product of Step 3, Example 17 (3.0 g; 5.77 mmol) was dissolved in isopropanol (25 ml) and to this solution was added concentrated ammonium hydroxide (45 ml). After stirring at 25° C. for 3 hours, the solution was evaporated to dryness under reduced pressure. The crude sample was hydrogenated in a Parr shaker in ethanol (3A) (50 ml) over 5% platinum on carbon at 5 psi at 25° C. for 2.5 hours. The sample was filtered and the filtrates were concentrated to dryness under reduced pressure. The compound was purified by reverse phase chromatography (C18, 80/20 $CH_3CN/H_2O$ gradient) to yield the desired product (1.5 g, 39% yield).

Step 2

The product of step 1 (200 mg) was dissolved in methanol (2 ml) and sodium bicarbonate (133 mg) was added. The solution was stirred for 30 minutes at 25° C., filtered and the resulting solution evaporated to dryness. The resulting sample (205 mg; 0.43 mmol) was dissolved in DMF (1.72 ml) and then the product of Step 1, Example 9 (282.8 mg; 0.65) was added, followed by triethylamine (99 mg; 0.97 mmol, 0.14 ml) then mercuric chloride (177 mg; 0.65 mmol). The solution was heated to 60° C. for 30 minutes then to 90° C. for 12 hours. The reaction mixture was cooled then diluted with ethyl acetate (1.7 ml) and filtered through celite. The resulting filtrate was evaporated to dryness. The crude sample was purified by flash chromatography to remove unreacted starting material. This material was treated with 50/50 $TFA/CH_2Cl_2$ to give the impure desired product. This material was dissolved in methanol (2 ml) and 1N sodium hydroxide (2 ml). After stirring at 25° C. for 12 hours, the solution was neutralized with TFA (77 ml), then evaporated to dryness under reduced pressure. The crude product was purified by reverse phase chromatography (C18, 95/5 $H_2O/CH_3CN$) to give the desired product (6.8 mg).

Microanalytical calcd.for $C_{21}H_{23}N_7O_6Cl_2$. 3.3TFA: C, 36.17; H, 2.89; N, 10.70. Found C, 36.57; H, 3.21; N, 10.37.

EXAMPLE 45

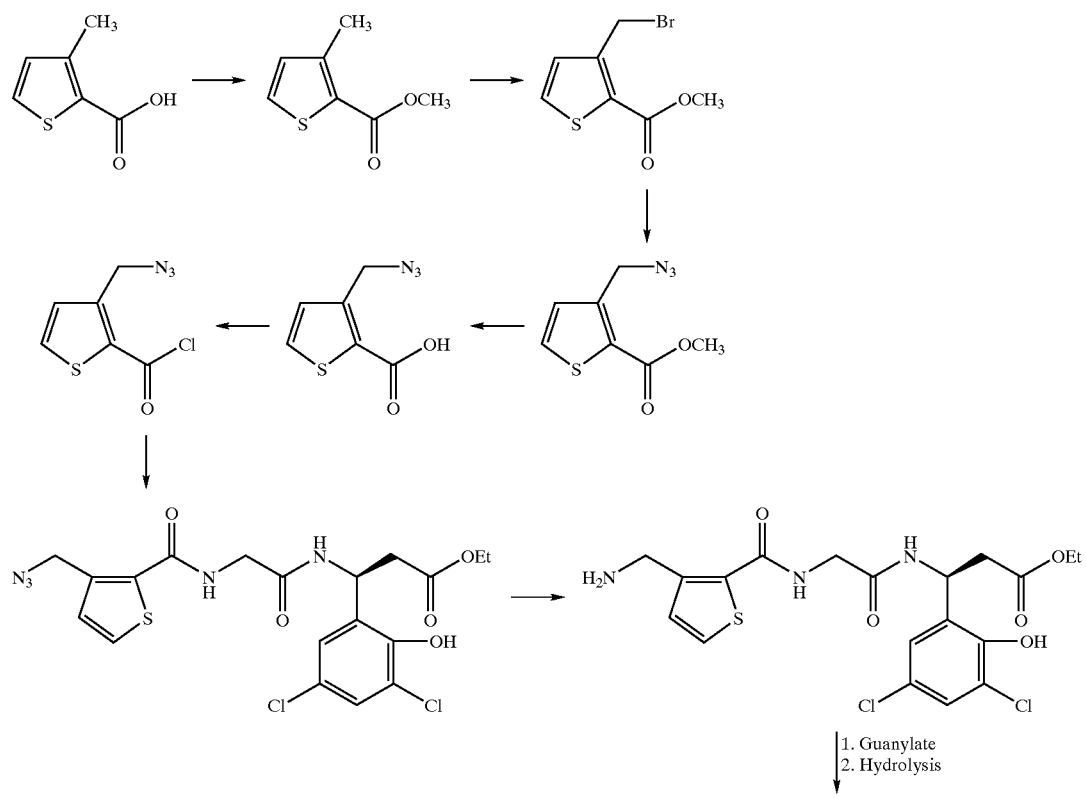

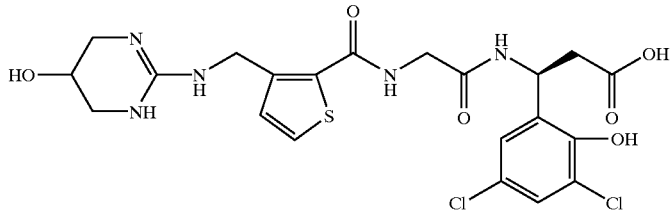

Step 1

To a mixture of 3-methyl-2-thiophenecarboxylic acid (1.0 g, 7.0 mmol), N,N-dimethylformamide (4.0 ml), and potassium carbonate (1.93 g, 14 mmol), was added iodomethane (1.49 g, 10.5 mmol). The reaction was stirred at room temperature for 80 hours, and diluted with ethyl acetate (150 ml), and washed with $H_2O$ (100 ml), and brine (100 ml). The organic layer was dried ($Mg_2SO_4$) and concentrated to a clean product as a pale brown oil (0.87 g, 81% yield). $^1H$ NMR was consistent with the proposed structure.

Step 2

To a solution of the product of Step 1 (5.0 g, 32.0 mmol), dibenzoyl peroxide (0.08 g), and carbon tetrachloride (20 ml), was added a mixture of N-bromosuccinimide (6.3 g, 35.3 mmol), dibenzoyl peroxide (0.08 g), and carbon tetrachloride (20 ml) at reflux over 30 minutes. The resulting reaction mixture was heated at reflux for 18 hours. The solid was filtered and washed with carbon tetrachloride (2×10 ml). The filtrate was concentrated to give a mixture of oil and solid (8.1 g, 80% yield). $^1H$ NMR was consistent with the proposed structure.

Step 3

A mixture of the product of Step 2 (8.1 g, 34.7 mmol), sodium azide (5.6 g, 87 mmol), and N,N-dimethylformamide (25 ml) was heated at 58° C. for 2.5 hours. The reaction was diluted with ethyl acetate (800 ml), and washed with $H_2O$ (500 ml). The aqueous layer was extracted with ethyl acetate (100 ml). The combined organic layer was dried ($MgSO_4$) and concentrated to give a pale brown oil (6.0 g, 85% yield). $^1H$ NMR was consistent with the proposed structure.

Step 4

A solution of the product of Step 3 (6.0 g, 25.9 mmol), NaOH (1N, 50 ml), and MeOH (50 ml) was stirred overnight. The reaction was treated with acetic acid (2.5 ml). The product was extracted with ethyl acetate (300 ml). The organic layer was dried with $Na_2SO_4$, and concentrated to give a yellow oil. A yellow solid (2.0 g, 42% yield) was obtained under vacuum. $^1H$ NMR was consistent with the proposed structure.

Step 5

A mixture of the product of Step 4 (0.5 g, 2.7 mmol), oxalyl chloride (2 M in dichloromethane, 2.7 ml, 5.4 mmol), and dichloromethane (20 ml) was stirred at room temperature for 2.5 hours. The solvent was removed from the reaction to give the product as brown oil (0.51 g, 85% yield). $^1H$ NMR was consistent with the proposed structure.

Step 6

A solution of the product of Example G (0.91 g, 2.43 mmol), diisopropylethylamine (0.63 g, 4.86 mmol), and N,N-dimethylacetamide (20 ml) was added to a mixture of the product of Step 5 (0.46 g, 2.43 mmol) and THF (10 ml) at 0° C. The reaction mixture was stirred at 0° C. for 10 minutes and allowed to warm to room temperature. After 16 hours, the solvents were removed from the reaction under vacuum. The product was extracted with ethyl acetate (300 ml). The organic solution was washed with saturated $NaHCO_3$ solution (100 ml), $H_2O$ (100 ml), dried with $Na_2S_2O_4$, and concentrated to give the crude product. The crude product was purified by column chromatography (on silica gel, $CH_2Cl_2$/MeOH/$NH_4OH$, 98/2/0.2) to give clean product as a gummy solid (0.7 g, 58% yield). $^1H$ NMR was consistent with the proposed structure.

Step 7

At room temperature, a mixture of the product of Step 6 (0.78 g, 1.56 mmol), 5% Pt/C, and EtOH was stirred under 5 psi for 20 hours. The catalyst was filtered. The filtrate was treated with trifloroacetic acid (0.6 ml) and concentrated to give the crude product. The crude product was purified by HPLC to give a white solid (0.4 g, 54% yield). $^1H$ NMR was consistent with the proposed structure.

Step 8

Mercury (II) chloride (0.51 g, 1.87 mmol) was added to a mixture of the product of Step 7 (0.55 g, 1.25 mmol), product of Step 1, Example 9 (0.81 g, 1.87 mmol), triethylamine (0.38 g, 3,75 mmol), and N,N-dimethylforamide (15 ml) at room temperature. The reaction was heated at 95–100° C. for 16 hours. The cooled reaction was filtered through a bed of celite (2"), and washed with ethyl acetate. The solvent was removed from the filtrate under vacuum to give a oil. This oil was diluted with $CH_2Cl_2$/trifloroacetic acid (10 ml/10 ml) and stirred at room temperature for 1 hour. The solid formed was collected by filtration. The filtrate was concentrated and treated with $CH_2Cl_2$/trifloroacetic acid (15 ml/15 ml) for 1.5 hours. The solvent was removed under reduced pressure to give a brown oil. This oil was purified by HPLC to give a mixture of the desired product and its ethyl ester. The desired compound was recrystallized from acetonitrile as a white solid (0.068 g). The ester product was treated with NaOH/Ethanol (7.0 ml/7.0 ml) for 18 hours, and purified by HPLC to give additional (0.055 g) compound.

Calculated for $C_{21}H_{23}N_5O_6Cl_2S \cdot 2.0\ CF_3COOH$: C, 38.87; H, 3.26; N, 9.07. Found: C, 38.78; H, 3.6; N, 9.16.

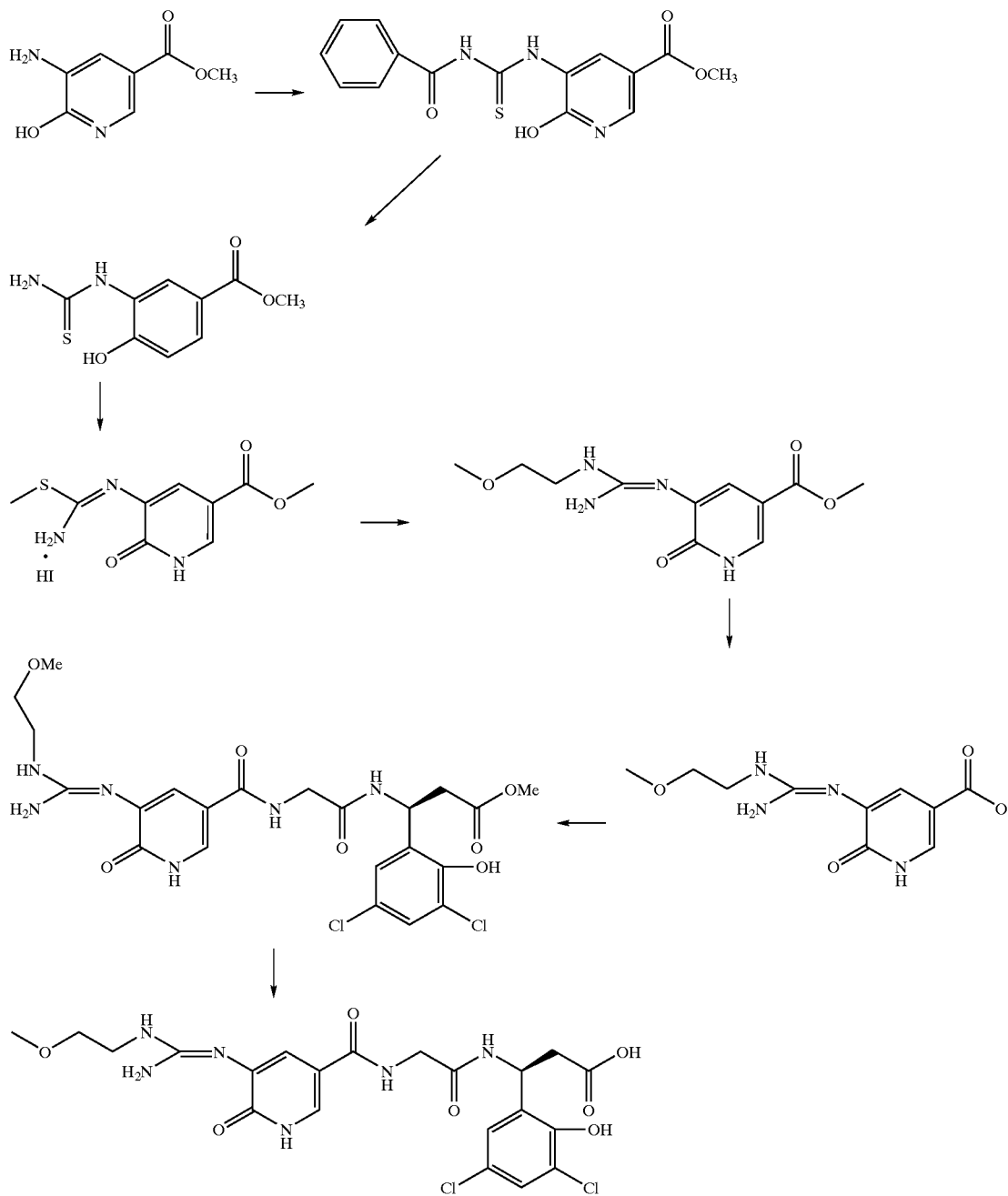

Step 1

Benzoylisothiocyanate (3.34 g, 21.3 mmol) was added to a solution of the product of Step 1, Example 33 (3.5 g, 20.8 mmol) and N,N-dimethylformamide (45 ml) at room temperature. The reaction was stirred for 2 hours, and poured into ether (300 ml). The resulting mixture was stirred for 15 minutes. The product was collected by filtration, washed with ether (2×40 ml), and air-dried as a yellow solid (6.95 g, 100% yield). $^1$H NMR was consistent with the proposed structure.

Step 2

Sodium methoxide (2.64 g, 48.9 mmol) was added to a suspension of the product of step 1 (6.90 g, 20.8 mmol) and methanol (200 ml) in small portions at room temperature. Upon completion of the addition, the reaction was stirred for 1 hour. Acetic acid (2.8 ml, 48.9 mmol) was added to the reaction. The resulting mixture was stirred for 15 minutes. The product was collected by filtration, washed with methanol (2×30 ml), and dried under reduced pressure to yield an off white solid (3.8 g, 81% yield). $^1$H NMR was consistent with the proposed structure.

Step 3

A mixture of the product of Step 2 (1.90 g, 8.4 mmol), methyl iodide (3.56, 25.1 mmol) and methanol (60 ml) was heated at reflux for 3.5 hours, and cooled to room temperature. The solvent was removed from the reaction solution under reduced pressure to give a yellow oil. The oil residue was treated with ether to give a clean product as a yellow solid (3.1 g, 100% yield). $^1$H NMR was consistent with the proposed structure.

Step 4

A solution of the product of Step 3 (0.5 g, 1.36 mmol), 2-methoxyethylamine (0.12 ml, 1.36 mmol) and N,N-dimethylacetamide (5.0 ml) was heated at 85° C. for 2.5 hours. An additional 2-methoxyethylamine (0.12 ml, 1.36 mmol) was added. The reaction was heated at 85° C. for 2 hours. N,N-dimethylacetamide was removed from the cooled reaction under reduced pressure to give a crude product. The crude product was purified by reverse phase HPLC to yield the desired clean product (0.38 g, 76% yield). $^1$H NMR spectra was consistent for the proposed structure.

Step 5

A solution of the product of Step 1 (0.38 g, 1.42 mmol), NaOH solution (1N, 15 ml), and MeOH (15 ml) was stirred at room temperature for 16 hours, and then treated with trifluoroacetic acid (1.2 ml). The solvent was removed from the reaction solution under reduced pressure to give a crude product. The crude product was purified by HPLC to yield the desired product as a white solid (0.55 g, 100% yield). $^1$H NMR was consistent with the proposed structure.

Step 6

N-methylmorpholine (0.1 ml, 1.42 mmol) was added to a solution of the product of Step 5 (0.54 g 1.42 mmol) in N,N-dimethylacetamide (16 ml). At −5° C., isobutyl chloroformate (0.18 g, 1.35 mmol) was added to the reaction over 5 minutes, and stirred for 15 minutes. A solution of the product of Example G (0.396 g, 1.07 mmol) and N-methyl morpholine (0.075 ml, 1.07 mmol) and N,N-dimethylacetamide (10 ml) was added to the reaction. The resulting reaction solution was allowed to warm to room temperature and stirred for 16 hours. The solvent was removed from the reaction solution under reduced pressure to give a crude product. The crude product was purified by HPLC to yield the desired product as a white solid (0.145 g, 14% yield). $^1$H NMR was consistent with the proposed structure.

Step 7

A solution of the product of Step 6 (0.145 g, 0.20 mmol), NaOH (1N, 25 ml), and MeOH (25 ml) was stirred for 16 hours. The solvent was removed from the reaction mixture under reduced pressure to give a crude product. The crude product was treated with trifloroacetic acid (2 ml) and purified by HPLC to give the desired product as a off white solid (0.11 g, (70% yield).

Calculated for $C_{21}H_{24}N_6O_7Cl_2 \cdot 2CF_3COOH$: C, 38.93; H, 3.40; N, 10.89. Found: C, 39.29; H, 3.47; N, 11.15.

EXAMPLE 47

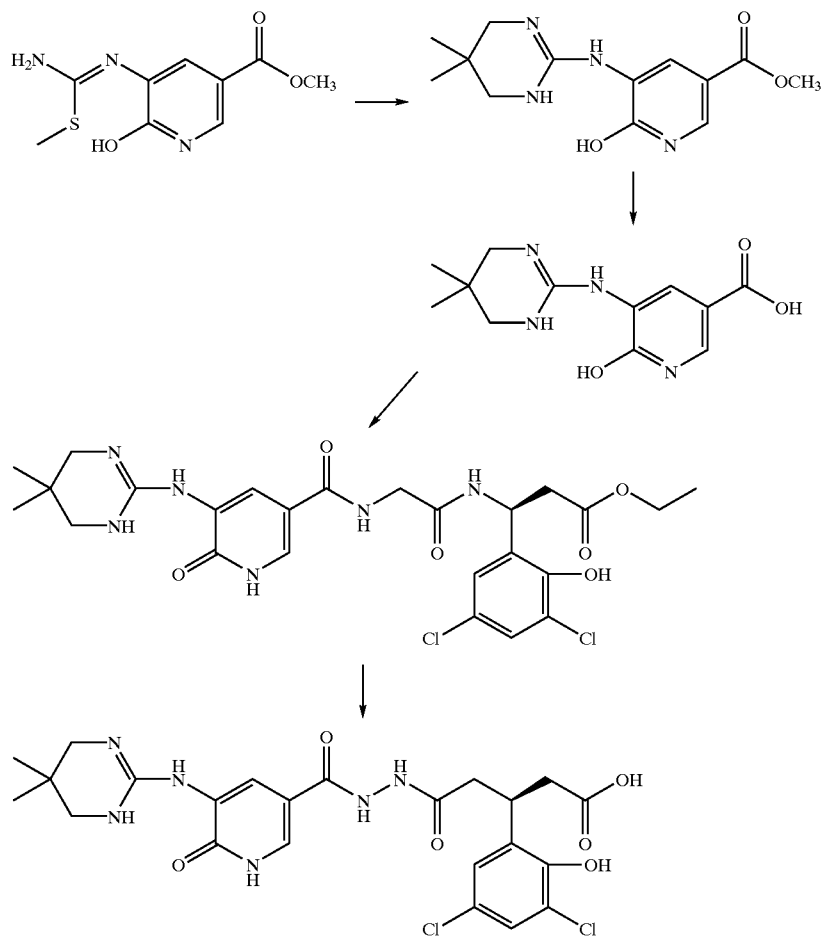

Step 1

A mixture of the product of Step 3, Example 46 (1.56 g, 4.22 mmol), 2,2-dimethyl-1,3-propanediamine (0.45 g, 4.40 mmol), and N,N-dimethylacetamide (15 ml) was heated at 92° C.–95° C. for 6.5 hours and then allowed to cool to room temperature. A solid was formed overnight. The product was collected by filtration, and washed with N,N-dimethylacetamide (5 ml), and ether (5 ml) to give a clean product as a white solid (0.50 g, 43% yield). ¹H NMR was consistent with the proposed structure.

Step 2

A solution of the product of Step 1 (0.48 g, 1.7 mmol), NaOH (1N, 10 ml), and MeOH (10 ml) was stirred at room temperature overnight. The solvent was removed from the reaction mixture under reduced pressure to give a crude product. The crude product was treated with triflouroacetic acid (2 ml) and purified by HPLC to give a white solid as the desired product (0.38 g, 58% yield).

Step 3

A solution of 4-methyl morpholine (0.14 g, 1.41 mmol) in N,N-dimethylacetamide (1.5 ml) was added to a solution of the product of Step 2 (0.36 g, 0.94 mmol), 2-chloro4,6-dimethoxytriazine (0.18 g, 1.03 mmol) and N,N-dimethylacetamide (10 ml) at 0° C. The resulting bright orange solution was allowed to warm to room temperature, and stirred for 3 hours. A solution of the product of Example G (0.350 g, 0.94 mmol), 4-methyl morpholine (0.93 g, 0.94 mmol), and N,N-dimethylacetamide (4 ml) was added to the reaction solution. The resulting solution was stirred at room temperature overnight, and treated with trifloroacetic acid (1.0 ml). The solvent was removed from the reaction solution under reduced pressure to give a crude product. The crude product was purified by HPLC to give a yellow solid as the desired product (0.35 g, 54% yield).

Step 4

A solution of the product of Step 3 (0.33 g, 0.47 mmol), NaOH (1N, 9 ml), and MeOH (9 ml) was stirred 18 hours. The reaction was treated with trifloroacetic acid (1.0 ml). The solvent was removed from the reaction solution under reduced pressure to give a crude product. The crude product was purified by HPLC to give the desired compound as a pale yellow solid (0.285 g, 84% yield).

Calculated for $C_{23}H_{26}N_6O_6Cl_2 \cdot 1.25CF_3COOH \cdot 1.0H_2O$: C, 42.90; H, 4.13; N, 11.77. Found: C, 43.03; H, 4.03; N, 11.26.

EXAMPLE 48

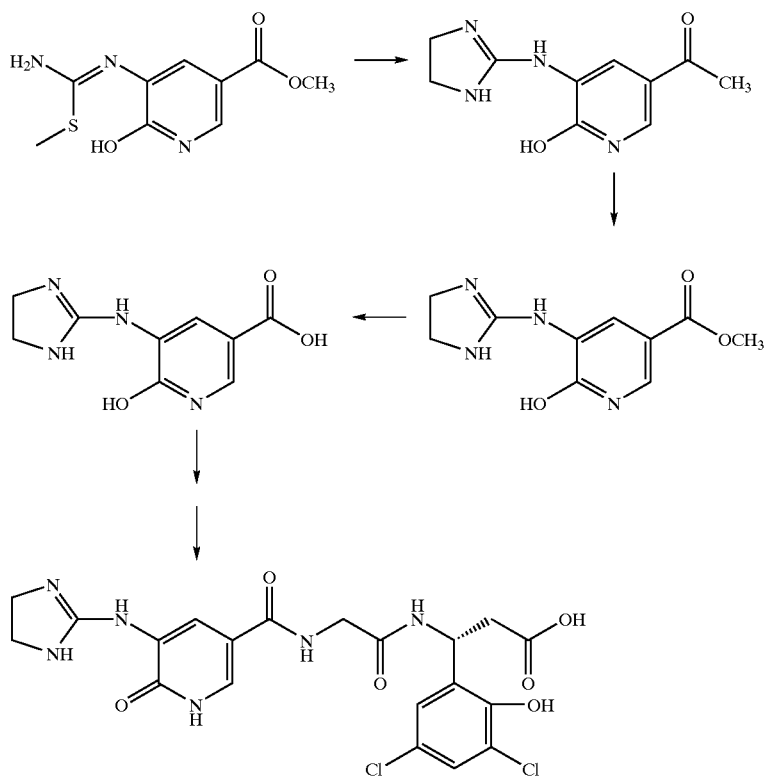

The above compound was synthesized using the methodology described in Example 47. In Step 1 ethylenediamine was used instead of 2,2-dimethyl-1,3-diaminopropanediamine. In Step 3 the product of Example U was used instead of the product of Example G.

Calculated for $C_{20}H_{20}N_6O_6Cl_2 \cdot 1.25CF_3COOH \cdot 0.5H_2O$: C, 40.77; H, 3.38; N, 12.68. Found: C, 40.98; H, 3.17; N, 12.57.

EXAMPLE X

Preparation of 5-Bromo-3-iodosalicylaldehyde

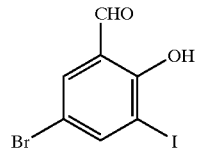

The above compound was prepared by iodination of 5-bromosalicylaldehyde as described in literature (J. Org. Chem. 1990, 55, 5287–5291).

EXAMPLES Y & Z

Scheme A1

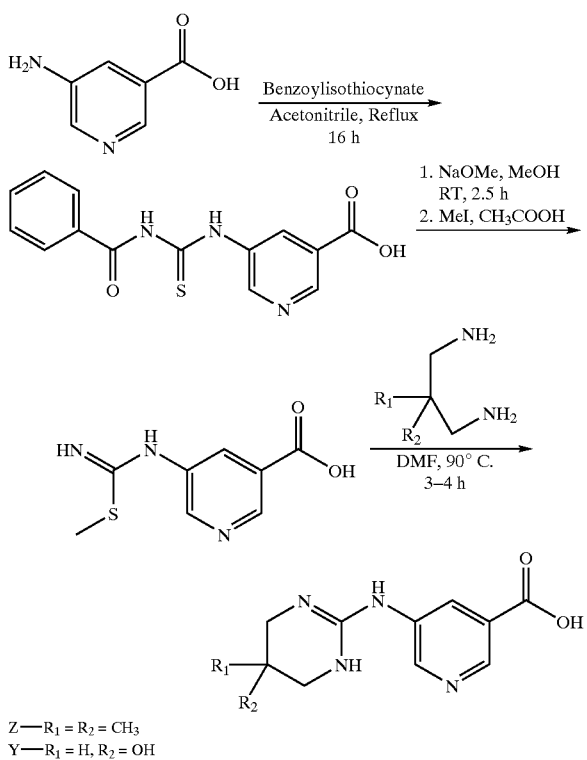

Z—$R_1 = R_2 = CH_3$
Y—$R_1 = H, R_2 = OH$

Step 1
Preparation of

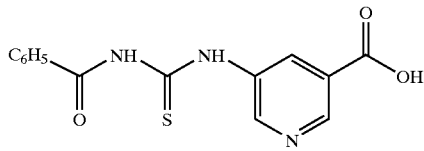

A mixture of 5-aminonicotinc acid (10.0 g, 0.072 mole), benzoylisothiocyanate (11.8 g, 0.072 mole), and DMAP (catalytic amount) in anhydrous acetonitrile (250 mL) was heated to reflux overnight under anhydrous conditions with vigorous stirring (Scheme A1). The resulting yellow suspension was cooled and filtered. The residue was washed with water, followed by acetonitrile, and dried in vacuo overnight to yield the desired product as a pale yellow solid (21.4 g, 98% yield).

MS and $^1$H-NMR were consistent with the desired structure.

Step 2
Preparation of

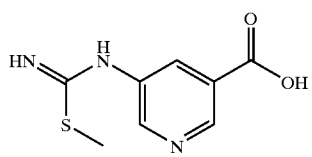

To the suspension of the product from Step 1 (11.1 g, 0.037 mole) in anhydrous MeOH (230 mL), was added NaOMe (25 wt % solution in methanol, 21.1 mL, 0.092 mole), at which point the reactant went into solution to give an orange-brown solution (Scheme A1). This solution was stirred at room temperature for 3 hours, cooled in an ice bath, and methyliodide (3.45 mL, 0.055 mole added). The resulting mixture was stirred at 10° C. for 30 minutes and 1.5 hours at room temperature. The reaction mixture was then quenched with acetic acid (2 mL), cooled in an ice bath, and filtered. The solids were washed with cold MeOH and dried in vacuo to afford the desired product as a beige solid (2.66 g, 37% yield).

MS and $^1$H-NMR were consistent with the desired structure.

Step 3
Preparation of Examples Y & Z.

To a solution of 1,3-diamino-2-hydroxypropane (11.2 g, 0.124 mole) in anhydrous DMF (80 mL), was added the product from Step 2 (8.7 g, 0.041 mole). This mixture was heated at 85° C. under anhydrous conditions for 3 hours (Scheme A1). After 1–2 hours of heating, the solution became turbid and turbidity increased during the course of heating. The reaction mixture was then cooled in an ice bath and filtered. The solids were washed with acetonitrile, water, acetonitrile, and dried in vacuo to yield the desired product (Example Y) as a beige solid (3.7 g, 38% yield ).

MS and $^1$H-NMR were consistent with the desired structure.

Example Z was synthesized using the methodology described for Example Y substituting 4 equivalents of 2,2-dimethyl-1,3-propanediamine for 1,3-diamino,2-hydroxypropane.

Each of the products from Step 3 were converted to their respective TFA or HCl salts by stirring 1 hour at 10° C. in a solution of anhydrous THF (10 mL for 1.0 g substrate) and TFA (1 eqivalent) or 4N HCl/dioxane (2 eqivalents).

EXAMPLE 49

Preparation of

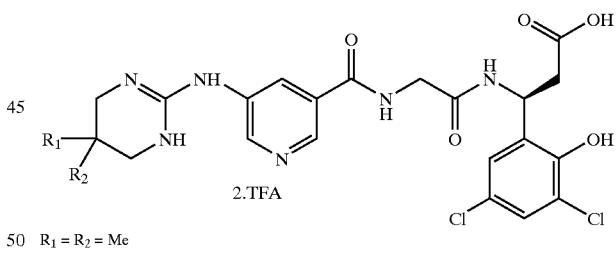

$R_1 = R_2 = Me$

Scheme A2

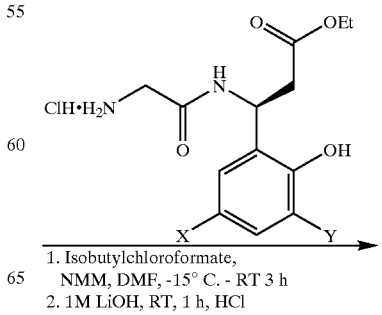

1. Isobutylchloroformate, NMM, DMF, -15° C. - RT 3 h
2. 1M LiOH, RT, 1 h, HCl

127

-continued

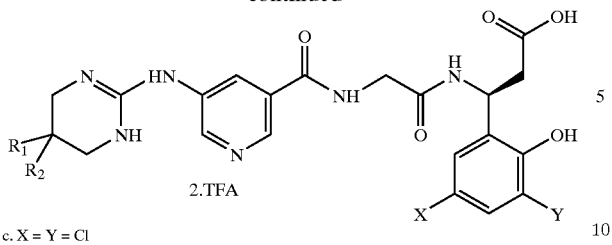

c. X = Y = Cl
   $R_1 = R_2 = CH_3$
d. X = Cl, Y = Br
   $R_1 = R_2 = CH_3$

To a suspension of Example Y (0.40 g, 0.00125 mole, Scheme A2) in anhydrous DMF (10 mL) at −20° C. was added isobutylchloroformate (0.17 g, 0.00125 mole), followed by the dropwise addition of N-methylmorpholine (0.14 g, 0.00137 mole). After stirring this mixture under argon atmosphere for 20 minutes at −20° C., an additional amount of N-methylmorpholine (0.14 g, 0.00137 mole) was added, followed by the addition of product from Example G (0.46 g, 0.00125 mole). The resulting mixture was stirred at −20° C. for 15 minutes, and then stirred at room temperature for 2 hours. DMF was distilled in vacuo and the residue was purified by reverse phase HPLC to yield (after lyophilization) the desired ester as a white solid (0.20 g, 21% yield).

MS and $^1$H-NMR were consistent with the desired structure. This ester (0.2 g) was stirred with 1M LiOH (2 mL) for 1 hour at room temperature. The pH was adjusted to 2 with trifluoroacetic acid and the product was purified by reverse phase HPLC to provide (after lyophilization) the desired acid as a white solid (0.11 g).

MS and $^1$H-NMR were consistent with the desired structure.

EXAMPLE 50

Preparation of

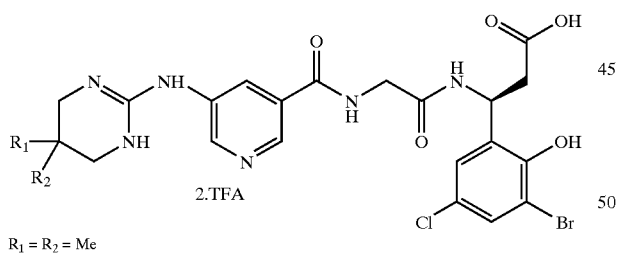

$R_1 = R_2 = Me$

The above compound was prepared (Scheme A2) using the procedure described in Example 49 substituting an equivalent amount of Example R for the Example G.

MS and $^1$H-NMR were consistent with the desired structure(s). The ester (0.19 g, 0.00023 mole) was stirred with 1M LiOH (2 mL) for 1 hour at room temperature. The pH was adjusted to 2 with trifluoroacetic acid and the product was purified by reverse phase HPLC to provide (after lyophilization) the desired acid as a white solid (0.13 g, 72% yield).

MS and $^1$H-NMR were consistent with the desired structure.

128

EXAMPLE 51

Preparation of

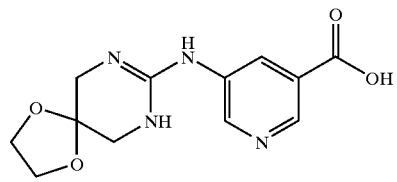

Scheme B

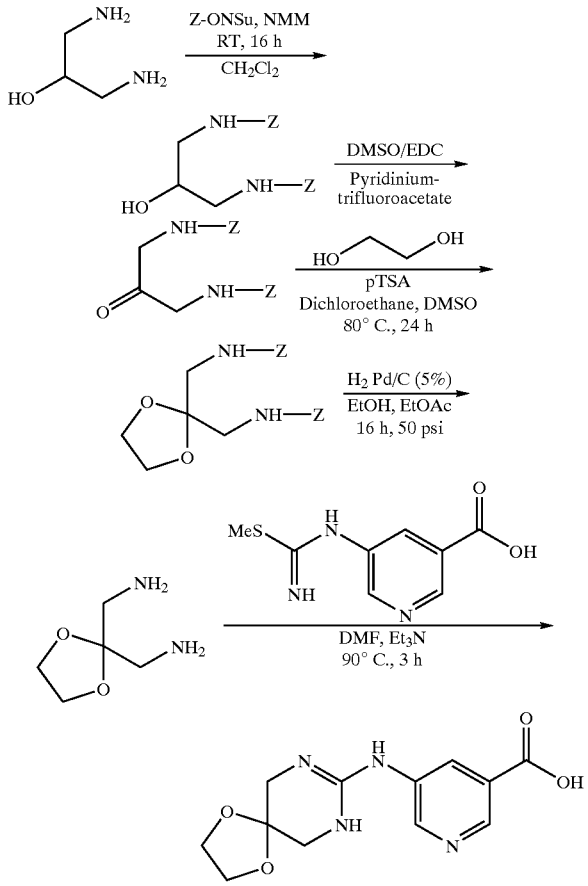

Step 1
Preparation of bis-N-benzyloxycarbonyl-2-hydoxy-1,3-diaminopropane.

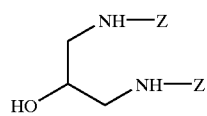

To a suspension of 2-hydroxy-1,3 diaminopropane (5.8 g, 0.064 mol) in dichloromethane (150 mL) containing N-methylmorpholine (14 mL) at 10° C., was added benzyloxycarbonylsuccinimide (32 g, 0.129 mol) in portions (Scheme B). The reaction mixture was stirred at room temperature for 16 hours, and resulting clear solution was diluted with dichloromethane (100 mL), washed successively with 10% citric acid (2×50 mL), water and dried (Na$_2$SO$_4$). Following filtration, the solvent was removed under reduced pressure, and resulting white solid was crystallized from dichloromethane to afford desired compound (20.0 g, 87%). ¹H-NMR and MS were consistent with the structure.

Step 2

Preparation of bis-N-benzyloxycarbonyl-1,3-diaminopropane-2-one.

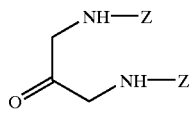

To a suspension of product from Step 1 (21.0 g, 0.058 mol) and EDC (33.0 g) in dichloromethane (120 mL) containing DMSO (24.0 mL), was added dropwise a solution of pyridiniumtrifluoroacetate (33.0 g) in dichloromethane (50 mL) over a period of 30 minutes and stirred at 10° C.

After the addition, a clear yellow solution was obtained. Upon stirring at room temperature for 3 hours, a white solid separated from the reaction mixture. It was cooled, filtered, and the solid was washed with cold dichloromethane and water. The white solid obtained was dried in a desiccator in vacuo to afford the desired product (15.5 g, 74% yield). ¹H-NMR and MS were consistent with the structure.

Step 3

Preparation of

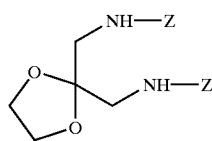

A mixture of product from Step 2 (2.5 g, 0.007 mol), p-toluenesulfonic acid (0.3 g, 0.0016 mol), and DMSO (1.0 mL) in dichloroethane (25 mL) containing ethyleneglycol (2.0 mL) was heated to reflux under anhydrous conditions (Scheme B). After 24 hours, the reaction mixture was cooled, diluted with dichloromethane (25 mL) and washed successively with 10% sodium bicarbonate, water and dried (Na₂SO₄). After removal of the solvent under reduced pressure, the residue was crystallized from dichloromethane/hexane to give the desired compound (2.5 g, 89% yield). ¹H-NMR and MS were consistent with the structure.

Step 4

The product from Step 3 (3.0 g, 0.0075 mol) was dissolved in a solvent mixture of ethanol (50.0 mL) and ethyl acetate (50.0 mL), and hydrogenated at 50 psi in the presence of Pd/C (5%, 1.5 g) for 16 hours at room temperature (Scheme B). The catalyst was removed by filtration, was washed with 40% water in ethanol (50 mL) and filtered. The combined filtrate and aqueous washings were concentrated to dryness under reduced pressure to afford a syrup. This material was dissolved in DMF (10.0 mL), the product from Step 2 of Example 1 (1.0 g, 0.0047 mol), was added with triethylamine (0.7 mL), and DMAP (0.05 g). The resulting mixture was heated at 90° C. under anhydrous conditions. After 3 hours, DMF was distilled in vacuo, the residue was triturated with water, and filtered. It was washed with water, acetonitrile, and dried in a desiccator in vacuo to obtain Example 5 (0.4 g, 30%) as a powder. This material was used without further purification in step B. ¹H-NMR and MS were consistent with the structure.

EXAMPLE 52

Preparation of

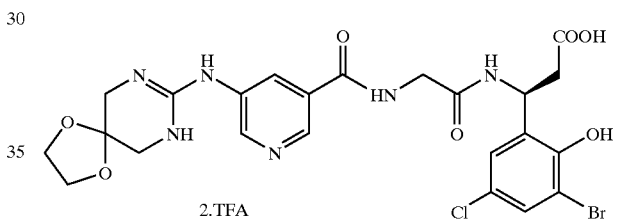

Scheme C

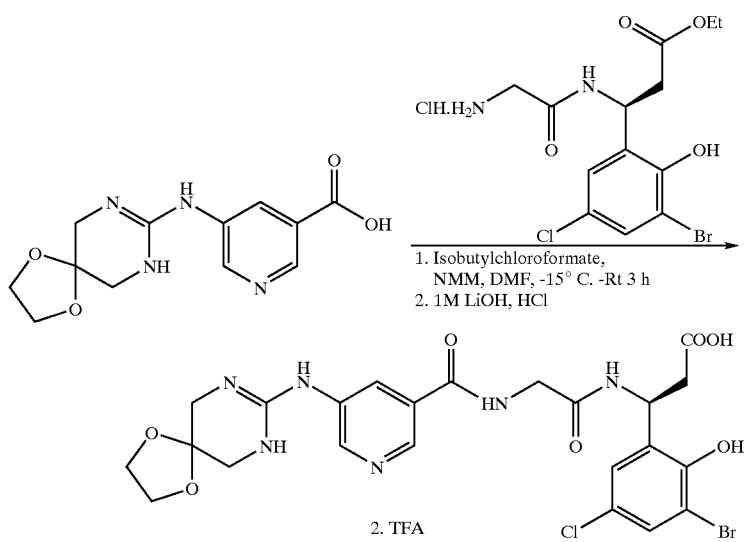

The compound of Example 51 (0.38 g, 0.0014 mol) was suspended in dry THF (5.0 mL) and trifluoroacetic acid (0.1 mL) was added and stirred at 10° C. under anhydrous conditions (Scheme C). After 30 minutes, the THF was distilled under reduced pressure and the residue was dried in vacuo for 3 hours. The resulting material was dissolved in dry DMF (4.0 mL), cooled to −15° C., and isobutylchloroformate (0.18 mL) was added, followed by the addition of N-methylmorpholine (0.17 mL). The solution was stirred for 30 minutes under an argon atmosphere. To the mixture was added a solution of amine generated by the addition of N-methylmorpholine (0.17 mL) to a solution of Example R (0.51 g) in DMF (3.0 mL) at 0° C. The resulting mixture was stirred at −15° C. for 30 minutes, and then at room temperature for 16 hours. The solvents were then removed by distillation in vacuo, and the residue was purified by reverse-phase HPLC using 10–90% acetonitrile/water gradient (40 minutes) at a flow rate of 70 mL/min.

The appropriate fractions were combined and freeze dried to afford the desired ester (0.4 g) as a fluffy white powder. This material was stirred with lithium hydroxide (1M, 2.0 mL) at room temperature. After 45 minutes, the reaction mixture was cooled, diluted with water, acidified with trifluoroacetic acid, and the desired acid (0.25 g,) was isolated by reverse-phase HPLC using 10–90% acetonitrile/water as described above. $^1$H-NMR and MS were consistent with the structure.

EXAMPLE 53

Preparation of

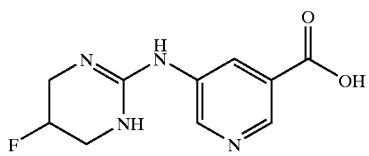

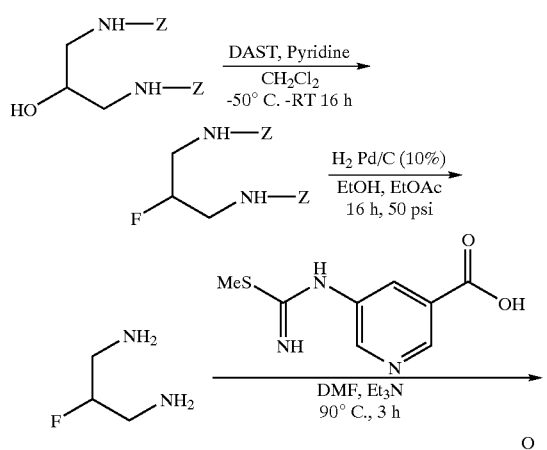

Z = Carbobenzoxy

Step 1

Preparation of bis-N-benzyloxycarbonyl-2-fluoro-1,3-diaminopropane.

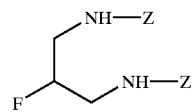

To a stirred suspension of bis-N-benzyloxycarbonyl-2-hydoxy-1,3-diaminopropane (6.0 g, 0.017 mol) in dichloromethane (50 mL) and pyridine (2.7 mL) at −50° C., was added dropwise a solution of DAST (2.5 mL) in dichloromethane (7.5 mL, Scheme D). The reaction mixture was gradually allowed to warm to room temperature over a period of 16 hours under an atmosphere of argon. A clear yellow solution was obtained. The solution was cooled and poured into a mixture of ice, water (100 mL), and dichloromethane (50 mL). The organic phase was washed with water (2×50 mL), and dried (Na$_2$SO$_4$). After removal of the solvent, the residue was purified by silica gel flash chromatography using 30% EtOAc in hexane. The appropriate fractions were combined, concentrated to dryness and the product was crystallized from dichloromethane/hexane to afford the desired fluoro intermediate as a white fluffy powder (2.0 g). $^1$H-NMR and MS were consistent with the structure.

Step 2

A solution of bis-N-benzyloxycarbonyl-2-fluoro-1,3-diaminopropane (3.3 g, 0.0092 mol) obtained from Step 1, in EtOAc (30 mL), and EtOH (30 mL) was hydrogenated at 50 psi in the presence of Pd/C (10%, 2.7 g) for 16 hours at room temperature (Scheme D). Following filtration, the catalyst was stirred with EtOH containing 40% water (50 mL) and filtered again. The filtrate was concentrated to dryness to afford a syrup (0.7 g). The syrup was suspended in DMF (8.0 mL). The product from Step 2 of Example 1 (0.7 g, 0.0033 mol), catalytic amount of DMAP (0.01 g), were added and heated at 90° C. for 3 hours under anhydrous conditions. DMF was distilled in vacuo, the residue was suspended in water (25 mL) and the pH was adjusted to 4.5 by the addition of 1N HCl. The resulting mixture was cooled. The solid that separated was filtered and washed thoroughly with water, acetonitrile and dried in a desiccator in vacuo to provide the desired compound as brown powder (0.24 g). $^1$H-NMR and MS were consistent with the structure.

EXAMPLE 54

Preparation of

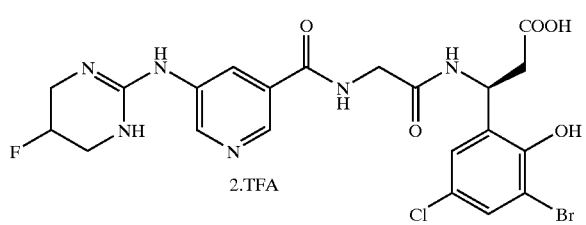

Scheme E

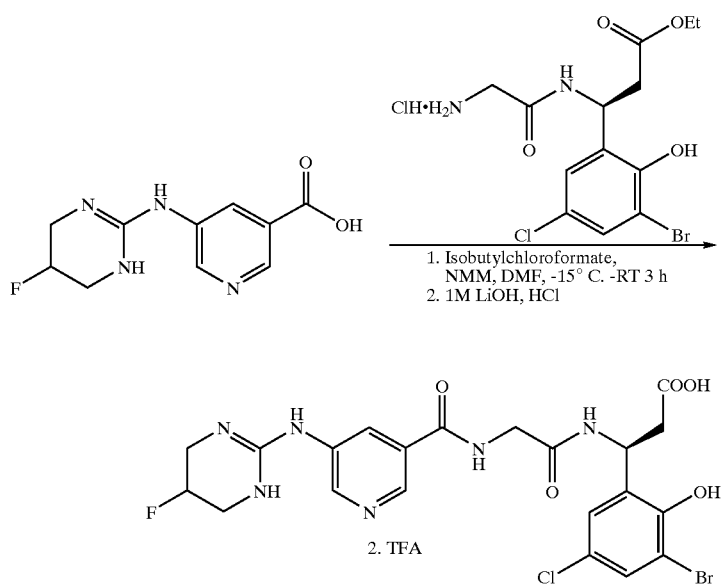

The compound of Example 53 (0.22 g) as obtained above was suspended in dry THF (4.0 mL). Trifluoroacetic acid (0.1 mL), was added and the solution was stirred at 10° C. for 30 minutes, and concentrated under reduced pressure. The residue was dried in a desiccator in vacuo. The material obtained was suspended in dry DMF (5 mL). Isobutylchloroformate (0.12 mL) was added, followed by the addition of N-methylmorpholine (0.11 mL). The solution was stirred −15° C. under an argon atmosphere (Scheme E). After 30 minutes, a solution of amine generated by the addition of N-methylmorpholine (0.095 mL) to a solution of the product of Example R (0.37 g) in DMF (3.0 mL) was added. The resulting mixture was stirred at −15° C. for 30 minutes, and at room temperature for 16 hours. DMF was distilled in vacuo and the residue was purified by reverse-phase HPLC using 10–90% acetonitrile/water. The appropriate fractions were combined and freeze dried to afford the desired ester product as a pale yellow powder (0.35 g). $^1$H-NMR and MS were consistent with the structure.

The resulting product (0.3 g, Scheme E) was stirred with 1M LiOH (3.0 mL) at room temperature. After 1 hour, the solution was diluted with water (3.0 mL), cooled and acidified with trifluoroacetic acid. The resulting mixture was then purified by reverse-phase HPLC using 10–90% acetonitrile/water (30 minute gradient) at flow rate of 70 mL/min. The appropriate fractions were combined and freeze dried to provide the desired compound as a white powder (0.22 g). $^1$H-NMR and MS were consistent with the structure.

EXAMPLE 55

Preparation of

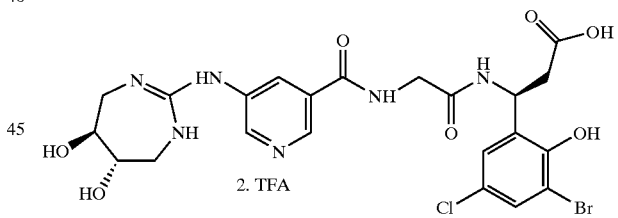

Scheme F

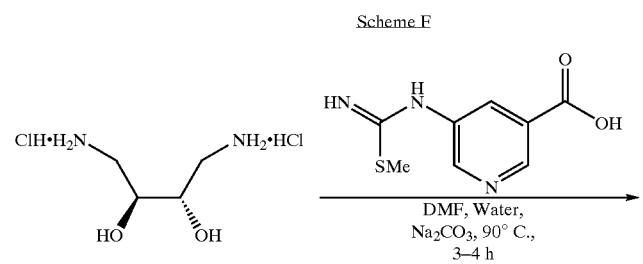

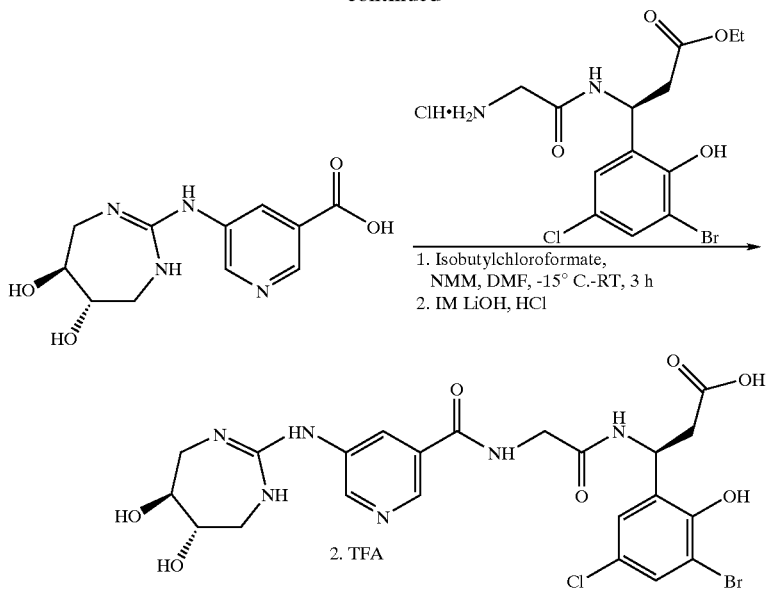

Step 1
Preparation of

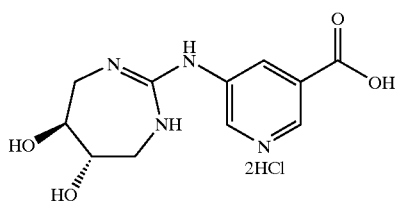

To a solution of 1,4-diamino-2,3-dihydroxybutane dihydrochloride [2.21 g, 0.012 mole] [synthesized from dimethyl-L-tartrate as described in J. Carbohydrate Chemistry, 5, (2), 183–197, [1986], in water (6 mL) and anhydrous DMF (10 mL), was added sodium carbonate (1.83 g, 0.017 mole). To this mixture, the product from Step 2 of Example 1 (1.21 g, 0.006 mole) was added and the mixture was heated at 85° C. for 3 hours. After cooling in an ice bath, DMF was distilled in vacuo and, the resulting residue was suspended in water. The pH was adjusted to 5.6. The solution was lyophilized to afford the desired product (0.907 g, 59% yield).

MS was consistent with the desired structure (M+H 267). The compound obtained was converted to its HCl salt by stirring with 4N HCl/dioxane (2 equivalents) in THF (10 mL) at 10° C. for 1 hour.

Step 2

To a suspension of the product from Step 1 (0.11 g, 0.00023 mole) in anhydrous DMF (10 mL) at −20° C., was added isobutylchloroformate (0.016 g, 0.00012 mole), followed by the dropwise addition of N-methylmorpholine (0.013 g, 0.00013 mole, Scheme F). After stirring this mixture under argon atmosphere for 20 minutes at −20° C., an additional amount of N-methylmorpholine (0.013 g, 0.00013 mole) was added followed by the addition of the product from Example R (0.048 g, 0.00012 mole). The resulting mixture was stirred at −20° C. for 15 minutes. After stirring at room temperature for 2 hours, DMF was distilled in vacuo and the residue was purified by reverse-phase HPLC to yield (after lyophilization) the desired ester as a white solid (0.03 g, 33 % yield).

MS (M+H 627 M+H 629) and $^1$H-NMR were consistent with the desired structure.

$^1$H-NMR (400 MHz, Cd$_3$Od): δ 8.8 (s, 1H) δ 8.5 (s, 1H), 8.1 (s, 1H), 7.4 (s, 1H), 7.2 (s, 1H) 5.6 (m, 1H), 4.1 (m, 4H), 3.7 (m, 2H), 3.6 (m, 2H), 3.3 (m, 2H), 2.9 (m, 2H), 1.2 (m, 3H)

The resulting ester (0.03 g, 0.000035 mole) was stirred with 1M LiOH (2 mL). After stirring for 1 hour at room temperature, the pH was adjusted to 2 with trifluoroacetic acid, and the product was isolated by reverse-phase HPLC to provide (after lyophilization) the desired acid as a white solid (0.001 g, 3.5 % yield).

MS (M+H 599 M+H 601) and $^1$H-NMR were consistent with the desired structure.

$^1$H-NMR (400 MHz, CD$_3$OD): δ 8.8 (s, 1H), 8.5 (s, 1H), 8.0 (s, 1H), 7.4 (s, 1H), 7.2 (s, 1H) 5.6 (m, 1H), 4.1 (m, 2H), 3.8 (m, 2H), 3.5 (m, 2H), 3.3 (m, 2H), 2.8 (m, 2H)

EXAMPLE 56

The difluoro analog is prepared according to the synthetic sequence outlined in Scheme 1 below.

Scheme 1

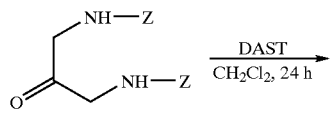

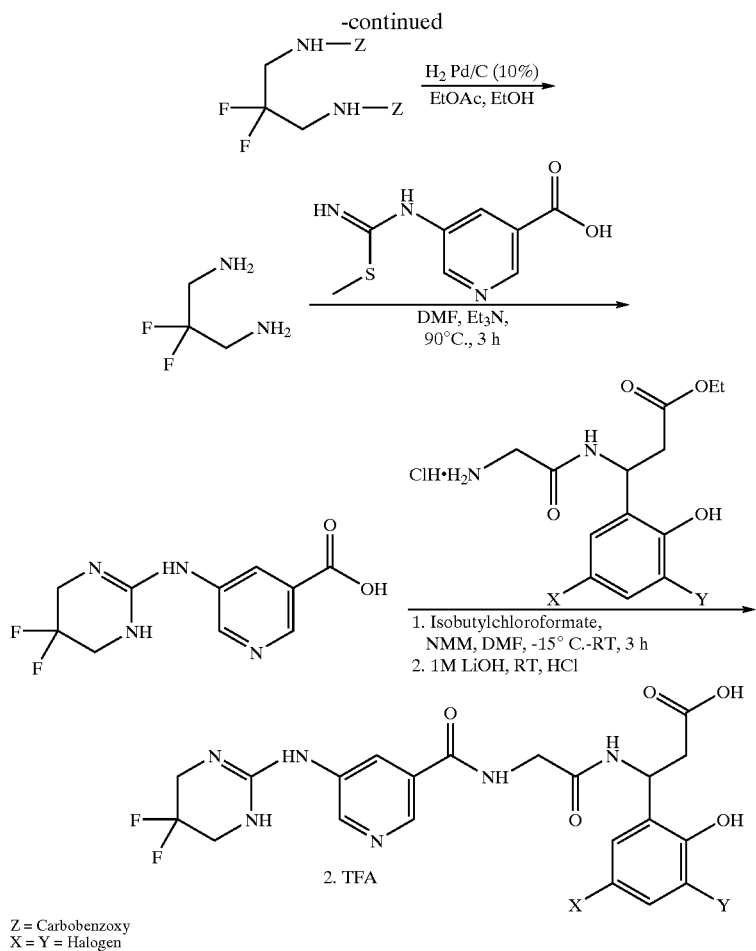

Z = Carbobenzoxy
X = Y = Halogen

The carbobenzoxy-protected ketone is converted to the corresponding difluoro intermediate using DAST diethylaminosulfur trifluoride. Subsequent removal of the carbobenzoxy groups (Z) by catalytic hydrogenation and coupling of the resulting diamine with the S-methylisothiourea derivative of 5-aminonicotinic acid derivative, provides the corresponding difluoro-substituted guanidine containing nicotinic acid precursor. This compound is reacted with a glycine-beta amino acid-ester, followed by hydrolysis and acidification to yield the final desired compound.

Example 57

Compounds containing seven-membered fluoro/hydroxy substituted guanidines are prepared according to the following Scheme starting from the known diisopropyl-L-tartrate (*J. Am. Chem. Soc.* 1988, 110, 7538).

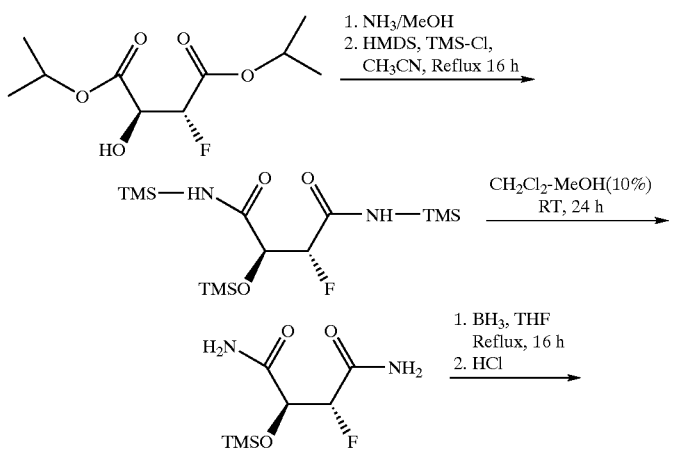

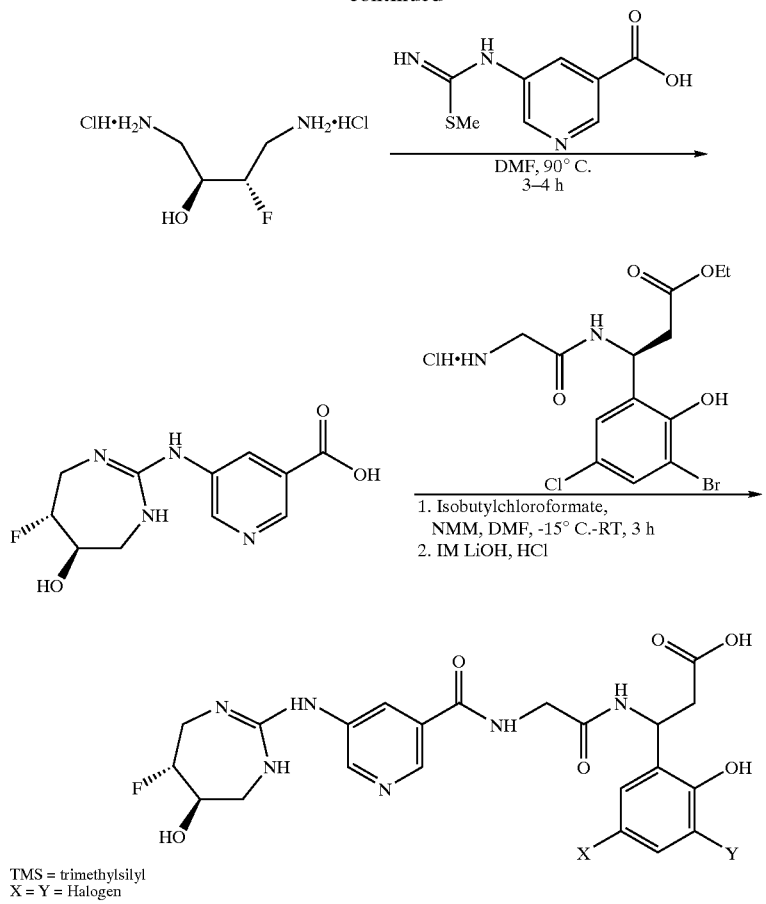

TMS = trimethylsilyl
X = Y = Halogen

The monosilylated intermediate is synthesized by amidation, silylation and N-desilylation. The diborane reduction of this monosilyl derivative provides the corresponding diamine dihydrochloride. Subsequent condensation of the free-diamine with the S-methylisothiourea 5-aminonicotinic acid derivative, provides the corresponding seven-membered guanidine derivative. Further reaction of this guaniidine with the glycine-beta-amino acid-ester, followed by hydrolysis and acidification yields the final desired compound.

EXAMPLE 58

The dialkyl/diol substituted seven-membered cyclic guanidine compounds are prepared according to reactions outlined in the following Scheme. Starting from the known carbobenzoxy-protected diamines (*J. Med. Chem.* 1996, 39, 2156), the corresponding seven-membered cyclic guanidine is synthesized by reacting the free-diamine precursor with the S-methylisothiourea 5-aminonicotinic acid derivative. The condensation of the resulting guanidine-carboxylic acid with a glycine-beta-amino acid-ester, followed by hydrolysis and acidification yields the final desired compound.

Scheme 3

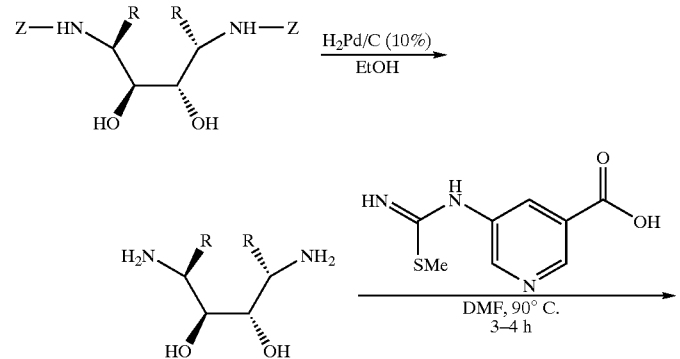

-continued

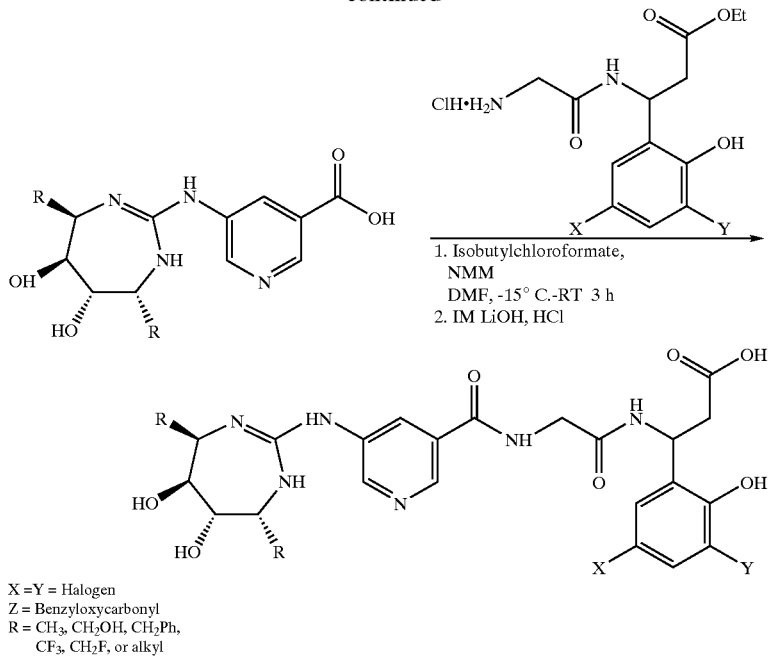

X = Y = Halogen
Z = Benzyloxycarbonyl
R = CH₃, CH₂OH, CH₂Ph, CF₃, CH₂F, or alkyl

EXAMPLE 59

The dihydroxy compounds are prepared by the acid catalysed cleavage of the cyclic ketal precursor as shown in the following Scheme.

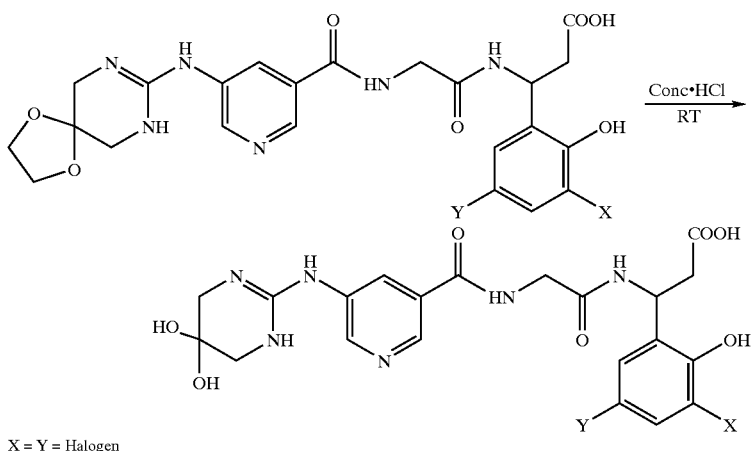

X = Y = Halogen

EXAMPLE 60

Compounds containing the seven-membered diol substituted cyclic guanidines starting from D or meso-tartarate derivatives are prepared as outlined in Scheme F.

The activity of the compounds of the present invention was tested in the following assays. The results of testing in the assays are tabulated in Table 1.

Vitronectin Adhesion Assay

Materials

Human vitronectin receptor ($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., *Blood*, 70:475–483 (1987)]. The purified human vitronectin receptor ($\alpha_v\beta_3$) was diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 µL/well (100 ng receptor/well). The plates were sealed and incubated overnight at 4° C. to allow the receptor to bind to the wells. All remaining steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0\times10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 µL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1 ] which is a potent $\alpha_v\beta_3$ antagonist ($IC_{50}$ in the range 3–10 nM) was included on each plate as a positive control.

Purified IIb/IIIa Receptor Assay

Materials

Human fibrinogen receptor ($\alpha_v\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Vs.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_v\beta_3$) was diluted from stock solutions to 1.0 µg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 µL/well (100 ng receptor/well). The plates were sealed and incubated overnight at 4° C. to allow the receptor to bind to the wells. All remaining Steps were at room temperature. The assay plates were emptied and 200 µL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 µL aliquots to the assay plate was carried out with a CETUS Propette robot; the final concentration of the labeled ligand was 1 nM and the highest concentration of test compound was $1.0\times10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 µL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm, [Robard et al., *Int. Atomic Energy Agency. Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155, Example 1] which is a potent $\alpha_v\beta_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise, the $IC_{50}$ is reported as being greater than the highest concentration tested.

| EXAMPLE NO. | $\alpha_v\beta_3$ ($IC_{50}$, nm) | IIb/IIIa ($IC_{50}$, nm) |
|---|---|---|
| 1 | 1.58 | 313 |
| 2 | 1.32 | 272 |
| 3 | 0.41 | 298 |
| 4 | 0.74 | 581 |
| 5 | 0.42 | 884 |
| 6 | 0.27 | 1260 |
| 7 | 0.21 | 361 |
| 8 | 95.1 | 857 |
| 9 | 0.18 | 244 |
| 10 | 0.14 | 161 |
| 11 | 0.34 | 462 |
| 12 | 4.5 | 442 |
| 13 | 9.32 | 780 |
| 14 | 12.4 | 772 |
| 15 | 25.4 | 1040 |
| 16 | 22000 | 6180 |
| 17 | 0.46 | 724 |
| 18 | 0.43 | 798 |
| 19 | 2.96 | 2490 |
| 20 | 0.32 | 2020 |
| 21 | 0.2 | 551 |
| 22 | 6.96 | 1710 |
| 23 | 3600 | 10100 |
| 24 | 91200 | 15800 |
| 25 | 1870 | 3910 |
| 26 | 0.71 | 831 |
| 27 | 0.26 | 482 |
| 28 | 0.43 | 984 |
| 29 | 0.46 | 1385 |
| 30 | 155 | 29.5 |
| 31 | 3942 | 1803 |
| 32 | 2.1 | 49 |
| 33 | 0.2 | 520 |
| 34 | 0.34 | 1203 |
| 35 | 0.14 | 340 |
| 36 | 1.13 | 970 |
| 37 | 63.8 | 267 |
| 38 | 278 | 115 |
| 39 | 1917 | 2458 |

-continued

| EXAMPLE NO. | $\alpha_v\beta_3$ ($IC_{50}$, nm) | IIb/IIIa ($IC_{50}$, nm) |
|---|---|---|
| 40 | 1.5 | 20630 |
| 41 | 10.2 | 35400 |
| 42 | 3.1 | 5954 |
| 43 | 6.5 | 7527 |
| 44 | 42.1 | 1061 |
| 45 | 1094 | 1678 |
| 46 | 1.97 | 2693 |
| 47 | 0.99 | 6709 |
| 48 | 4.3 | 27910 |

What is claimed is:
1.

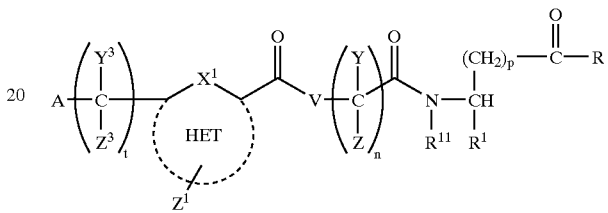

or a pharmaceutically acceptable salt thereof, wherein

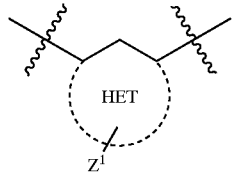

is a 5–8 membered monocyclic heterocyclic ring, optionally unsaturated, containing 1 to 4 heteroatoms, selected from the group consisting of O, N and S, wherein $X^1$ is selected from the group consisting of CH, $CH_2$, N, NH, O and S;

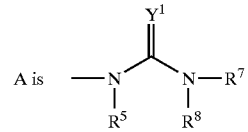

wherein
  $Y^1$ is selected from the group consisting of N—$R^2$, O, and S;
  $R^2$ is selected from the group consisting of H; alkyl; aryl; hydroxy; alkoxy; cyano; nitro; amino; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl; alkyl optionally substituted with one or more substitutent selected from the group consisting of lower alkyl, halogen, hydroxyl, haloalkyl, cyano, nitro, carboxyl, amino, alkoxy, aryl and aryl optionally substituted with one or more substituent selected from the group consisting of halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, and fused monocyclic heterocycles; aryl optionally substituted with one or more substituent selected from the group consisting of halogen, haloalkyl, hydroxy, lower alkyl, alkoxy, methylenedioxy, ethylenedioxy, cyano, nitro, alkylthio, alkylsulfonyl, sulfonic acid, sulfonamide, a radical of the formula

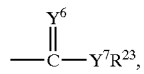

amino, aryl, fused aryl, monocyclic heterocycles and fused monocyclic heterocycle; monocyclic heterocycles; and moncyclic heterocycles optionally substituted with one or more substitutent selected from the group consisting of halogen, haloalkyl, lower alkyl, alkoxy, amino, nitro, hydroxy, a radical of the formula

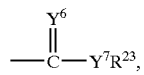

cyano, alkylthio, alkylsulfonyl, sulfonic acid, sulfonamide, aryl and fused aryl; or $R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl, carboxyl ester, spirodioxolane, and fused phenyl; or $R^2$ taken together with $R^7$ forms a 4–12 membered heterocycle, optionally unsaturated, containing one or more heteroatom selected from the group consisting of O, N and S; or $R^2$ taken together with $R^7$ forms a 5–9 membered heteroaromatic ring optionally substituted with one or more substituent selected from the group consisting of lower alkyl, phenyl, alkoxy and hydroxy; or $R^2$ taken together with $R^7$ forms a 5 membered heteroaromatic ring fused with a aryl or heteroaryl ring;

wherein $Y^6$ and $Y^7$ are independently selected from the group consisting of O, N, and S; and $R^{23}$ is selected from the group consisting of H, alkyl, aralkyl or aryl, $R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido; alkylcarbonyl; arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; alkyl optionally substituted with one or more substiuent selected from the group consisting of lower alkyl, halogen, hydroxy, haloalkyl, cyano, nitro, a radical of the formula

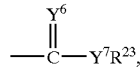

amino, alkoxy, thio, alkylthio, sulfonyl, aryl, aralkyl, aryl optionally substituted with one or more substituent selected from the group consisting of halogen, haloalkyl, lower alkyl, alkoxy, methylenedioxy, ethylenedioxy, alkylthio, haloalkylthio, thio, hydroxy, cyano, nitro, a radical of the formula

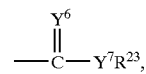

aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, moncyclic heterocycles, and fused moncyclic heterocycles; aryl optionally substituted with one or more substituent selected halogen, haloalkyl, lower alkyl, alkoxy, methylenedioxy, ethylenedioxy, alkylthio, haloalkylthio, thio, hydroxy, cyano, nitro, a radical of the formula

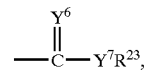

aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, moncyclic heterocycles, or fused moncyclic heterocycles; monocyclic heterocycles; monocyclic heterocycles optionally substituted with one or more substitutent selected from the group consisting of halogen, haloalkyl, lower alkyl, alkoxy, aryloxy, amino, nitro, hydroxy, a radical of the formula

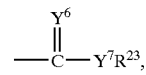

cyano, alkylthio, alkylsulfonyl, aryl, and fused aryl; monocyclic and bicyclic heterocyclicalkyls; —$SO_2R^{10}$— wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsufonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

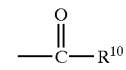

wherein $R^{10}$ is defined above; or $NR^7$ and $R^8$ taken together form a 4–12 membered mononitrogen containing moncyclic or bicyclic ring optionally substituted with one or more substitutent selected from the group consisting of lower alkyl, a radical of the formula

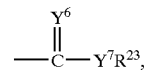

aryl and hydroxy; and wherein said ring optionally contains a heteroatom selected from the group consisting of O, N, and S;

$R^5$ is selected from the group consisting of H, alkyl, alkenyl, alkynyl, benzyl, and phenethyl; or

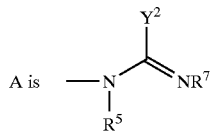

wherein
$Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from the group consisting of halo, haloalkyl, hydroxy, alkoxy, aryloxy, aryl, fused aryl, nitro, methylenedioxy, ethylenedioxy, or alkyl; alkylnyl; alkenyl; —S—$R^9$ and —O—$R^9$— wherein $R^9$ is selected from the group consisting of H; alkyl; aralkyl; aryl; alkenyl; and alkynyl; or $R^9$ taken together with $R^7$ forms a 4–12 membered mononitrogen and monosulfur or monooxygen containing heterocyclic ring optionally substituted with lower alkyl, hydroxy, keto, phenyl, carboxyl or carboxyl ester, and fused phenyl or $R^9$ taken together with $R^7$ is thiazole, oxazole, benzoxazole, or benzothiazole; and $R^5$ and $R^7$ are as defined above; or
$Y^2$ (when $Y^2$ is carbon) taken together with $R^7$ forms a 4–12 membered mononitrogen or dinitrogen containing ring optionally substituted with alkyl, aryl, keto or hydroxy; or

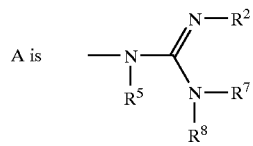

where $R^2$ and $R^7$ taken together form a 5–8 membered dinitrogen containing heterocycle optionally substituted with one or more substituent selected from the group consisting of lower alkyl, hydroxy, alkoxy, keto, phenyl, or a radical of the formula

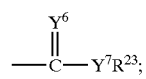

and $R^8$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; and
$R^5$ is defined as above; or
$R^2$ and $R^7$ taken together form a heteroaromatic ring such as imidazole or pyrimidone;
$Z^1$ is one or more substituent selected from the group consisting of H; alkyl; hydroxy; alkoxy; aryloxy; halogen; haloalkyl; haloalkoxy; nitro; amino; alkylamino; acylamino; dialkylamino; cyano; alkylthio; alkylsulfonyl; a radical of the formula

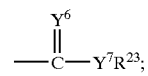

trihaloacetamide; acetamide; acyl; aryl; fused aryl; cycloalkyl; thio; monocyclic heterocycles; fused monocyclic heterocycles; and A, wherein A is defined above;
V is selected from the group consisting of —N—($R^6$)— wherein $R^6$ is selected from the group consisting of H; lower alkyl; cycloalkyl; aralkyl; aryl; and monocyclic heterocycles; or $R^6$ taken together with Y, forms a 4–12 membered mononitrogen containing ring;
Y, $Y^3$, Z and $Z^3$ are independently selected from the group consisting of hydrogen; alkyl; aryl; and cycloalkyl; or Y and Z taken together form a cycloalkyl; or $Y^3$ and $Z^3$ taken together form a cycloalkyl;
n is an integer 1, 2, or 3;
t is an integer 0, 1, or 2;
p is an integer 0, 1, 2, or 3;
R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids; polyalkylethers; alkylamido; alkyl N,N-dialkylamido; pivaloyloxymethyl; and in the case of the free acid, all pharmaceutically acceptable salts thereof;
$R^1$ is selected from the group consisting of hydrogen, alkyl, alkenyl, alkynyl, aryl, a radical of the formula

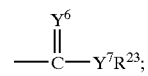

haloalkyl; cycloalkyl; moncyclic heterocycles; monocyclic heterocycles optionally substituted with one or more substituent selected from the group consisting of alkyl, halogen, haloalkyl, cyano, hydroxy, aryl, fused aryl, nitro, alkoxy, aryloxy, alkylsulfonyl, arylsulfonyl, sulfonamide, thio, alkylthio, a radical of the formula

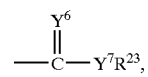

amino, amido; alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, a radical of the formula

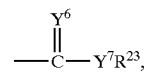

sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, a radical of the formula

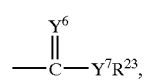

alkoxy, aryloxy, amino, alkylamino, dialkylamino, amido, aryl, fused aryl, moncyclic heterocycles; and fused moncyclic heterocycles, moncyclic heterocyclicthio, moncyclic heterocyclicsulfoxide, and moncyclic heterocyclic sulfone, which can be optionally substituted with halo, haloalkyl, nitro, hydroxy, alkoxy, fused aryl, or alkyl; alkylcarbonyl, haloalkylcarbonyl, and arylcarbonyl; aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, a radical of the formula

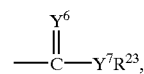

carboxyalkoxy; amido, acylamino, amino, alkylamino, dialkylamino, trifluoroalkoxy, trifluoromethylsulfonyl, alkylsulfonyl, sulfonic acid, sulfonamide, aryl, fused aryl, moncyclic heterocycles and fused heterocycles; and

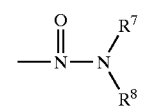

wherein $R^7$ and $R^8$ are defined as above and provided that taken together with the nitrogen, $R^7$ and $R^8$ comprise an amino acid; and $R^{11}$ is selected from the group consisting of H, alkyl, aralkyl, alkenyl, alkylnyl, haloalkyl or haloalkylnyl or $R^{11}$ taken together with Y forms a 4–12 membered mononitrogen containing ring.

2. A compound according to claim 1 of the formula

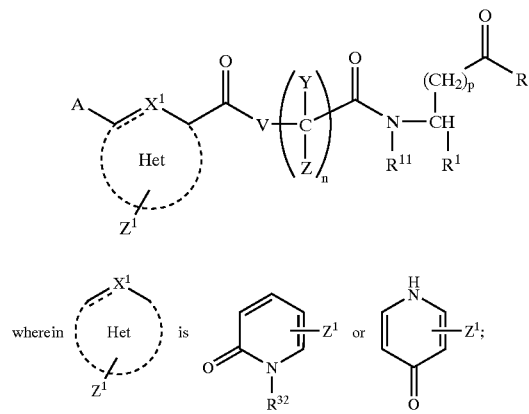

wherein $R^{32}$ is H, alkyl, alkoxyalkyl, aminoalkyl, dialkylamino alkyl, wherein the alkyl group is optionally substituted by one or more substituent selected from the group consisting of hydroxy, alkoxy, amino, alkylamino, dialkylamino, aryl- or alkyl-sulfonyl, carboxyl, and carboxyl derivatives.

3. A compound according to claim 2 wherein the compound is selected from the group consisting of

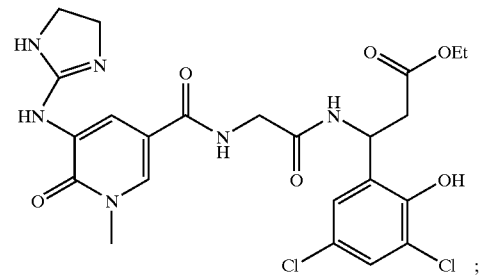

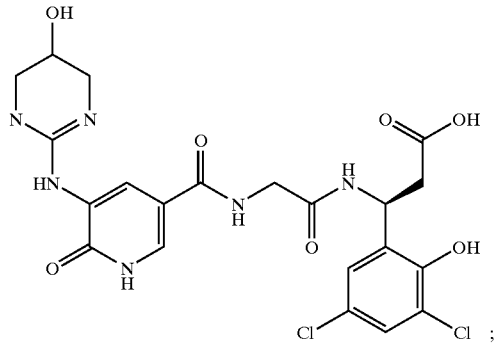

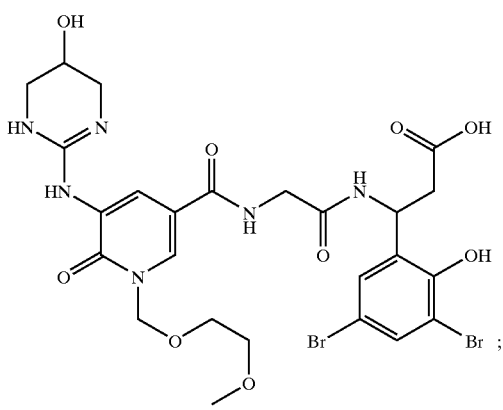

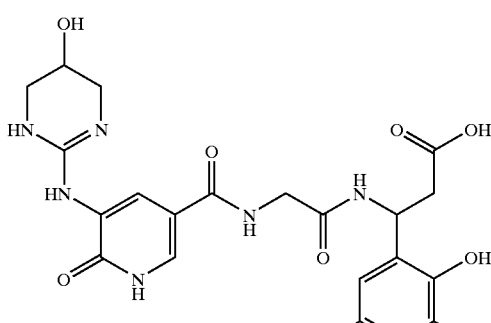

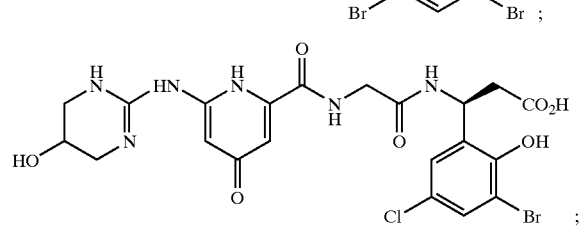

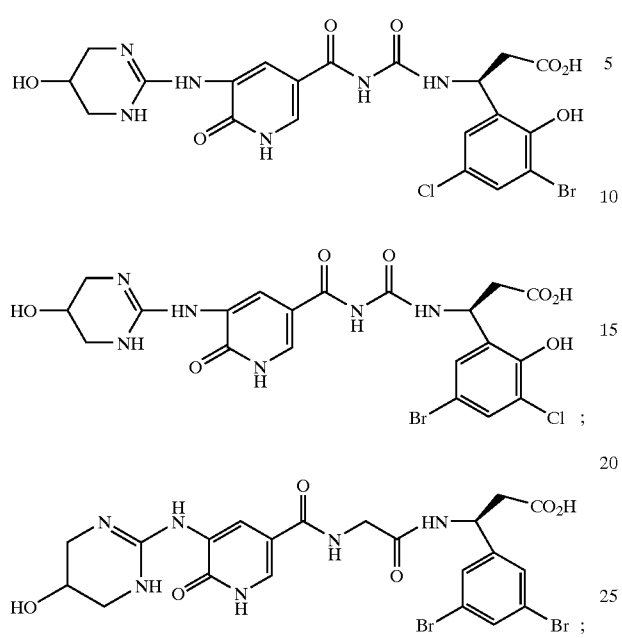
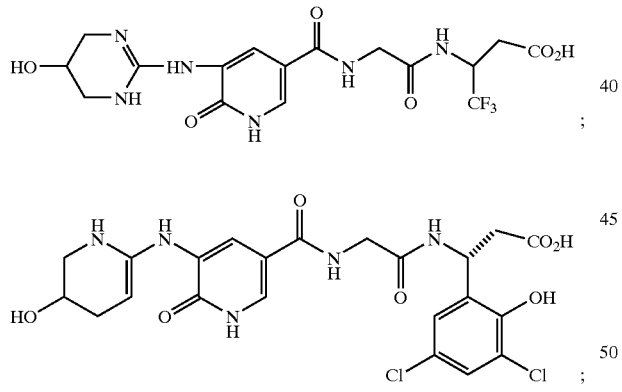
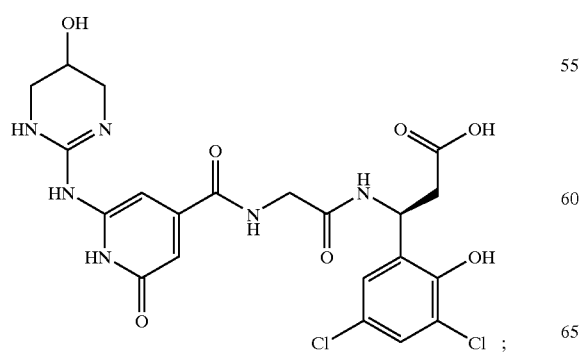
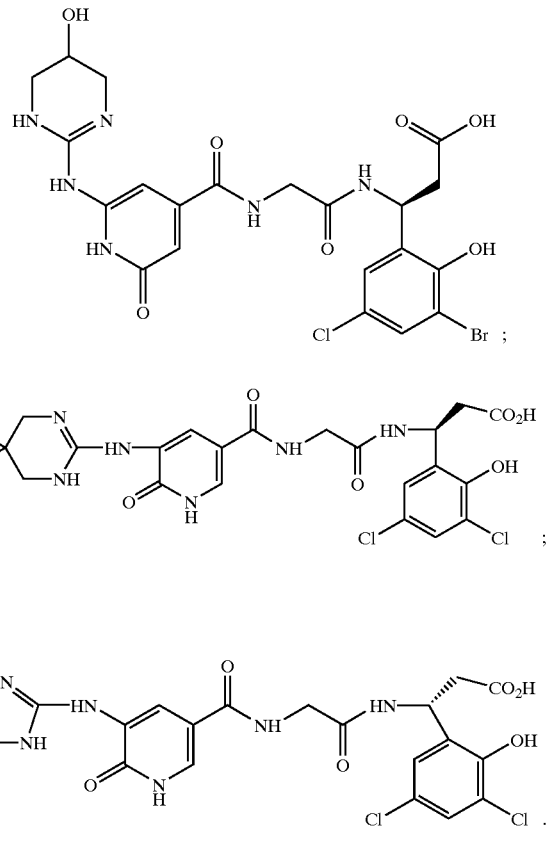
4. A compound according to claim 1 of the formula
wherein Het is
5. A compound according to claim 4 wherein the compound is selected from the group consisting of
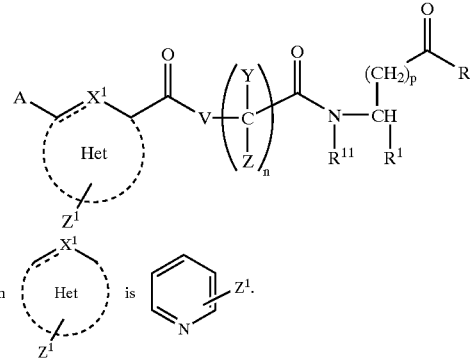
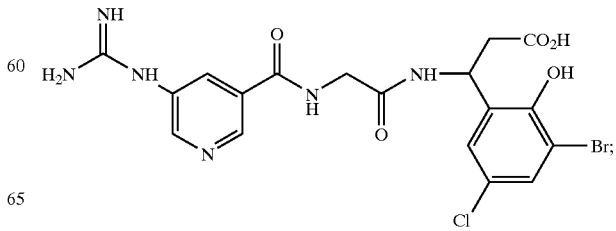

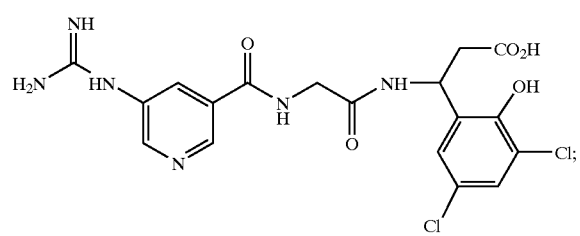
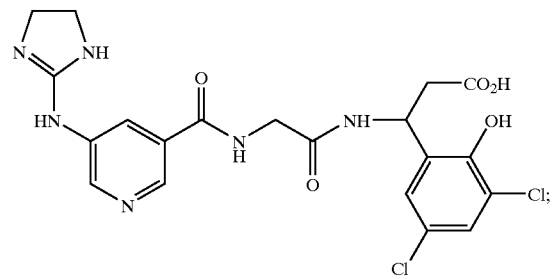
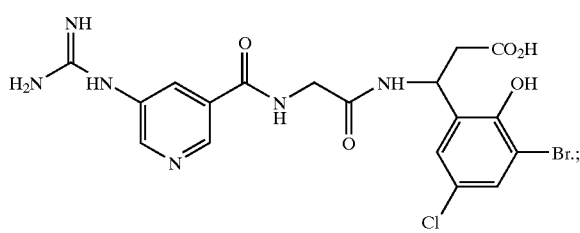
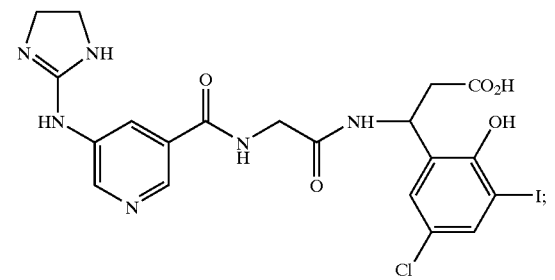
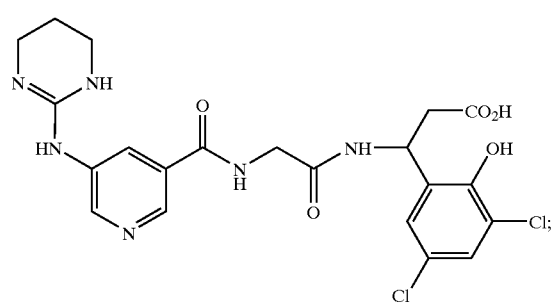
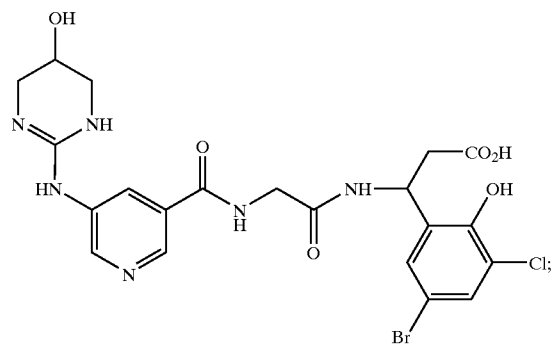
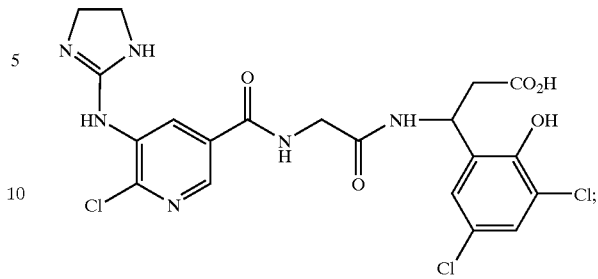
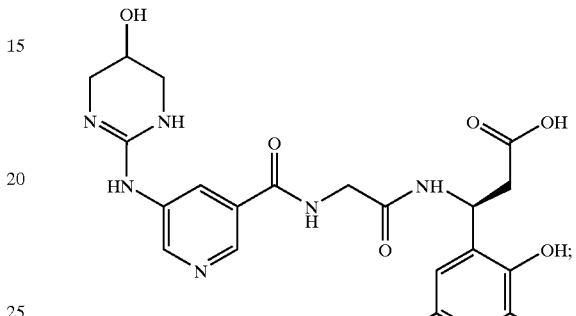
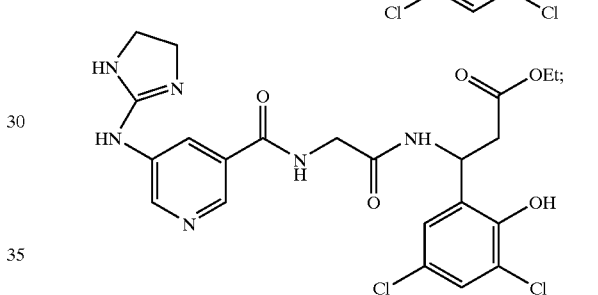
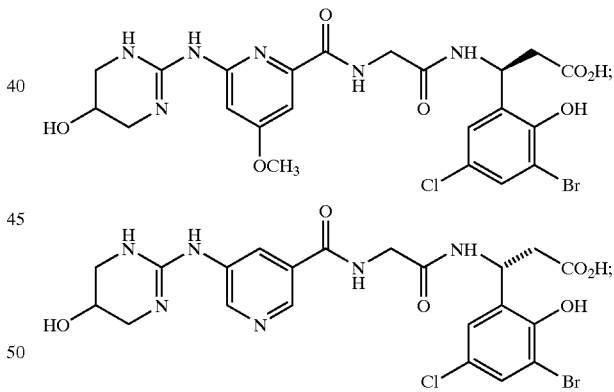
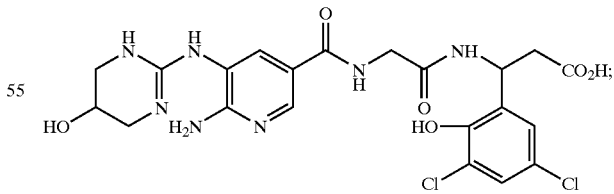
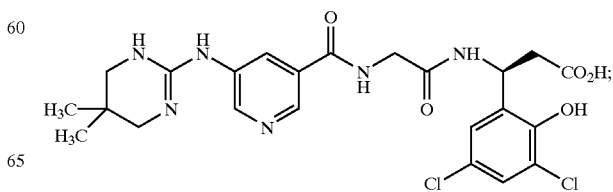

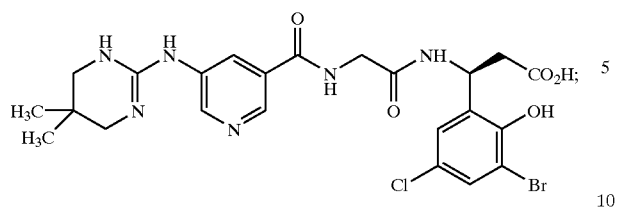
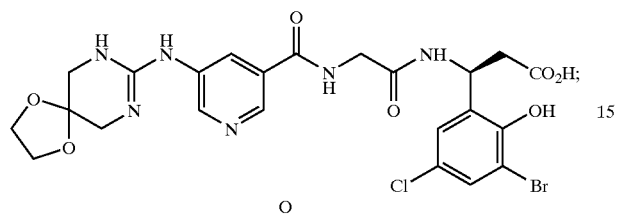
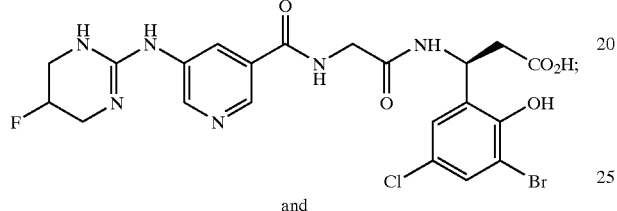
and
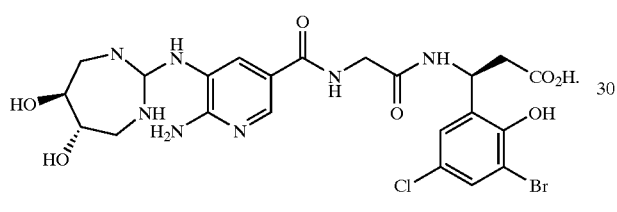
6. A compound according to claim 1 of the formula
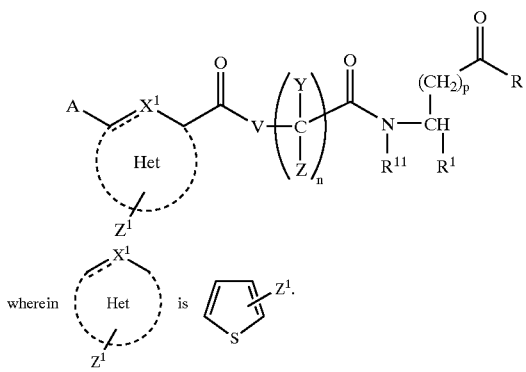
7. A compound according to claim 6 selected from the group consisting of
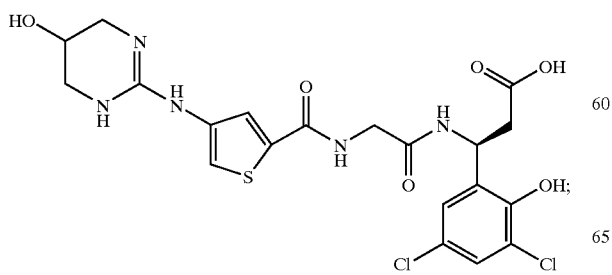
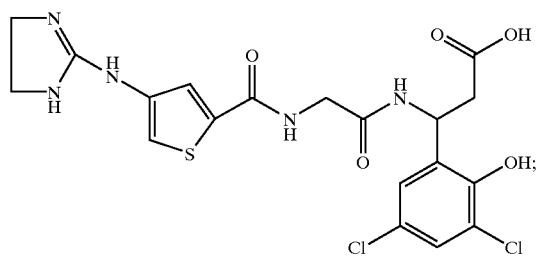
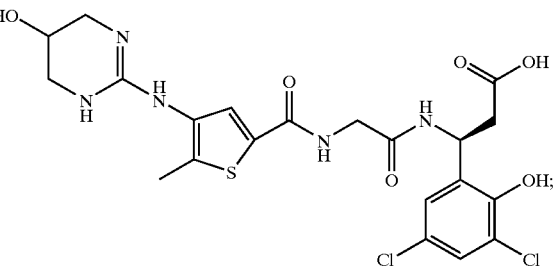
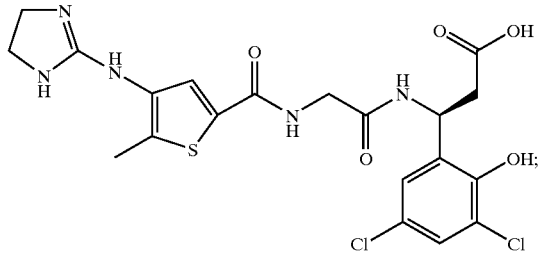
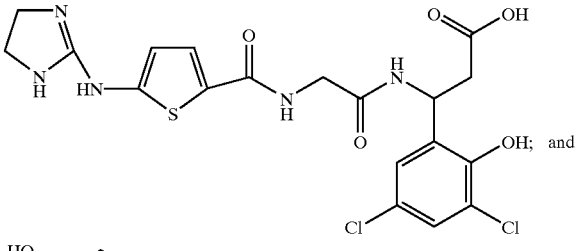
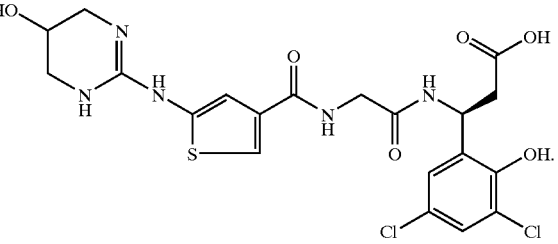
8. A compound according to claim 1 wherein the compound is of the formula
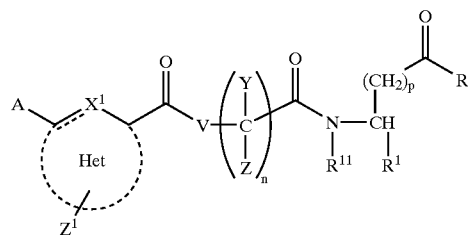

-continued wherein 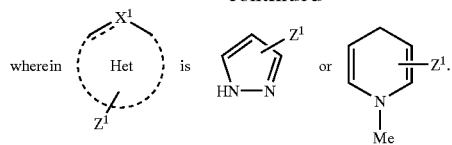

wherein 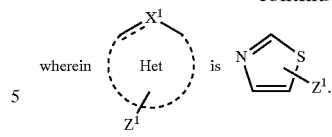

9. A compound according to claim 8 of the formula

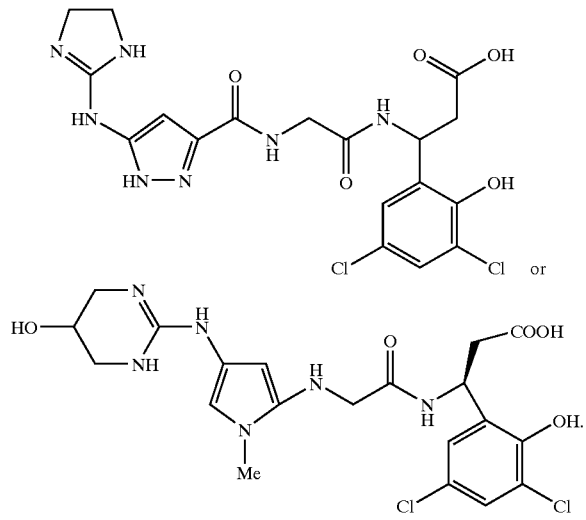

10. A compound according to claim 1 of the formula

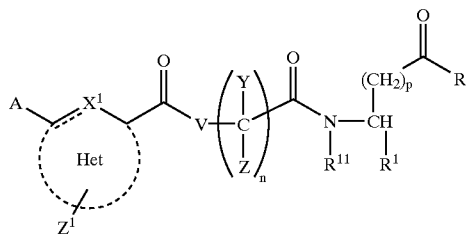

11. A compound according to claim 10 of the formula

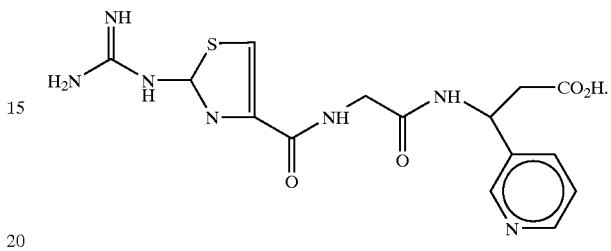

12. A composition comprising a compound according to claims 1, 2, 3, 4, 5, 6, 7, 8, 9, 10, or 11 and a pharmaceutically acceptable carrier.

13. A method of inhibiting angiogenesis comprising administering a compound according to claim 1 to a mammal in need thereof for a time and under conditions effective to antagonize the αvβ3 integrin.

14. A method of inhibiting proliferation of tumor cells comprising administering a compound according to claim 1 to a mammal in need thereof for a time and under conditions effective to antagonize the αvβ3 integrin.

15. A method of inhibiting migration of smooth muscle cells, comprising administering a compound according to claim 1 to a mammal in need thereof for a time and under conditions effective to antagonize the αvβ3 integrin.

* * * * *